(12) United States Patent
Alonso-Alija et al.

(10) Patent No.: US 6,864,287 B1
(45) Date of Patent: Mar. 8, 2005

(54) DERIVATIVES OF DICARBOXYLIC ACID HAVING PHARMACEUTICAL PROPERTIES

(75) Inventors: Cristina Alonso-Alija, Haan (DE); Markus Heil, Leichlingen (DE); Dietmar Flubacher, Breisach (DE); Paul Naab, Wuppertal (DE); Johannes-Peter Stasch, Solingen (DE); Frank Wunder, Wuppertal (DE); Klaus Dembowsky, Boston, MA (US); Elisabeth Perzborn, Wuppertal (DE); Elke Stahl, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/070,033

(22) PCT Filed: Aug. 31, 2000

(86) PCT No.: PCT/EP00/08468

§ 371 (c)(1),
(2), (4) Date: Jun. 27, 2002

(87) PCT Pub. No.: WO01/19776

PCT Pub. Date: Mar. 22, 2001

(30) Foreign Application Priority Data

Sep. 13, 1999 (DE) .......................................... 199 43 634

(51) Int. Cl.$^7$ .......................... C07C 65/28; C07C 69/76; A61K 31/20; A61K 31/235
(52) U.S. Cl. ...................... 514/522; 514/533; 514/568; 560/17; 560/61; 560/62; 560/81; 562/471; 562/472; 562/488; 558/414
(58) Field of Search .............................. 560/17, 61, 62, 560/81; 562/471, 472, 488, 465, 426, 429, 435; 558/414, 423; 514/522, 533, 568

(56) References Cited

U.S. PATENT DOCUMENTS 5,041,638 A * 8/1991 Rosentreter et al. ........ 562/465

FOREIGN PATENT DOCUMENTS

| EP | 0341551 | 11/1989 |
|----|---------|---------|
| EP | 0410241 | 1/1991 |
| EP | 0296732 | 10/1991 |
| EP | 0494621 | 7/1992 |
| EP | 0791576 | 8/1997 |
| WO | 9816223 | 4/1998 |
| WO | 9816507 | 4/1998 |
| WO | 9823619 | 6/1998 |

OTHER PUBLICATIONS

Ko, F., Wu, C., Kuo, S., Lee, F., Tend, C., "YC-1, A Novel Activator of Platelet Guanylate Cyclase", Blood, 84: 4226–4233 (1994).

Mulsch, A., Bauersachs, J., Schafer, A., Stasch, J., Kast, R., Busse, R., "Effect of YC-1, An NO–Independent, Superoxide–Sensitive Stimulator of Soluble Guanylyl Cyclase, On Smooth Muscle Responsiveness to Nitrovasodilators", Br. J. Pharmacol., 120: 681–689 (1997).

Glass, D., Frey, W., Carr, D., Goldberg, N., "Stimulation of Human Platelet Guanylate Cyclase by Faty Acids", J. Biol. Chem., 252: 1279–1285 (1977).

Pettibone, D., Sweet, C., Risley, E., Kennedy, T., "A Structurally Novel Stimulator of Guanylate Cyclase With Long–lasting Hypotensive Activity in the Dog", Eur. J. Pharmacol., 116: 307–312 (1985).

Yu, S., Kuo, S., "Vasorelaxant Effect of Isoliquiritigenin, A Novel Soluble Guanylate Cyclase Activator, in Rat Aorta", Br. J. Pharmacol., 114: 1587–1594 (1995).

Gerzer, R., Bohme, E., Hofmann, F., Schultz, G., "Soluble Guanylate Cyclase Purified From Bovine Lung Contains Heme And Copper", FEBS Lett., 132: 71–74 (1981).

Hoenicka, M., Becker, E., Apeler, H., Sirichoke, T., Schroder, H., Gerzer, R., Stasch, P., "Purified Soluble Guanylyl Cyclase Expressed in a Baculovirus/Sf9 System: Stimulation by YC-1, Nitric Oxide, and Carbon Monoxide", J. Mol. Med., 77: 14–23 (1999).

Ignarro, L., "Regulation of Cytosolic Guanylyl Cyclase by Porphyrins and Metalloporphyrins", Adv. Pharmacol., 26: 35–65 (1994).

Mulsch, A., Bauersachs, J., Stasch, J., Busse, R., "Potentiation of Vascular Responses To No–Donors By an No–Independent Activator of Soluble Guanylyl Cyclase", Naunyn Schmiedebergs Arch. Pharmacol., 355: R47.

* cited by examiner

Primary Examiner—Fiona T. Powers

(57) ABSTRACT

The present invention relates to the compounds of the general formula (I)

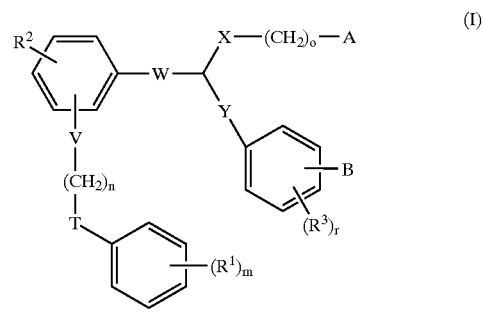

and their salts and stereoisomers for the production of medicaments for the treatment of cardiovascular disorders.

10 Claims, No Drawings

DERIVATIVES OF DICARBOXYLIC ACID HAVING PHARMACEUTICAL PROPERTIES

This application is the national stage filing under 35 U.S.C. §371 of International Application PCT/EP00/08468, filed 31 Aug. 2000, which claims priority of German application No. 199 43 634.7, filed 13 Sep. 1999.

The present invention relates to novel chemical compounds which stimulate soluble guanylate cyclase also via a novel mechanism of action which proceeds without participation of the heme group of the enzyme, to their preparation and to their use as medicaments, in particular as medicaments for treating cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The known representatives of this family can be classified both according to structural features and according to the type of ligands into two groups: the particular guanylate cyclases, which can be stimulated by natriuretic peptides, and the soluble guanylate cyclases, which can be stimulated by NO. The soluble guanylate cyclases consist of two subunits and, most likely, contain one heme per heterodimer, which is part of the regulatory center. It is of central importance for the activation mechanism. NO can bind to the iron atom of the heme and thus increase the activity of the enzyme considerably. In contrast, heme-free preparations cannot be stimulated by NO. CO, too, is capable of attacking the central iron atom of the hem, but the stimulation by CO is considerably lower than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disturbance of the abovementioned processes. Under pathophysiological conditions, the NO/cGMP system can be suppressed, which may lead, for example, to hypertension, platelet activation, increased cell proliferation, endothelial dysfunction, atherosclerosis, angina pectoris, cardiac insufficiency, thromboses, stroke and myocardial infarct.

Owing to the expected high efficiency and few side effects, a treatment of such disorders which targets the influence of the cGMP signal path in organisms and is NO-independent is a promising approach.

Hitherto, for the therapeutic stimulation of the soluble guanylate cyclase use has exclusively been made of compounds such as organic nitrates whose effect is based on NO. This is formed by bioconversion and activates soluble guanylate cyclase by attack at the central iron atom of heme. In addition to the side effects, the development of tolerance is one of the decisive disadvantages of this treatment.

Within the last few years, some substances have been described which stimulate soluble guanylate cyclase directly, i.e. without prior release of NO, such as, for example, 3-(5'-hydroxymethyl-2'-furyl)-1-benzylindazole (YC-1, Wu et al., Blood 84 (1994), 4226; Mülsch et al., Br.J.Pharmacol. 120 (1997), 681), fatty acids (Goldberg et al, J. Biol. Chem. 252 (1977), 1279), diphenyliodonium hexafluorophosphate (Pettibone et al., Eur. 1. Pharmacol. 116 (1985), 307), isoliquiritigenin (Yu et al., Brit. J. Pharmacol. 114 (1995), 1587), and various substituted pyrazole derivatives (WO 98/16223, WO 98/16507 and WO 98/23619).

The known stimulators of the soluble guanylate cyclase stimulate the enzyme either directly via the heme group (carbon monoxide, nitrogen monoxide or diphenyliodoniumhexafluorophosphate) by interaction with the iron center of the heme group and a resulting change in conformation which leads to an increase in enzyme activity (Gerzer et al., FEBS Lett. 132(1981), 71), or via a heme-dependent mechanism which is independent of NO but leads to a potentiation of the stimulating effect of NO or CO (for example YC-1, Hoenicka et al., J. Mol. Med. (1999) 14; or the pyrazole derivatives described in WO 98/16223, WO 98/16507 and WO 98/23619).

The stimulating effect, asserted in the literature, of isoliquiritigenin and of fatty acids, such as, for example, arachidonic acid, prostaglandin endoperoxides and fatty acid hydroperoxides, on the soluble guanylate cyclase could not be confirmed (cf., for example, Hoenicka et al., J. Mol. Med. 77 (1999), 14).

If the heme group of the soluble guanylate cyclase is removed, the enzyme still shows a detectable catalytic basal activity, i.e. as before, cGMP is formed. The remaining catalytic basal activity of the heme-free enzyme cannot be stimulated by any of the abovementioned known stimulators.

Stimulation of heme-free soluble guanylate cyclase by protoporphyrin IX has been described (Ignarro et al., Adv. Pharmacol. 26 (1994), 35). However, protoporphyrin IX can be considered to be a mimic of the NO-heme adduct, owing to which the addition of protoporphyrin IX to soluble guanylate cyclase should result in the formation of an enzyme structure which corresponds to the heme-containing soluble guanylate cyclase which is stimulated by NO. This is also confirmed by the fact that the stimulating effect of protoporphyrin IX is increased by the NO-independent, but heme-dependent, stimulator YC-1 described above (Mülsch et al., Naunyn Schmiedebergs Arch. Pharmacol. 355, R47).

Thus, hitherto no compounds have been described which are capable of stimulating the soluble guanylate cyclase independently of the heme group present in the enzyme.

It was an object of the present invention to develop medicaments for the treatment of cardiovascular disorders or other disorders which can be treated by influencing the cGMP signal path in organisms.

The abovementioned object is achieved by using, for the preparation of medicaments, compounds which are capable of stimulating soluble guanylate cyclase also independently of NO and the heme group present in the enzyme.

Surprisingly, it has been found that there are compounds which are capable of stimulating soluble guanylate cyclase also independently of the heme group present in the enzyme. The biological activity of these stimulators is based on an entirely novel mechanism for stimulating soluble guanylate cyclase. In contrast to the above-described compounds which are known from the prior art as stimulators of soluble guanylate cyclase, the compounds according to the invention are capable of stimulating both the heme-containing and the heme-free form of soluble guanylate cyclase. In the case of these novel stimulators, the stimulation of the enzyme is therefore effected via a heme-independent route, which is also confirmed by the fact that, on the one hand, the novel stimulators do not show any synergistic action with NO at the heme-containing enzyme and, on the other hand, the action of these novel stimulators cannot be blocked by the heme-dependent inhibitor of soluble guanylate cyclase, 1H-1,2,4-oxadiazol-(4,3a)-quinoxalin-1-one (ODQ).

This is a novel therapeutic approach for the treatment of cardiovascular disorders and other disorders which can be treated by influencing the cGMP signal path in organisms.

According to a preferred embodiment of the present invention, alkanoic or alkenoic acid derivatives are used for stimulating soluble guanylate cyclase independently of the heme group in the enzyme.

EP-A-0 341 551 describes alkanoic and alkenoic acid derivatives, such as, for example, (1), which are potent leukotriene antagonists and thus suitable, for example, for use as medicaments for the treatment of asthma or circulatory disorders (p. 18, 1. 56–58). However, a stimulating effect of these compounds on soluble guanylate cyclase and the resulting use of these compounds for preparing medicaments which are capable of influencing the cGMP signal path have not been described.

(1)

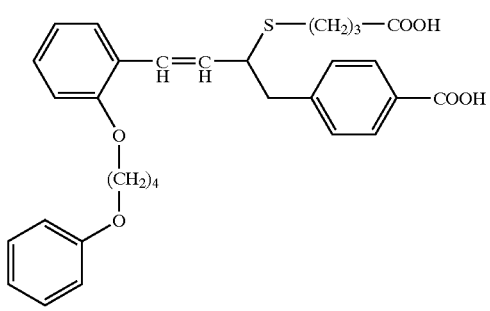

EP-A-0 410 241 describes further alkanoic and alkenoic acid derivatives, such as, for example, (2), having $LTD_4$-, $LTC_4$-, or $LTE_4$-antagonistic action.

(2)

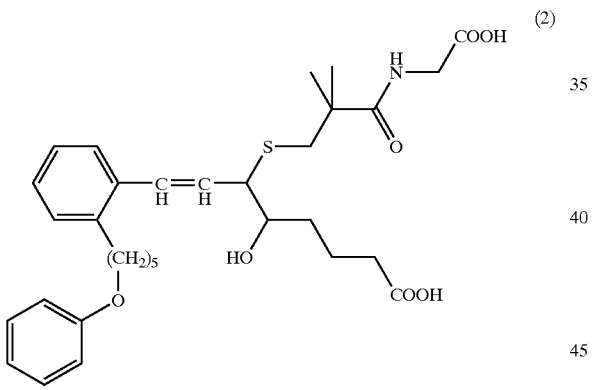

EP-A-0494621 describes sulfur-containing alkenoic acid derivatives, such as, for example, (3), which can be used for allergic diseases, inflammations and cardiovascular disorders.

(3)

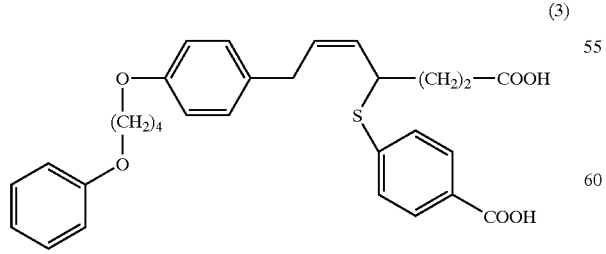

EP-A-0 791 576 describes benzoic acid derivatives, such as, for example, (4), which can be used for treating respiratory disorders.

(4)

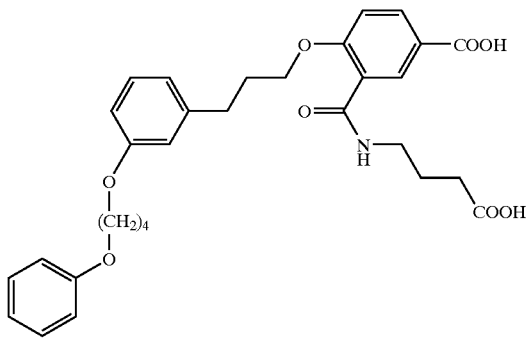

However, it has not been described that any of the abovementioned prior-art compounds have a stimulating effect on soluble guanylate cyclase and can therefore be used for treating disorders which can be treated by influencing the cGMP level.

In a preferred embodiment, the present invention relates to compounds of the general formula (I)

(I)

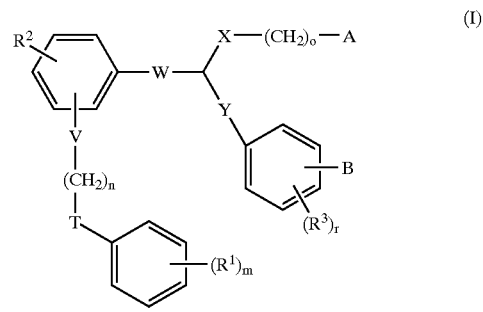

in which

V is absent or represents O, n represents an integer from 1 to 10,

T is absent or represents O.

$R^1$ represents hydrogen, straight-chain or branched alkyl or straight-chain or branched alkoxy having in each case up to 12 carbon atoms, halogen, $CF_3$, $OCF_3$ or CN, m represents 1 or 2, $R^2$ represents hydrogen, straight-chain or branched alkyl or straight-chain or branched alkoxy having in each case up to 12 carbon atoms, halogen, $CF_3$, $OCF_3$ or CN, W represents $CH_2CH_2$ or CH=CH, if W is located on the phenyl ring in a position ortho to the radical V—$(CH_2)_n$-T-Ph-$(R^1)_m$, with the proviso that W does not represent CH=CH if simultaneously T=V=O, $R^1$=$R^2$=$R^3$=H, n=4, Y=$CH_2$, A and B are simultaneously COOH or COOCH$_3$, X is absent or S and o is 3 or 4, or represents $CH_2CH_2CH_2$ or $CH_2$CH=CH, if W is located on the phenyl ring in a position meta to the radical V—$(CH_2)_n$-T-Ph-$(R^1)_m$, with the proviso that W does not represent $CH_2$CH=CH if either simultaneously T=V=O, $R^1$=H or F, m=1, $R^2$=$R^3$=H, n=3, Y=$CH_2$, A and B are simultaneously COOH or COOCH$_3$, X is absent or S and o is 3 or 4, or simultaneously T is absent or O, V is absent, $R^1$=$R^2$=$R^3$=H, n is 4 or 5, Y=$CH_2$, A and B are simultaneously COOH or COOCH$_2$CH$_3$, X is absent and o=4, X is absent or represents straight-chain or branched alkylene having up to 6 carbon atoms, O, $SCH_2$ or $S(O)_p$,
in which
p represents 0, 1 or 2
o represents an integer from 1 to 5
A represents tetrazolyl, tetrazolylmethylene, COOH, $CH_2COOH$, $COOR^4$, $CH_2COOR^5$, $CONR^6R^7$ or CN,
in which
$R^4$ and $R^5$ independently of one another represent straight-chain or branched alkyl having up to 6 carbon atoms,
$R^6$ and $R^7$ independently of one another represent hydrogen, straight-chain or branched alkyl having up to 6 carbon atoms, straight-chain or branched alkylsulfonyl having up to 12 carbon atoms, arylsulfonyl having 6 to 12 carbon atoms,
or
$R^6$ and $R^7$ together with the nitrogen atom to which they are attached form a 3- to 8-membered saturated heterocycle
Y is absent or represents straight-chain or branched alkylene having up to 6 carbon atoms, O, $SCH_2$ or $S(O)_q$,
in which
q represents 0, 1 or 2
B represents tetrazolyl, tetrazolylmethylene, COOH, $CH_2COOH$, $COOR^8$, $CH_2COOR^9$, $CONR^{10}$, $R^{11}$ or CN,
in which
$R^8$ and $R^9$ independently of one another represent straight-chain or branched alkyl having up to 6 carbon atoms,
$R^{10}$ and $R^{11}$ independently of one another represent hydrogen, straight-chain or branched alkyl having up to 6 carbon atoms, straight-chain or branched alkylsulfonyl having up to 12 carbon atoms, arylsulfonyl having 6 to 12 carbon atoms,
or
$R^{10}$ and $R^{11}$ together with the nitrogen atom to which they are attached form a 3- to 8-membered saturated heterocycle,
$R^3$ represents hydrogen, straight-chain or branched alkyl or straight-chain or branched alkoxy having in each case up to 12 carbon atoms, halogen, $CF_3$, $OCF_3$ or CN,
r represents 0, 1 or 2,
and their salts and stereoisomers.

The compounds of the general formula (I) according to the invention may also be present in the form of their salts. In general, salts with organic or inorganic bases or acids may be mentioned here.

In the context of the present invention, preference is given to physiologically acceptable salts. Physiologically acceptable salts of the compounds according to the invention may be salts of the substances according to the invention with mineral acids, carboxylic acids or sulfonic acids. Particular preference is given, for example, to salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may also be the metal or ammonium salts of the compounds according to the invention which have a free carboxyl group. Particular preference is given, for example, to sodium, potassium, magnesium or calcium salts, and to ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention may exist in stereoisomeric forms which are either like image and mirror image (enantiomers) or which are not like image and mirror image (diastereomers). The invention relates both to the enantiomers or diastereomers and to their respective mixtures. The racemates, like the diastereomers, can be separated into stereoisomerically uniform components in a known manner, for example by chromatographic separation. Any double bonds present in the compounds according to the invention can be present in the cis or trans configuration (Z or E form).

In the context of the present invention, the substituents generally have, unless indicated otherwise, the following meanings:

Alkyl generally represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodecyl, eicosyl.

Alkylene generally represents a straight-chain or branched hydrocarbon bridge having 1 to 20 carbon atoms. Examples which may be mentioned are methylene, ethylene, propylene, α-methylethylene, β-methylethylene, α-ethylethylene, β-ethylethylene, butylene, α-methylpropylene, β-methylpropylene, γ-methylpropylene, α-ethylpropylene, β-ethylpropylene, γ-ethylpropylene, pentylene, hexylene, heptylene, octylene, nonylene, decylene, dodeylene and eicosylene.

Alkenyl generally represents a straight-chain or branched hydrocarbon radical having 2 to 20 carbon atoms and one or more, preferably one or two, double bonds. Examples which may be mentioned are allyl, propenyl, isopropenyl, butenyl, isobutenyl, pentenyl, isopentenyl, hexenyl, isohexenyl, heptenyl, isoheptenyl, octenyl, isooctenyl.

Alkinyl generally represents a straight-chain or branched hydrocarbon radical having 2 to 20 carbon atoms and one or more, preferably one or two, triple bonds. Examples which may be mentioned are ethinyl, 2-butinyl, 2-pentinyl and 2-hexinyl.

Acyl generally represents straight-chain or branched lower alkyl having 1 to 9 carbon atoms which is attached via a carbonyl group. Examples which may be mentioned are: acetyl, ethylcarbonyl, propylcarbonyl, isopropylcarbonyl, butylcarbonyl and isobutylcarbonyl.

Alkoxy generally represents a straight-chain or branched hydrocarbon radical having 1 to 14 carbon atoms which is attached via an oxygen atom. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy. The terms "alkoxy" and "alkyloxy" are used synonymously.

Alkoxyalkyl generally represents an alkyl radical having up to 8 carbon atoms which is substituted by an alkoxy radical having up to 8 carbon atoms.

Alkoxycarbonyl can be depicted, for example, by the formula

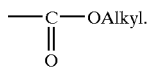

Alkyl here generally represents a straight-chain or branched hydrocarbon radical having 1 to 13 carbon atoms. The following alkoxycarbonyl radicals may be mentioned as examples: methoxycarbonyl, ethoxycarbonyl, propoxycarbonyl, isopropoxycarbonyl, butoxycarbonyl or isobutoxycarbonyl.

Cycloalkyl generally represents a cyclic hydrocarbon radical having 3 to 8 carbon atoms. Preference is given to cyclopropyl, cyclopentyl and cyclohexyl. Examples which may be mentioned are cyclopentyl, cyclohexyl, cycloheptyl and cyclooctyl.

Cycloalkoxy represents, in the context of the invention, an alkoxy radical whose hydrocarbon radical is a cycloalkyl radical. The cycloalkyl radical generally has up to 8 carbon atoms. Examples which may be mentioned are: cyclopropyloxy and cyclohexyloxy. The terms "cycloalkoxy" and "cycloalkyloxy" are used synonymously.

Aryl generally represents an aromatic radical having 6 to 10 carbon atoms. Preferred aryl radicals are phenyl and naphthyl.

Halogen represents, in the context of the invention, fluorine, chlorine, bromine and iodine.

Heterocycle generally represents, in the context of the invention, a saturated, unsaturated or aromatic 3- to 10-membered, for example 5- or 6-membered, heterocycle which may contain up to 3 heteroatoms from the group consisting of S, N and O and which, in the case of a nitrogen atom, may also be attached via this nitrogen atom. Examples which may be mentioned are: oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3-triazolyl, thiazolyl, oxazolyl, imidazolyl, morpholinyl or piperidyl. Preference is given to thiazolyl, furyl, oxazolyl, pyrazolyl, triazolyl, pyridyl, pyrimidinyl, pyridazinyl and tetrahydropyranyl. The term "heteroaryl" (or "hetaryl") represents an aromatic heterocyclic radical.

Preference according to the invention is given to compounds of the formula (I) in which
W represents $CH_2CH_2$ or $CH=CH$ and is located on the phenyl ring in a position ortho to the radical V—$(CH_2)_n$-T-Ph-$(R^1)_m$,
with the proviso that W does not represent $CH=CH$ if simultaneously $T=V=O$, $R^1=R^2=R^3=H$, n=4, $Y=CH_2$, A and B are simultaneously COOH or $COOCH_3$, X is absent or is S and o is 3 or 4,
and the other substituents are as defined above.

Preference according to the invention is furthermore given to compounds of the formula (1) in which
W represents $CH_2CH_2CH_2$ or $CH_2CH=CH$ and is located on the phenyl ring in a position meta to the radical V-$(CH_2)_n$-T-Ph-$(R^1)_m$,
with the proviso that W does not represent $CH_2CH=CH$ if either simultaneously $T=V=O$, $R^1=H$ or F, m=1, $R^2=R^3=H$, n=3, $Y=CH_2$, A and B are simultaneously COOH or $COOCH_3$, X is absent or is S and o is 3 or 4, or simultaneously T is absent or is O, V is absent, $R^1=R^2=R^3=H$, n is 4 or 5, $Y=CH_2$, A and B are simultaneously COOH or $COOCH_2CH_3$, X is absent and o=4,
and the other substituents are as defined above.

Particular preference is given to compounds of the formula (1),
in which
V is absent or represents O,
n represents an integer from 1 to 10,
T is absent or represents O,
$R^1$ represents hydrogen, straight-chain or branched alkyl or straight-chain or branched alkoxy having in each case up to 12 carbon atoms, halogen, $CF_3$, $OCF_3$ or CN,
m represents 1 or 2,
$R^2$ represents hydrogen, straight-chain or branched alkyl or straight-chain or branched alkoxy having in each case up to 12 carbon atoms, halogen, $CF_3$, $OCF_3$ or CN,
W represents $CH_2CH_2$ or $CH=CH$ and is located on the phenyl ring in a position ortho to the radical V—$(CH_2)_n$-T-Ph-$(R^1)_m$,
with the proviso that W does not represent $CH=CH$ if simultaneously $T=V=O$, $R^1=R^2=H$, n=4 and A and B are simultaneously COOH or $COOCH_3$,
X is absent,
o represents an integer from 1 to 4,
A represents COOH or $COOR^4$,
in which
$R^4$ represents alkyl having up to 2 carbon atoms,
Y represents O, S, SO, $SO_2$ or $CH_2$,
B represents COOH, $COOR^8$ or CN,
in which
$R^8$ represents alkyl having up to 2 carbom atoms,
$R^3$ represents hydrogen, straight-chain or branched alkoxy having up to 6 carbon atoms, F, Cl, Br or I,
r represents 0, 1 or 2.

Particular preference is also given to compounds of the formula (1),
in which
V is absent or represents O,
n represents an integer from 1 to 6,
T is absent or represents O,
$R^1$ represents hydrogen, straight-chain or branched alkyl or straight-chain or branched alkoxy having in each case up to 6 carbon atoms, F, Cl, Br or $CF_3$,
m represents 1 or 2,
$R^2$ represents hydrogen or straight-chain or branched alkyl having up to 6 carbon atoms,
W represents $CH_2CH_2$ or CHCH and is located on the phenyl ring in a position ortho to the radical V—$(CH_2)_n$-T-Ph-$(R^1)_m$,
with the proviso that W does not represent $CH=CH$ if simultaneously $T=V=O$, $R^1=R^2=H$, n=4 and A and B are simultaneously COOH or $COOCH_3$,
X is absent,
o represents an integer from 1 to 4,
A represents COOH or $COOR^4$,
in which
$R^4$ represents alkyl having up to 2 carbon atoms,
Y represents O, S or $CH_2$,
B represents COOH, $COOR^8$ or CN,
in which
$R^8$ represents alkyl having up to 2 carbon atoms,
$R^3$ represents hydrogen, straight-chain or branched alkoxy having up to 4 carbon atoms, Cl or Br,
r represents 0, 1 or 2.

Especially preferred are compounds of the formula (1),
in which
V is absent or represents O,
n represents an integer from 1 to 10,
T is absent or represents O, $R^1$ represents hydrogen, straight-chain or branched alkyl or straight-chain or branched alkoxy having in each case up to 12 carbon atoms, halogen, $CF_3$, $OCF_3$ or CN, m represents 1 or 2, $R^2$ represents hydrogen, straight-chain or branched alkyl or straight-chain or branched alkoxy having in each case up to 12 carbon atoms, halogen, $CF_3$, $OCF_3$ or CN, W represents $CH_2CH_2CH_2$ or $CH_2CH=CH$ and is located on the phenyl ring in a position meta to the radical $V—(CH_2)_n$-T-Ph-$(R^1)_m$, with the proviso that W does not represent $CH_2CH=CH$ if either simultaneously T=V=O, $R^1$=H or F, m=1, $R^2$=H, n=3 and A and B are simultaneously COOH or $COOCH_3$, or simultaneously T is absent or represents O, V is absent, $R^1=R^2$=H, n is 4 or 5, A and B are simultaneously COOH or $COOCH_2CH_3$, and o=4, X is absent, o represents 3 or 4, A represents COOH or $COOR^4$, in which $R^4$ represents alkyl having up to 2 carbon atoms, Y represents $CH_2$, B represents COOH, $COOR^8$ or CN, in which $R^8$ represents alkyl having up to 2 carbon atoms, $R^3$ represents hydrogen.

Especially preferred are also compounds of the formula (I), in which

V is absent or represents O, n represents an integer from 1 to 6,

T is absent or represents 0, $R^1$ represents hydrogen, straight-chain or branched alkyl or straight-chain or branched alkoxy having in each case up to 6 carbon atoms, F, Cl, Br or $CF_3$, m represents 1 or 2, $R^2$ represents hydrogen, straight-chain or branched alkyl having up to 6 carbon atoms, F, Cl, Br or $CF_3$, W represents $CH_2CH_2CH_2$ or $CH_2CH=CH$ and is located on the phenyl ring in a position meta to the radical $V—(CH_2)_n$-T-Ph-$(R^1)_m$, with the proviso that W does not represent $CH_2CH=CH$ if either simultaneously T=V=O, $R^1$=H or F, m=1, $R^2$=H, n=3 and A and B are simultaneously COOH or $COOCH_3$, or simultaneously T is absent or represents O, V is absent, $R^1=R^2$=H, n is 4 or 5, A and B are simultaneously COOH or $COOCH_2CH_3$, and X is absent, o represents 3 or 4, A represents COOH or $COOR^4$, in which $R^4$ represents alkyl having up to 2 carbon atoms, y represents $CH_2$, B represents COOH, COORS or CN, in which $R^8$ represents alkyl having up to 2 carbon atoms, $R^3$ represents hydrogen.

Very particularly preferred according to the invention are compounds of the formula (I) in which A and B each represent COOH and the other substituents are as defined in claim 3.

Particular preference according to the invention is furthermore given to compounds in which V represents 0 and T is absent and the other substituents are as defined in claim 3.

Preference according to the invention is furthermore given to compounds in which V and T are absent, n represents an integer from O to T and the other substituents are as defined in claim 3.

The present invention furthermore relates to a process for preparing the compounds of the formula (I) according to the invention

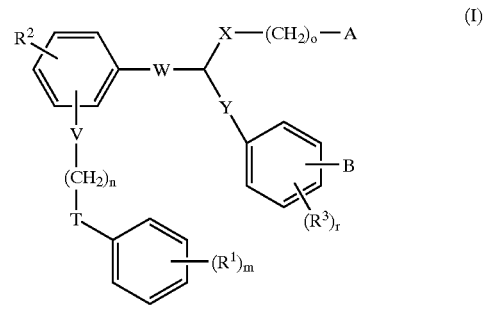

in which $R^1$, $R^2$, $R^3$, A, B, T, V, W, X, Y, m, n, o and r have the meaning given above, comprising

[α] the reaction of aldehydes of the general formula (II)

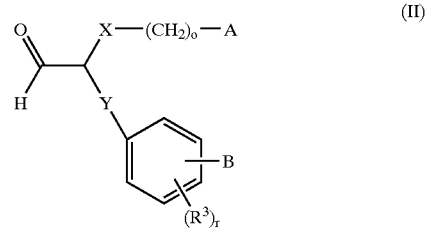

in which $R^3$, A, B, X, Y, o and r have the meaning given above, with the proviso that A and B may not represent free carboxyl groups, with phosphorus compounds of the general formula (ID)

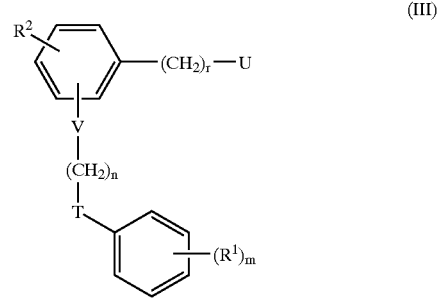

in which $R^1$, $R^2$, T, V, m and n have the meanings given above, r represents 1 or 2, and U represents a radical of the formula

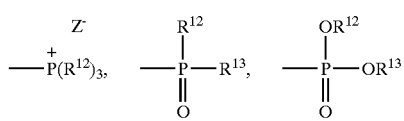

in which $R^{12}$ and $R^{13}$ independently of one another represent straight-chain or branched alkyl having up to 12 carbon atoms or phenyl, and Z represents a halide anion or tosylate anion, in inert solvents in the presence of a base, and, if appropriate, the subsequent partial or complete hydrolysis of the radicals A and B to free carboxylic acid groups; or

[β] the reaction of aldehydes of the formula (i)

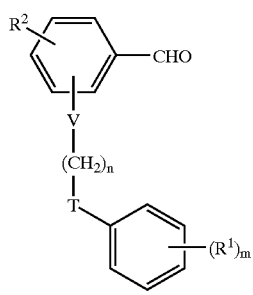

(i)

in which $R^1$, $R^2$, T, V, m and n have the meanings given above with phosphorus compounds of the formula (ii)

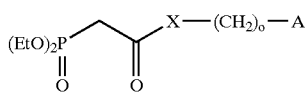

(ii)

in which

X, o and A have the meanings given above, to give compounds of the formula (iii)

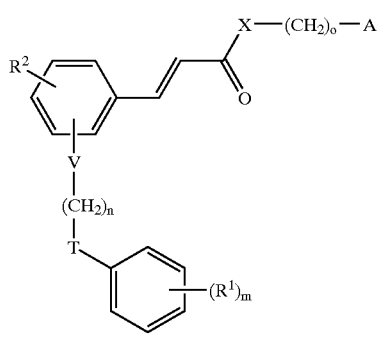

(iii)

in which $R^1$, $R^2$, T, V, m, n, X, o and A have the meanings given above, and the subsequent conversion of the compounds of formula (iii) into compounds of the formula (Iv)

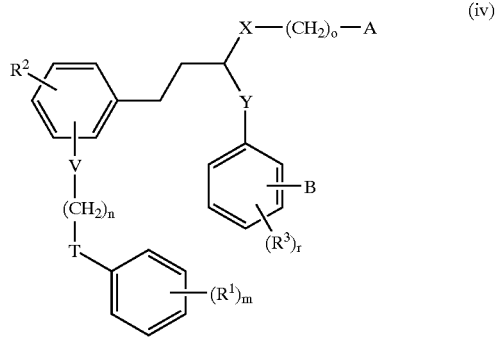

(iv)

in which $R^1$, $R^2$, T, V, m, n, X, o, r, A, B and $R^3$ have the meanings given above, Y represents O, $SCH_2$ or S, by successive reduction of the carbonyl group and the alkene group and subsequent substitution of the hydroxyl group, formed by the reduction of the carbonyl group, with alcohols or thiols and, if appropriate, subsequent oxidation to the corresponding sulfoxide or sulfone compounds.

According to the invention, Z preferably represents a halide anion, particularly preferably chloride, bromide or iodide.

According to the invention, the partial or complete hydrolysis to the corresponding free carboxylic acid groups, which is to be carried out, if appropriate, is preferably carried out using strong acids, such as, for example, HCl, or using strong bases, such as, for example, NaOH or LiOH, which are present in aqueous solution or in solvent mixtures of water with alcohols, such as, for example, methanol, or ethers.

Preferred inert solvents for the process according to the invention are customary organic solvents which do not change under the reaction conditions. For the process according to the invention, preference is given to using ethers, such as diethyl ether, butyl methyl ether, dioxane, tetrahydrofuran, glycol dimethyl ether or diethylene glycol dimethyl ether, or hydrocarbons, such as benzene, toluene, xylene or petroleum ether, or amides, such as dimethylformamide or hexamethylphosphoric triamide, or 1,3-dimethyl-imidazolidin-2-one, 1,3-dimethyl-tetrahydropyrimidin-2-one or dimethylsulfoxide. It is, of course, also possible to use mixtures of the solvents mentioned above.

Bases which are preferred for the process according to the invention include basic compounds which are customarily used for basic reactions. Preference is given to using alkali metal hydrides, such as, for example, sodium hydride or potassium hydride, or alkali metal alkoxides, such as sodium methoxide, sodium ethoxide, potassium methoxide, potassium ethoxide or potassium t.-butoxide, or amides, such as sodium amide or lithium diisopropylamide, or sodium hexamethyldisilazane, or organolithium compounds, such as phenyllithium, butyllithium or methyllithium. To optimize the reaction, in the process according to the invention a customary crown ether such as 18-crown-6 may be added, if appropriate.

The selection of the solvent or base depends on the stability, sensitivity to hydrolysis or the CH activity of the corresponding phosphorus compound. Solvents that are particularly preferably used are ethers, such as diethyl ether, tetrahydrofuran, dimethoxyethane or dioxane, together with a cosolvent, such as dimethylformamide or 1,3-dimethyltetrahydropyridin-2-one or 1,3-dimethylimidazolidin-2-one. Alkali metal alkoxides, such as potassium tert-butoxide, or organolithium compounds, such as phenyllithium or butyllithium, or sodium hydride are bases which are particularly preferably used.

The reaction can generally be carried out in a temperature range of from −80° C. to c+70° C., preferably from −80° C. to +20° C.

The reaction can be carried out at atmospheric pressure, elevated or reduced pressure (for example in a range of from 0.5 to 5 bar). In general, the reaction is carried out at atmospheric pressure.

When carrying out the reaction, the phosphorus compounds are generally employed in an amount of 1 to 2 mol, based on 1 mol of aldehyde. The bases are generally employed in an amount of 1 to 5 mol, preferably 1 to 2 mol, based on 1 mol of phosphorus compound.

The process [α] according to the invention can be carried out, for example, by adding the base and then the aldehyde, if appropriate in a solvent, to, the phosphorus compound which is suspended or dissolved in a solvent, and subsequently, if appropriate, heating the mixture. Work-up is carried out in a customary manner, by extraction, chromatography and/or crystallization.

When carrying out the process [α] according to the invention, it is also possible to use, instead of the phosphonium salts mentioned above, the corresponding phosphoranes (U equals —P(R$^{12}$)$_3$=CHR) which are prepared beforehand in a separate reaction from the corresponding phosphonium salts in basic medium. However, it has been found to be advantageous to carry out the reaction with the phosphorus compounds in the presence of bases as a one-pot process.

The phosphorus compounds of the general formula (i) can be prepared by the following different routes.

Process A-1. Variant

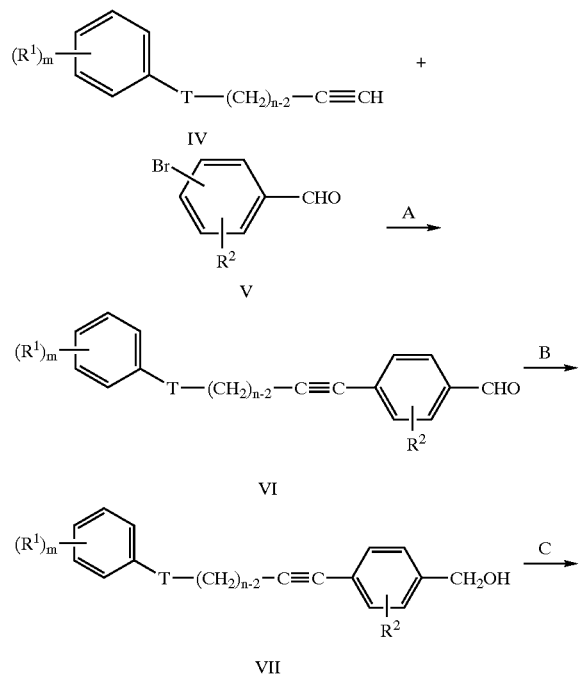

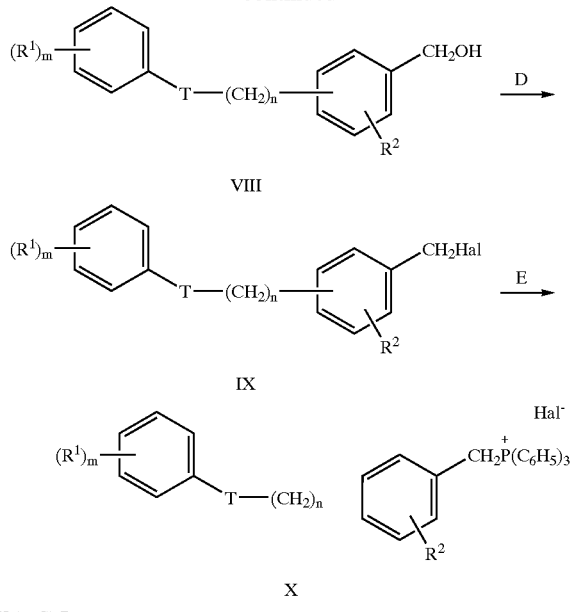

Hal = Cl, Br

In the first reaction step [A] of this variant, the acetylene compounds (IV) are reacted with the bromobenzaldehydes (V) in solvents such as triethylamine, acetonitrile, pyridine or mixtures thereof, preferably in triethylamine, in the presence of copper(I) salts and palladium(0) compounds, preferably in the presence of copper(I) halides, such as, for example, copper iodide, and bistriphenylphosphine)-palladium(II) chloride, in a temperature range of from −40° C. to +80° C., preferably from 0° C. to +40° C.

In the second reaction step [B], the formyl compound (VI) is reduced in solvents such as alcohols, for example methanol, ethanol, propanol or isopropanol, or ethers, such as diethyl ether, tetrahydrofuran or dioxane, or basic solvents, such as triethylamine, pyridine or dimethylformamide, or in water or in mixtures of the above-mentioned solvents, using complex hydrides, such as, for example, borohydrides or aluminum hydrides, preferably sodium borohydride or lithium aluminum hydride, as reducing agents, in a temperature range of from −40° C. to +60° C., preferably from 0° C. to +40° C., to give the hydroxyl compounds (VII).

In the third reaction step [C], the compounds (VII) are hydrogenated in inert solvents such as alcohols, for example methanol, ethanol, propanol or isopropanol, or hydrocarbons, such as benzene, toluene or xylene, or in ethers, such as diethyl ether or tetrahydrofuran, or in ethyl acetate, particularly preferably in methanol, in the presence of noble metal catalysts, such as palladium or platinum, in a temperature range of from −30° C. to +80° C., preferably from 0° C. to +40° C., under a pressure of from 1 bar to 50 bar, preferably from 1 bar to 20 bar.

Steps B and C can also be carried out in reverse order.

In the fourth step [D], the hydrogenated compounds (VIII) are brominated by reaction with brominating agents, such as, for example, phosphorus tribromide, sulfonyl bromide, hydrogen bromide or carbon tetrabromide/triphenylphosphine, in inert solvents, such as ethers, for example diethyl ether or tetrahydrofuran, or hydrocarbons, such as benzene or toluene, or, particularly preferably, chlorinated hydrocarbons, such as methylene chloride or chloroform, in a temperature range of from −20° C. to +60°

C., preferably from 0° C. to +40° C. However, it is also possible to use the corresponding chlorine compounds which are obtainable, for example, by reacting the compounds VIIIa with SOCl$_2$.

In the fifth reaction step [E], the brominated or chlorinated compounds (IX) are reacted with triphenylphosphine in inert solvents such as acetonitrile or hydrocarbons, such as benzene, toluene or xylene, or benzonitrile or dimethylformamide or dimethyl sulfoxide or in an alcohol, such as methanol, ethanol, propanol, butanol or isopropanol or in the absence of a solvent, in a temperature range of from 0° C. to +200° C., preferably from +20° C. to +180° C., with formation of the phosphonium salts (X).

Using this process, it is possible to obtain the compounds of the formula (I) according to the invention in which V is absent and T is absent or represents O. In the compounds of the formulae (IV) to (X), the radicals R$^1$, R$^2$ and T have the same meanings as defined in claim 3.

The acetylene compounds of the formula (IV) can be obtained, for example, by reacting corresponding phenol compounds with ω-halogenoalkines in the presence of bases. Particular preference is given here to ω-chloroalkines such as, for example, 5-chloro-1-pentine. Suitable for use as bases are, for example, metal hydrides, such as sodium hydride. The phenols to be used as starting materials are commercially available or can be prepared by standard reactions known to the person skilled in the art (cf., for example, J. March, Advanced Organic Chemistry, 3. Edition, Wiley, p. 1170 f.). The conversion into the acetylene compounds of the formula (IV) can be carried out in organic solvents, such as, for example, ethers, in particular tetrahydrofuran, at temperatures of from +20° C. to +80° C., under an atmosphere of inert gas, for example argon. In some cases, it may be advantageous to add complexing agents, such as hexaphosphoric triamide. Alternatively, the acetylene compounds (IV) can be obtained by reacting corresponding substrates having a group which is nucleophilically substitutable, for example (  )-halogenoalkylphenyl compounds, preferably ω-chloroalkylphenyl compounds, with acetylides, such as, for example, sodium acetylide or lithium acetylide, under conditions known to the person skilled in the art (cf., for example, J. March, Advanced Organic Chemistry, 3. edition, Wiley, p. 429).

Process A-2. variant

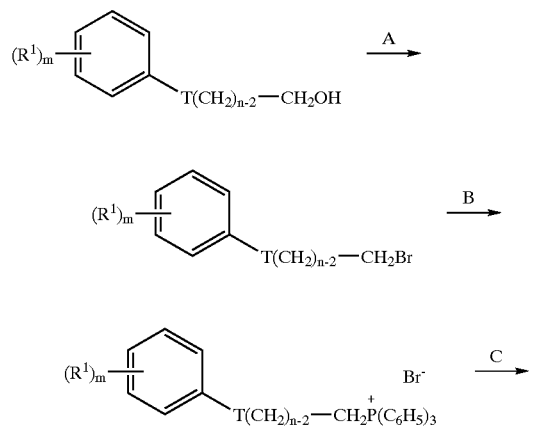

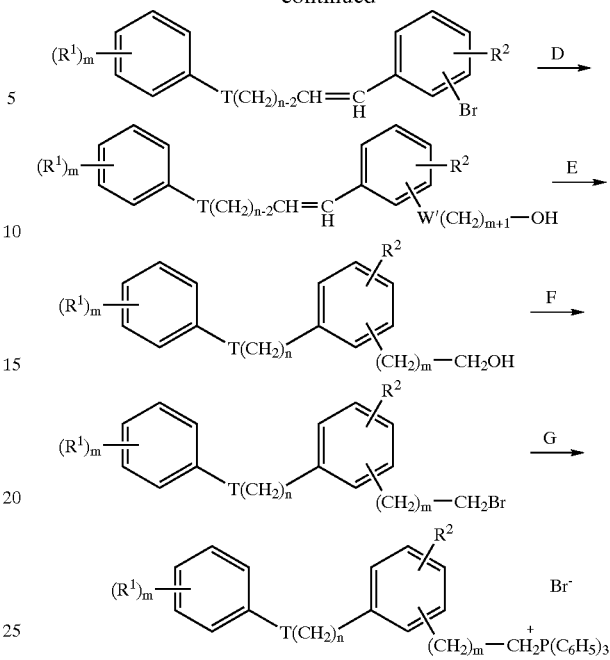

In the first reaction step, the alcohols used as starting materials are brominated, suitable brominating agents being, for example, the compounds listed in step D of the 1, variant of process A.

The resulting bromides are reacted with triphenylphosphine as in step E of the 1. variant of process A.

In the next reaction step, the reactive Ylide is generated as illustrated above, and this is then reacted with a bromobenzaldehyde having the desired substitution pattern.

From the resulting compound, it is possible to obtain, by reaction with the base, preferably t-butyllithium, in an inert solvent (tetrahydrofuran), at low temperatures and subsequent addition of an appropriate electrophile, such as paraformaldehyde or ethylene oxide, the corresponding primary alcohols (W' is a direct bond). Alternatively, the resulting compounds can be converted using an optionally protected hydroxyalkine such as the tetrahydropyranyl ether of propargyl alcohol, under the same conditions as in process step [A] of the 1. variant of process A (W' is C≡C), followed by a hydrogenation, which can be carried out analogously to step C of the 1. variant of process A, into the primary alcohols. The resulting primary alcohols are, analogously to the 1. variant of process A, converted into the corresponding phosphonium salts.

Using this process, it is possible to obtain the compounds of the formula (I) according to the invention in which V is absent and T is absent or represents O.

The alcohols used as starting materials in this process, for example hydroxyalkyl-oxyphenyl compounds or hydroxyalkylphenyl compounds, are either commercially available or can be prepared by customary reactions known to the person skilled in the art.

In the compounds shown in the diagram above, the radicals R$^1$, R$^2$ and T have the same meanings as defined in claim 3.

Process B-1. variant

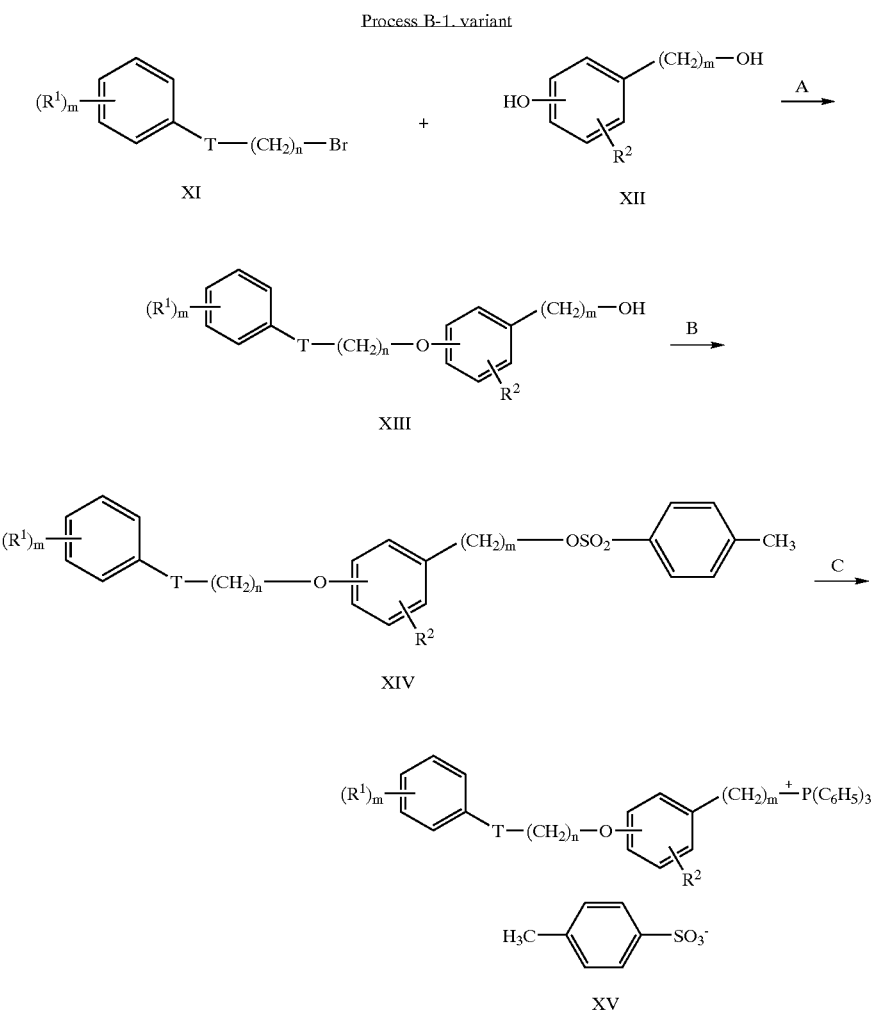

In the first reaction step of this variant, the bromine compounds (XI) are reacted with the phenols (XII) in preferred solvents such as water or alcohols, such as, for example, methanol, ethanol, propanol or isopropanol, or ethers, such as diethyl ether, tetrahydrofuran, dioxane or dimethyloxymethane, or dimethylformamide or dimethyl sulfoxide, or acetonitrile or ketones, such as, for example, acetone, particularly preferably in isopropanol, in the presence of bases, such as alkali metal hydroxides, carbonates or alkoxides, such as, for example, sodium carbonate, potassium carbonate, cesium carbonate, sodium hydroxide, potassium hydroxide, sodium ethoxide or potassium t-butoxide, in a temperature range of from 0° C. to 200° C., preferably from +20° C. to +180° C.

In the second step [B], the phenyl ethers (XI) are reacted with tosyl chloride in inert solvents such as ethers, for example diethyl ether, tetrahydrofuran or dioxane, or hydrocarbons, such as benzene or toluene, or chlorinated hydrocarbons, such as chloroform or methylene chloride, or in ethyl acetate, acetone or acetonitrile, preferably in methylene chloride, in the presence of bases, such as triethylamine, pyridine or dimethylaminopyridine, preferably in the presence of pyridine, in a temperature range of from −30° C. to +50° C., preferably from −10° C. to +30° C.

In the third reaction step [I], the tosyl compounds (XIV) are reacted with triphenyl-phosphine in preferred solvents such as hydrocarbons, for example benzene or toluene, benzonitrile, acetonitrile, dimethylformamide or dimethyl sulfoxide, or in the absence of a solvent, particularly preferably in acetonitrile, in a temperature range of from 0° C. to +200° C., preferably from +20° C. to +180° C., giving the phosphonium salts (XV).

In steps B and C, the hydroxyl compound XIII can also, analogously to steps D and E of the first variant of process A, be initially converted into the bromide and then into the phosphonium salt.

Using this process, it is possible to obtain the compounds of the formula (I) according to the invention in which V is O.

Process B-2. variant

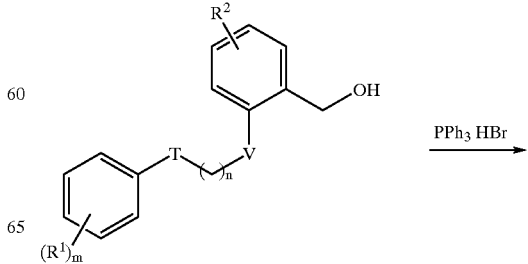

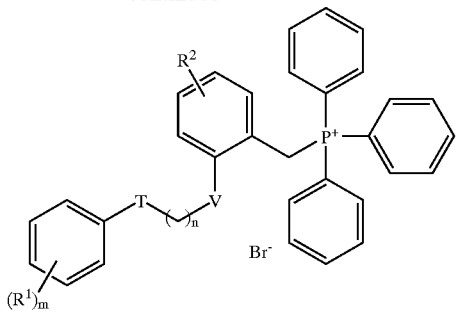

In this variant, the corresponding alcohols, for example hydroxyalkylphenyl compounds, are reacted with triphenylphosphonium hydrobromide in an organic solvent, such as, for example, acetonitrile, at a temperature of from +30° C. to +100° C., preferably from +50° C. to +90° C. The starting materials can be obtained in a customary manner. For example, in the case that T is absent and V is O, by reacting a corresponding halogenoalkylphenyl compound, preferably a chloro- or bromoalkylphenyl compound, such as, for example, benzyl bromide, with a corresponding phenol compound, such as, for example, 2-hydroxybenzylalcohol, in an organic solvent, such as an alcohol, preferably isopropanol, in the presence of a base, such as, for example, potassium carbonate, at a temperature from +30 to 100° C., preferably from +50 to 90° C. reacted.

In the compounds shown in the above diagrams of process B, the radicals $R^1$, $R^2$ and T have the same meanings as defined in claim 3.

Process B-3. variant

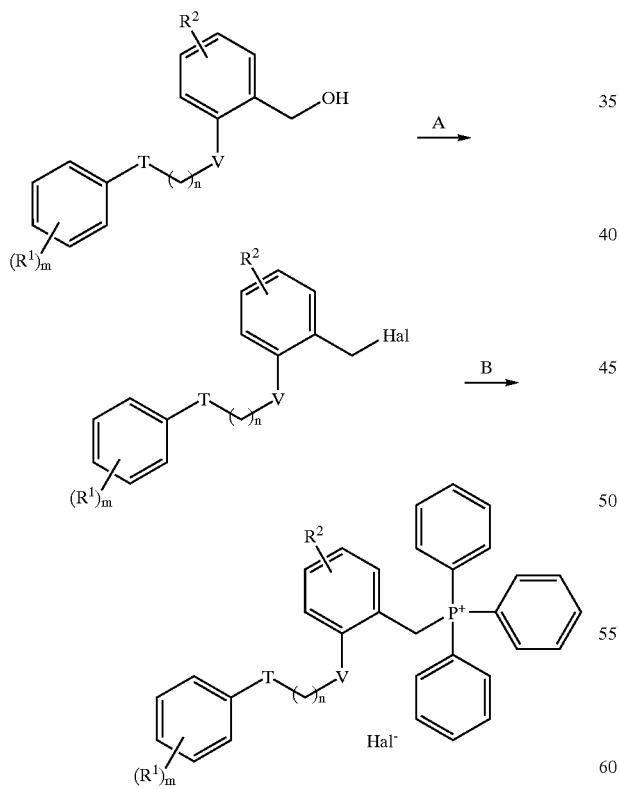

Hal = Cl, Br

In this variant, the alcohol is initially, according to step D of process A, variant 1, converted into a halide, which is then, analogously to step E of process A, variant 1, converted into the desired phosphonium salt.

In this variant, $R^1$, $R^2$, T, V and n have the meanings given above.

Depending on the meanings of X and Y, the aldehydes of the general formula (II) can be prepared, for example, by the process below.

Process C

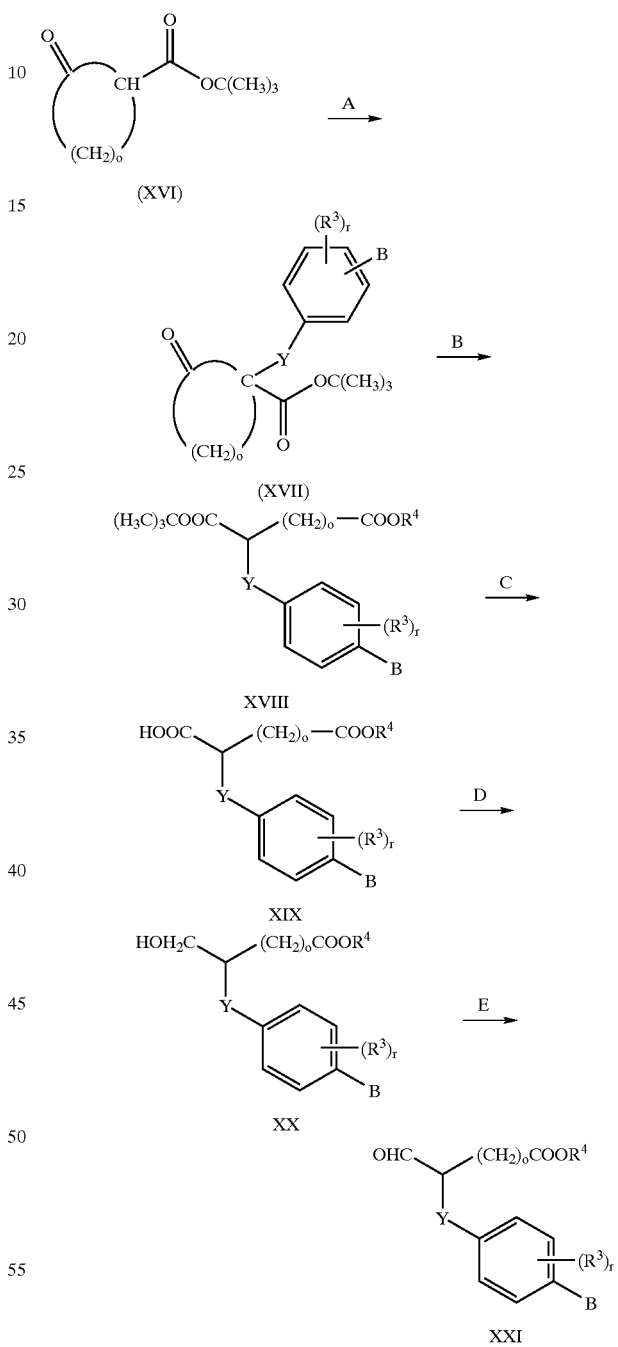

In the first reaction step [A] of this variant, the ketone (XVI) (where o is 3, 4 or 5) is reacted with 4-halogenomethylbenzoic acid esters or 4-halogenosulfenylbenzoic acid esters, where the halogen radical is preferably chlorine or bromine, or the corresponding nitrites, in inert solvents, such as in ether, for example diethyl ether, tetrahydrofuran or dioxane, or dimethylformamide, or dimethyl sulfoxide, or in mixtures thereof, particularly preferably in dimethylformamide, in the presence of bases, such as alkali metal hydrides, amides or alkoxides, such as sodium hydride, potassium hydride, lithium diisopropylamide, potassium ethoxide, sodium ethoxide, potassium methoxide or potassium t-butoxide, particularly preferably in the presence of sodium hydride, in a temperature range of from −40° C. to +60° C., particularly preferably from −20° C. to +30° C.

In the second reaction step [B], the ketones (XVII) are reacted in solvents such as dimethylformamide or alcohols, for example methanol, ethanol, propanol or isopropanol, or in water or mixtures thereof, particularly preferably in dimethylformamide or ethanol, in the presence of bases, such as alkali metal hydroxides, alkali metal carbonates or alkali metal alkoxides, such as sodium hydroxide, potassium hydroxide, sodium carbonate, sodium methoxide, sodium ethoxide, potassium ethoxide or potassium t-butoxide, particularly preferably in the presence of potassium t-butoxide, in a temperature range of from 0° C. to +150° C., particularly preferably from +20° C. to +100° C., giving the compounds (XVIII).

In the third reaction step [C], the compounds (XVIII) are hydrolyzed in solvents such as alcohols, for example methanol, ethanol, propanol or isopropanol, or in ethers, for example methyl ether, tetrahydrofuran or dioxane, or in chlorinated hydrocarbons, such as methylene chloride or chloroform, or carboxylic acids, such as acetic acid or trifluoroacetic acid, or in mixtures thereof, particularly preferably in trifluoroacetic acid, in the presence of acids, such as mineral acids, for example hydrochloric acid, hydrobromic acid or sulfuric acid, or carboxylic acids, for example acetic acid or trifluoroacetic acid, particularly preferably in the presence of acetic acid, especially preferably in the presence of trifluoroacetic acid, both as solvent and as acid, in a temperature range of from −20° C. to +60° C., particularly preferably from 0° C. to +30° C., giving the carboxylic acids (XIX).

In the fourth step [D], the carboxylic acids (XIX) are reduced in solvents such as ethers, for example diethyl ether, tetrahydrofuran or dioxane, or in chlorinated hydrocarbons such as methylene chloride or chloroform, or in mixtures thereof, particularly preferably in tetrahydrofuran, using boron compounds as reducing agents, for example borane or borane-dimethyl sulfide complex, in a temperature range of from −40° C. to +60° C., particularly preferably from −20° C. to +30° C., giving the hydroxyl compounds (XX).

In the fifth reaction step [E], the hydroxyl compounds (XX) are oxidized in solvents such as ethers, for example diethyl ether, dioxane or tetrahydrofuran, or in chlorinated hydrocarbons such as methylene chloride or chloroform, or in dimethyl sulfoxide or in mixtures thereof, particularly preferably in dichloromethane, using oxidizing agents such as pyridinium chlorochromate, chromium(VI) salts, dimethyl sulfoxide/pyridine/SO₃, catalytic amounts of tetraalkylammonium perruthenate in the presence of N-methylmorpholine and molecular sieve, dimethyl sulfoxide/oxalyl chloride/triethylamine, particularly preferably using pyridinium chlorochromate, catalytic amounts of tetraalkylammonium perruthenate in the presence of N-methylmorpholine oxide and molecular sieve or dimethyl sulfoxide/oxalyl chloride/triethylamine, if appropriate in the presence of bases, such as triethylamine, diisopropylamine, pyridine or dimethylaminopyridine, particularly preferably in the presence of triethylamine, in a temperature range of from −20° C. to +60° C., particularly preferably from 0° C. bis +30° C., giving the aldehydes (XXI).

The cyclic ketones (XVI) are either commercially available or preparable by customary routes known to the person skilled in the art, for example by Dieckmann condensation of the corresponding carboxylic acid diesters.

The 4-chloromethylbenzoic acid esters of 4-chlorosulfenylbenzoic acid esters to be reacted with the ketones (XVI), or the corresponding nitriles, are either commercially available or can be prepared by customary routes known to the person skilled in the art.

In the compounds shown in the above diagram of process C, the radicals $R^3$, $R^4$, o, r and Y have the same meanings as defined in claim 3.

By process C, it is possible to prepare aldehydes (II) in which X represents —CH₂—, Y represents —CH₂— or —S—, o represents 3, 4 or 5, A represents COOR⁴ and B represents CN, CH₂OOR⁹, CONR¹⁰R¹¹ or COOR⁸.

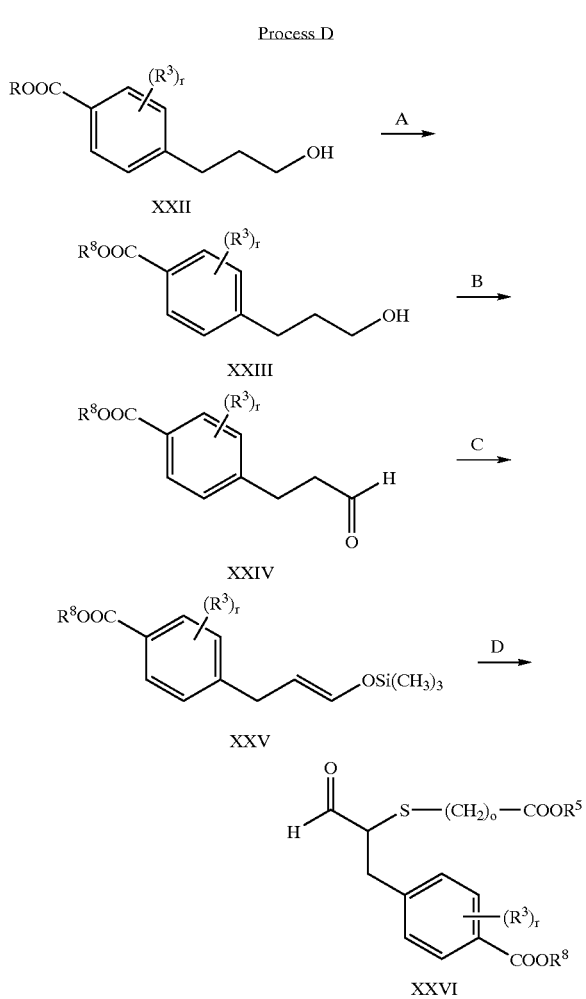

In the first reaction step [A] of this variant, the benzoic acid mixture (XXII) is converted in solvents such as alcohols, for example methanol, ethanol, propanol or isopropanol, or in water or in mixtures thereof, particularly preferably in methanol, in the presence of acids, such as mineral acids, for example hydrochloric acid, hydrobromic acid or sulfuric acid, or in carboxylic acids, such as acetic acid or trifluoroacetic acid, or, particularly preferably, in the presence of thionyl chloride, in a temperature range of from −40° C. to +60° C., particularly preferably from −20° C. to +40° C., into the esters (XXIII).

In the second reaction step [B], the esters (XXIII) are oxidized in solvents such as an ether, for example diethyl ether, tetrahydrofuran or dioxane, or in dimethyl sulfoxide, or in chlorinated hydrocarbons such as methylene chloride or chloroform, or in mixtures thereof, particularly preferably in methylene chloride, using oxidizing agents such as bromine-(VI) salts, pyridinium chlorochromate, dimethyl sulfoxide/oxalyl chloride or dimethyl sulfoxide/pyridine/SO$_3$, particularly preferably using dimethyl sulfoxide/oxalyl chloride, as oxidizing agent in the presence of bases such as triethylamine, diisopropylamine, pyridine, or dimethylaminopyridine, particularly preferably in the presence of triethylamine, in a temperature range of from −80° C. to +40° C., particularly preferably from −60° C. to +20° C., analogously to step E in process C, to the aldehydes (XXIV).

In the third reaction step [C] the aldehydes (XXIV) are converted in solvents such as hydrocarbons, for example benzene, toluene or xylene, or in dimethyl sulfoxide or in amides, such as dimethylformamide or hexamethylphosphoric triamide, or in mixtures thereof, particularly preferably in dimethylformamide, in the presence of bases such as triethylamine, diisopropylamine, pyridine or dimethylaminopyridine, particularly preferably in the presence of triethylamine, in a temperature range of 0° C. to +200° C., particularly preferably from +20° C. to +180° C., using trimethylsilyl chloride or triflate, into the silicon compounds (XXV).

In the fourth reaction step [D], these silicon compounds (XXV) are converted, using dimethyl 4,4'-dithiodibutyrate or dimethyl 3,3'-dithiodipropionate in the presence of sulfuryl chloride or chlorine or bromine in a solvent such as an ether, for example diethyl ether, tetrahydrofuran or dioxane, or in hydrocarbons such as benzene or toluene, or in chlorinated hydrocarbons such as methylene chloride or chloroform or in mixtures thereof, particularly preferably an ethylene chloride, if appropriate in the presence of bases such as triethylamine or diisopropylamine or pyridine, in a temperature range of from −80° C. to +20° C., particularly preferably from −70° C. to +0° C., into the aldehydes (XXVI).

Using this variant, it is possible to prepare compounds of the general formula (II) in which X represents S and, preferably Y represents CH$_2$ and o represents 2 or 3.

In the compounds shown in the above diagram of process D, the radicals R$^3$, R$^8$, r and o have the same meanings as defined in claim 3. The radical R represents any customary alcoholic component of an ester.

The benzoic acid esters of the formula (XXII) can be prepared by routes known to the person skilled in the art or are commercially available.

Process E

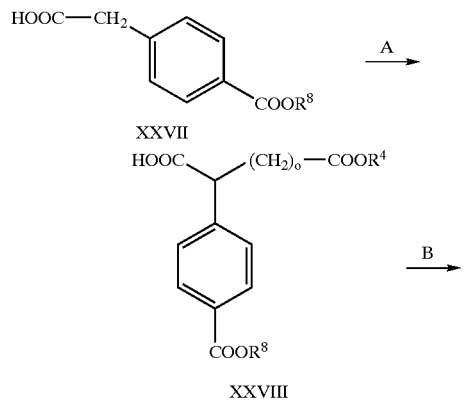

XXVII

XXVIII

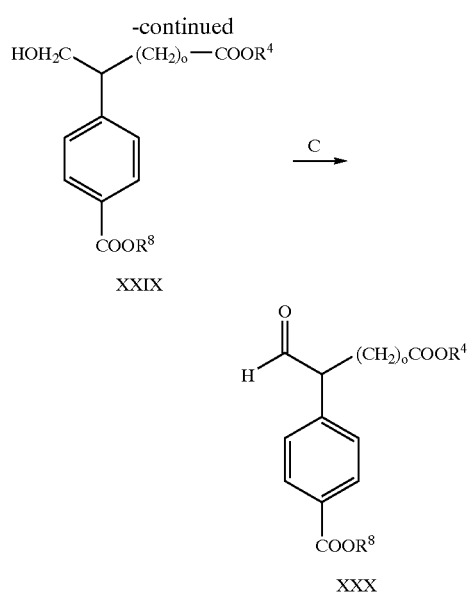

XXIX

XXX

In this variant, the benzoic acid derivative (XXVII) is converted in solvents such as ethers, for example diethyl ether, tetrahydrofuran, dioxane, diethylene glycol monomethyl ether or diethylene glycol diethyl ether, or in amides such as dimethylformamide or hexamethylphophoric triamide, in 1,3-dimethylimidazolidin-2-one or 1,3-dimethyltetrahydropyridin-2-one or in mixtures thereof, particularly preferably in tetrahydrofuran, in the presence of organometal compounds as base, for example organic lithium, sodium or potassium compounds, particularly preferably butyllithium, methyllithium, phenyllithium, sodium naphthalide, potassium naphthalide, lithium diisopropylamide or lithiumhexamethyldisilazane, especially preferably in the presence of lithium diisopropylamide, in a temperature range of from −80° C. to +60° C., particularly preferably from −50° C. to +30° C., into the compounds (XXVIII) which are subsequently, in a second reaction step [B], in solvents such as an ether, for example dimethyl ether, tetrahydrofuran or dioxane, or in chlorinated hydrocarbons such as methylene chloride or chloroform, or in mixtures thereof, particularly preferably in tetrahydrofuran, reduced using boranes as reducing agents, preferably using borane or borane-dimethyl sulfide complex, in a temperature range of from −40° C. to +60° C., preferably from −20° C. to +30° C., to the hydroxyl compounds (XXIX).

In the third reaction step [C], the hydroxyl compounds (XXIX) are oxidized in solvents such as an ether, for example diethyl ether, tetrahydrofuran or dioxane, or in chlorinated hydrocarbons such as methylene chloride or chloroform, or dimethyl sulfoxide, or in mixtures thereof, particularly preferably in dichloromethane, using oxidizing agents such as chromium(VI) salts, pyridinium chlorochromate, dimethyl sulfoxide/oxalyl chloride or dimethyl sulfoxide/pyridine/SO$_3$, particularly preferably pyridinium chlorochromate, if appropriate in the presence of bases such as triethylamine, diisopropylamine or pyridine, particularly preferably in the presence of triethylamine, in a temperature range of from −80° C. to +60° C., preferably from −60° C. to +30° C., analogously to step E in process C, to the aldehydes (XXX). The benzoic acid derivatives of the formula (XXVI) are commercially available or can be obtained in a customary manner known to the person skilled in the art.

Using this variant, it is possible to prepare compounds of the general formula (U) in which X represents CH$_2$ and, preferably, Y represents a direct bond and o represents 3 or 4.

In the compounds shown in the above diagram of process E, the radicals $R^4$, $R^5$ and o have the same meanings as defined in claim 3, but $R^4$ and $R^8$ may not represent COOH.

Processes F and G

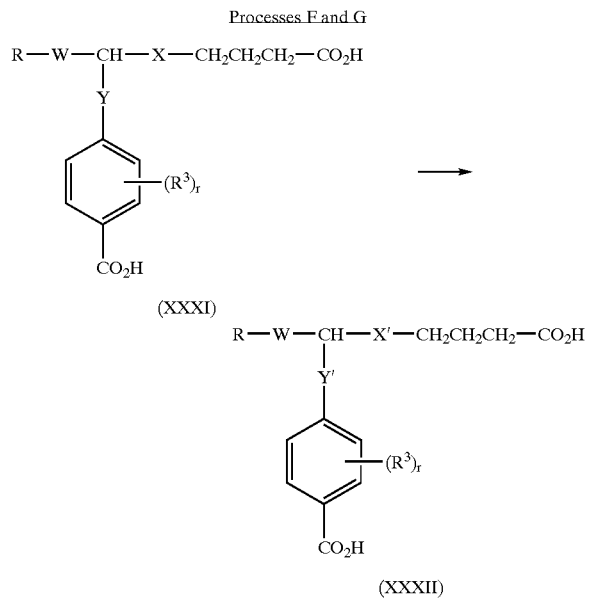

(XXXI)

(XXXII)

In this variant, the acid (XXXI) is reacted in solvents such as alcohols, water, acetone or acetonitrile with an oxidizing agent such as hydrogen peroxide, nitric acid, peracids, oxygen, ozone, organic peracids, potassium permanganate, potassium persulfate, sodium hypochlorite, hypochlorous acids, ruthenium tetraoxide, nitrous oxides, anodic oxidation or using a special mixture such as ozone in a normal temperature range of from −20° C. to +30° C., although even lower temperature ranges (−78° C.) may be necessary for substances which are relatively unreactive. The product of this process is the sulfone (XXII).

Using this variant, it is possible to prepare compounds of the general formula (D) in which X represents $CH_2$ or a direct bond and Y represents SO or $SO_2$ or X represents SO or $SO_2$ and Y represents $CH_2$ or a direct bond.

In the compounds shown in the above diagram of process F, the radicals $R^3$, W, X and Y and also r have the same meanings as defined in claim 3. X' and Y' represent radicals X and Y which are, if appropriate, modified in process F (i.e. $SO_2$). R represents the radical of the compounds of the general formula (I).

Process G

In this variant, the acid (XXXI) is reacted as in variant F/G, but using smaller amounts of oxidizing agents and/or at a lower temperature or using oxidizing agents such as hydroperoxides, manganese dioxide, selenium dioxide, peracids, chromic acid or iodosobenzene. The product of this process is the sulfoxide (XXXII).

In the compounds shown in the above diagram of process F, the radicals $R^3$, W, X and Y and also r have the same meanings as defined in claim 3. X' and Y' represent radicals X and Y which are, if appropriate, modified in process G (i.e. SO). R represents the radical of the compounds of the general formula (I).

Process H

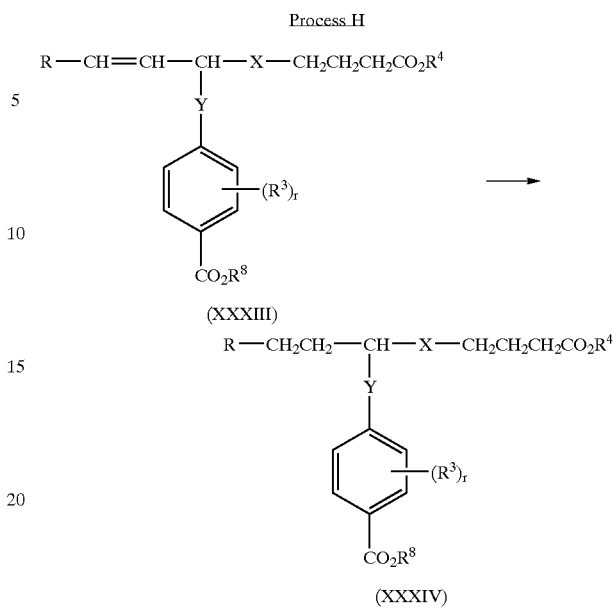

(XXXIII)

(XXXIV)

In this process, the acid (XXXI) is, in solvents such as alcohols, water, benzene, toluene, ethers such as dimethyl ether, tetrahydrofuran, dioxane, esters such as ethyl acetate, or in hydrocarbons such as hexane, or in amines such as triethylamine or in ammonia, reacted with a reducing agent such as hydrogen in the presence of a metal catalyst such as the oxides or soluble complexes of palladium, platinum, ruthenium or nickel, or with a metal such as lithium or sodium, or with hydrazine or arylaralkoxy-substituted hydrazines. The product of this reaction is the acid (XXXIV) in which W of the general formula (I) represents —$CH_2CH_2$— or $CH_2CH_2CH_2$—. The normal temperature range for this process is from −20° C. to +30° C.

In the compounds shown in the above diagram of process H, $R^3$, $R^4$, $R^8$, X, r and Y have the same meanings as defined in claim 3. R represents the radical of the compounds of the general formula (I), where R may contain an aryl radical, but not a double bond.

Process I

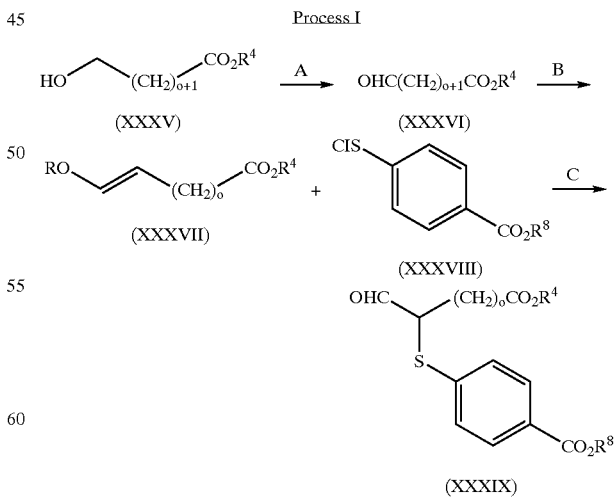

(XXXV) (XXXVI)

(XXXVII) (XXXVIII)

(XXXIX)

This process variant is analogous to process D and represents an alternative to process C for the case that Y=S. However, in contrast to process C, it can also be used for compounds in which o does not represent 3, 4 or 5 but an integer from 1 to 6.

The three steps are as follows:

[A] corresponds to step E of process C.
[B] corresponds to step C of process D, where R represents trimethylsilyl. R may optionally represent alkyl, for example methyl, and step B is optionally carried out by adding the aldehyde to a solution of the alkoxymethylene ylide (o is here increased by 1). The latter is generated as described above from an alkoxymethylenetriphenylphosphonium salt.
[C] corresponds to step D of process D.

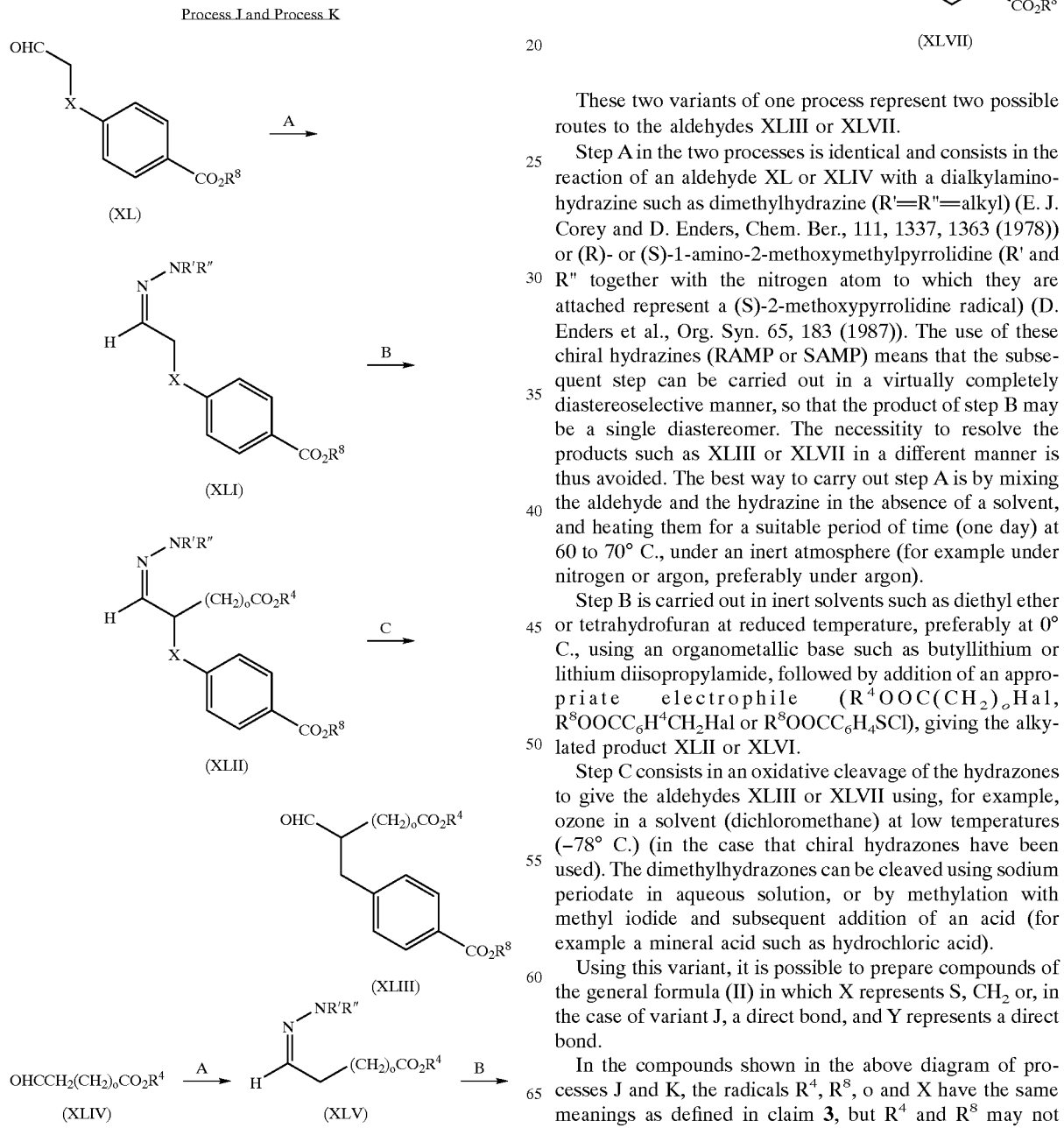

These two variants of one process represent two possible routes to the aldehydes XLIII or XLVII.

Step A in the two processes is identical and consists in the reaction of an aldehyde XL or XLIV with a dialkylaminohydrazine such as dimethylhydrazine (R'=R"=alkyl) (E. J. Corey and D. Enders, Chem. Ber., 111, 1337, 1363 (1978)) or (R)- or (S)-1-amino-2-methoxymethylpyrrolidine (R' and R" together with the nitrogen atom to which they are attached represent a (S)-2-methoxypyrrolidine radical) (D. Enders et al., Org. Syn. 65, 183 (1987)). The use of these chiral hydrazines (RAMP or SAMP) means that the subsequent step can be carried out in a virtually completely diastereoselective manner, so that the product of step B may be a single diastereomer. The necessity to resolve the products such as XLIII or XLVII in a different manner is thus avoided. The best way to carry out step A is by mixing the aldehyde and the hydrazine in the absence of a solvent, and heating them for a suitable period of time (one day) at 60 to 70° C., under an inert atmosphere (for example under nitrogen or argon, preferably under argon).

Step B is carried out in inert solvents such as diethyl ether or tetrahydrofuran at reduced temperature, preferably at 0° C., using an organometallic base such as butyllithium or lithium diisopropylamide, followed by addition of an appropriate electrophile ($R^4OOC(CH_2)_oHal$, $R^8OOCC_6H^4CH_2Hal$ or $R^8OOCC_6H_4SCl$), giving the alkylated product XLII or XLVI.

Step C consists in an oxidative cleavage of the hydrazones to give the aldehydes XLIII or XLVII using, for example, ozone in a solvent (dichloromethane) at low temperatures (−78° C.) (in the case that chiral hydrazones have been used). The dimethylhydrazones can be cleaved using sodium periodate in aqueous solution, or by methylation with methyl iodide and subsequent addition of an acid (for example a mineral acid such as hydrochloric acid).

Using this variant, it is possible to prepare compounds of the general formula (II) in which X represents S, $CH_2$ or, in the case of variant J, a direct bond, and Y represents a direct bond.

In the compounds shown in the above diagram of processes J and K, the radicals $R^4$, $R^8$, o and X have the same meanings as defined in claim 3, but $R^4$ and $R^8$ may not represent COOH.

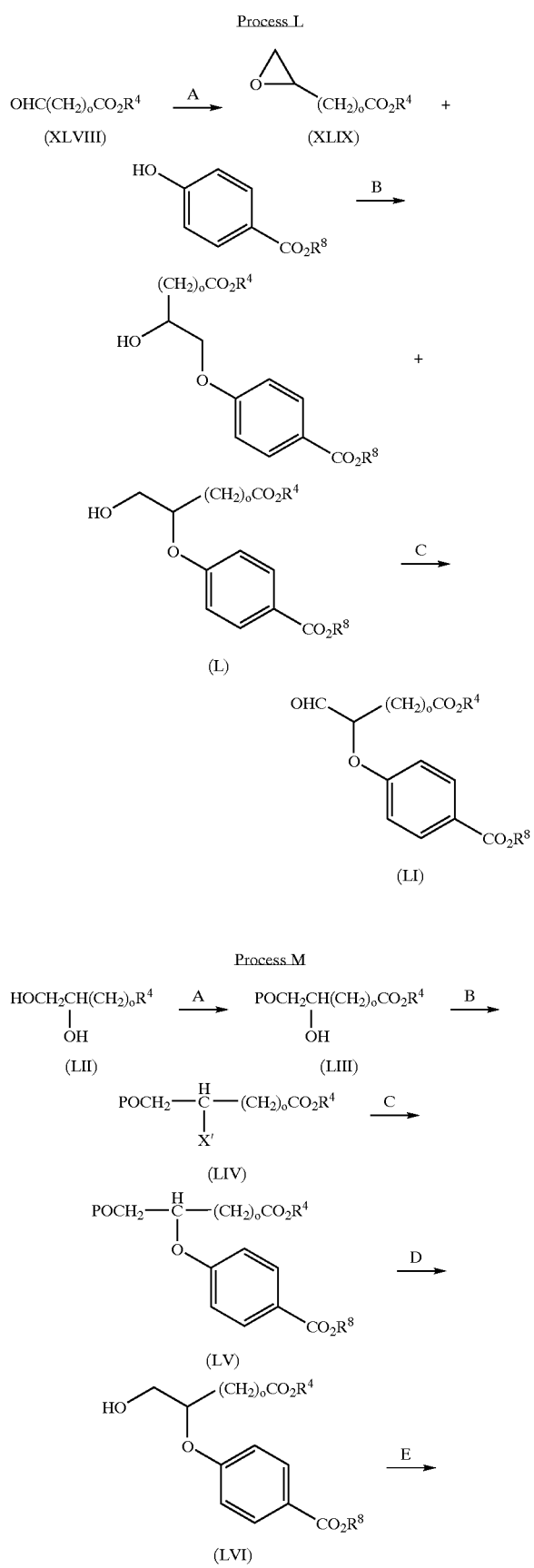

These processes illustrate two routes for preparing an aldehyde LI or LVII where X=O and Y=a direct bond.

In the first step of process L, the compound XLVIII is reacted with sulfonium ethylide (E. J. Corey et al., J. Am. Chem. Soc. 87, 1353 (1965)) in an inert solvent giving an epoxide XLIX.

The epoxide is subjected to a nucleophilic ring opening by reaction with a phenol in a solvent such as methanol, giving two regioisomers, from which the desired isomer L can be obtained in a simple manner by chromatography. The yield and ratio of the two isomers can be changed by varying the solvent and by using catalysts.

Step C is a simple oxidation as has already been described in detail in step C of process E.

In process M, a diol LII can optionally be protected by customary protective group techniques on the primary hydroxyl group and be converted into a tetrahydropyranyl ether (P=2-tetrahydropyranyl), t-butyldimethylsilyl ether (P=SiMe$_2$t-Bu) or t-butyldiphenylsilyl ether (P=SiPh$_2$t-Bu) LIII, the secondary hydroxyl group of which is not protected.

Step B of this process comprises the conversion of the free hydroxyl group into a customary leaving group X' such as, for example, a tosyl group or a halide radical, preferably a bromine or iodine radical, by routes already described in the above process.

In step C, the leaving group X' is replaced by a phenoxy group, essentially as described in step A of process B.

In step D, the protective group P is removed selectively by an appropriate customary prior-art process.

Step E is a simple oxidation, which has already been described above.

In the compounds shown in the above diagram of processes L and M, the radicals $R^4$, $R^8$ and o have the same meanings as defined in claim 3, but $R^4$ and $R^8$ may not represent COOH.

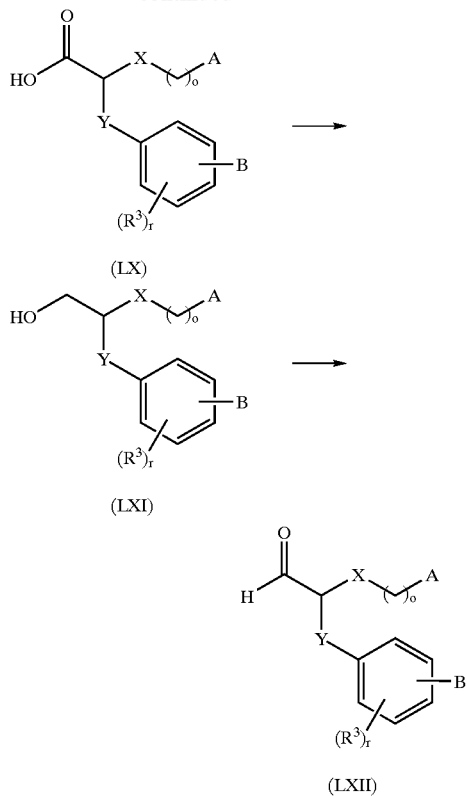

(LX)

(LXI)

(LXII)

In this process, a malonic acid diester (LVIII) where the alcoholic component R' used can be an allyl radical or lower alkyl radicals, such as methyl, ethyl, t-Bu or a benzyl radical) is converted by two successive reactions with corresponding electrophiles into a 2,2-disubstituted malonic acid diester (LIX). The malonic acid diester (LVIII) used as starting material can, for example, initially be reacted in the presence of a base, such as, for example, sodium hydride, triethylamine, potassium carbonate, sodium hydroxide, DABCO, potassium hydroxide, lithium diisopropylamide or sodium amide, preferably sodium hydride, with a corresponding electrophile, such as a corresponding halide, tosylate, mesylate or triflate, for example a halide such as ω-chloro- or ω-bromocarboxylic acid ester, for example methyl bromoacetate, in a solvent such as dioxane, at temperatures of from 0 to 50° C. In a second step, the resulting monosubstituted malonic acid diester derivative can be reacted by reaction with a corresponding electrophile, such as a corresponding halide, tosylate, mesylate or triflate, for example a 2-halogenobenzyl derivative, such as methyl 2-(bromo-methyl)benzoate, in the presence of a base, such as, for example, sodium hydride, triethylamine, potassium carbonate, sodium hydroxide, DABCO, potassium hydroxide, lithium diisopropylamide or sodium amide, preferably sodium hydride, in a solvent such as dimethylformamide, at temperatures of from 0 to 50° C. However, it is also possible to carry out the reactions with the two electrophiles in reverse order.

The resulting 2,2-disubstituted malonic acid diester derivative (LIX) can be converted by reaction with an acid such as, for example, hydrochloric acid, sulfuric acid or trifluoroacetic acid, or by reaction with a base such as potassium hydroxide, sodium hydroxide or lithium hydroxide, or by a palladium-catalyzed reaction, such as, for example, with formic acid in the presence of a Pd catalyst, preferably a Pd(II) catalyst, such as palladium(II) acetate, and a phosphine, such as triphenylphosphine, and a base, such as an amine, preferably triethylamine, in a solvent such as dioxane, at temperatures of from 20 to 120° C. by ester cleavage and subsequent decarboxylation at elevated temperatures into the corresponding carboxylic acid derivatives (LX).

These carboxylic acid derivatives (LX) can in turn be converted by reduction with customary reducing agents such as, for example, diisobutylaluminum hydride (DIBAL), lithium aluminum hydride or borohydrides, such as borane, in tetrahydrofuran, into the alcohols (LXI).

These alcohols (LXI) can then be oxidized using customary mild oxidizing agents such as Cr(VI) compounds, such as PDC or PCC, potassium permanganate, dimethyl sulfoxide/oxalyl chloride/triethalmine (Swern oxidation) or tetrapropylammonium perruthenate (TPAP) in the presence of a base such as N-methylmorpholine oxide and molecular sieve, or by Dess-Martin oxidation, to give the corresponding aldehydes (LXII).

In the compounds shown in the above diagram of process N, $R^3$, A, B, X, Y, r and have the same meanings as defined in claim 3, but A and B may not represent a free carboxyl function and X and Y may not represent O.

Process O

In the above processes, the preparation of β-disubstituted aldehydes having a p-alkoxycarbonyl group as one of the substituents in the β-position have been described. It is, of course, also possible to prepare compounds of the formula (II) in which the radical B is as defined in claim 3 and is located in a position ortho, meta or para to the radical Y. In these cases, the reactions described above are carried out with a corresponding ortho- or metadisubstituted compound instead of a para-disubstituted aryl compound. The tetrazolyl group (if A or B represents tetrazolyl) is here preferably introduced by using a corresponding monosubstituted nitrile, followed by reaction with sodium azide in the presence of a salt of a tertiary amine such as triethylamine or morpholine hydrochloride) in an inert solvent such as dimethylformamide at elevated temperatures. Amides or sulfonamides are preferably prepared from ester precursors which can be hydrolyzed selectively. The carboxylic acid group which is selectively released can then be reacted in an inert solvent with an aryl-, alkyl- or sulfonamide in the presence of a diimide such as dicyclohexanecarbodiimide. The carboxylic acid group which is selectively released can optionally be activated, for example by reaction with diphenylphoshinic acid chloride and then be reacted with a corresponding amine to give the desired amide.

Process P

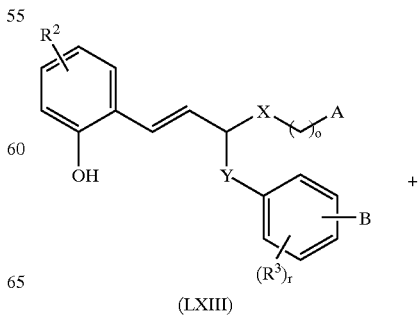

(LXIII)

+

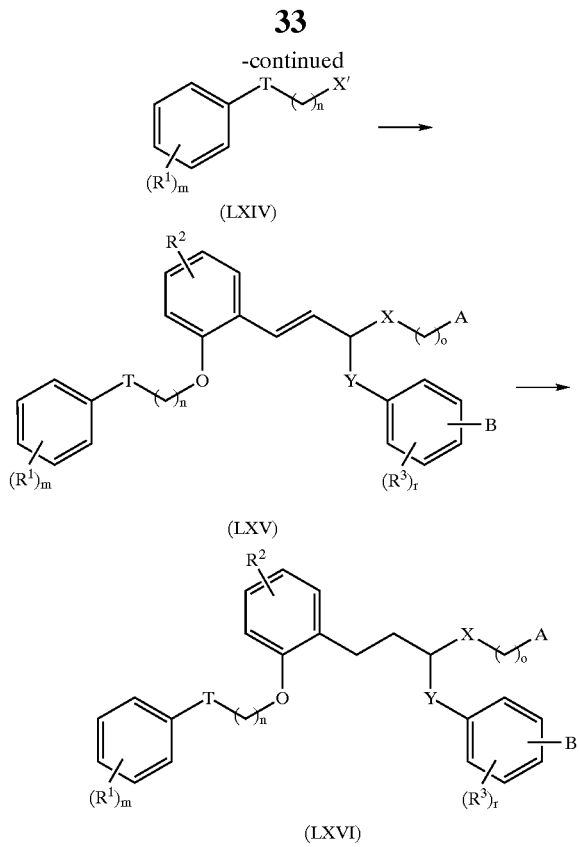

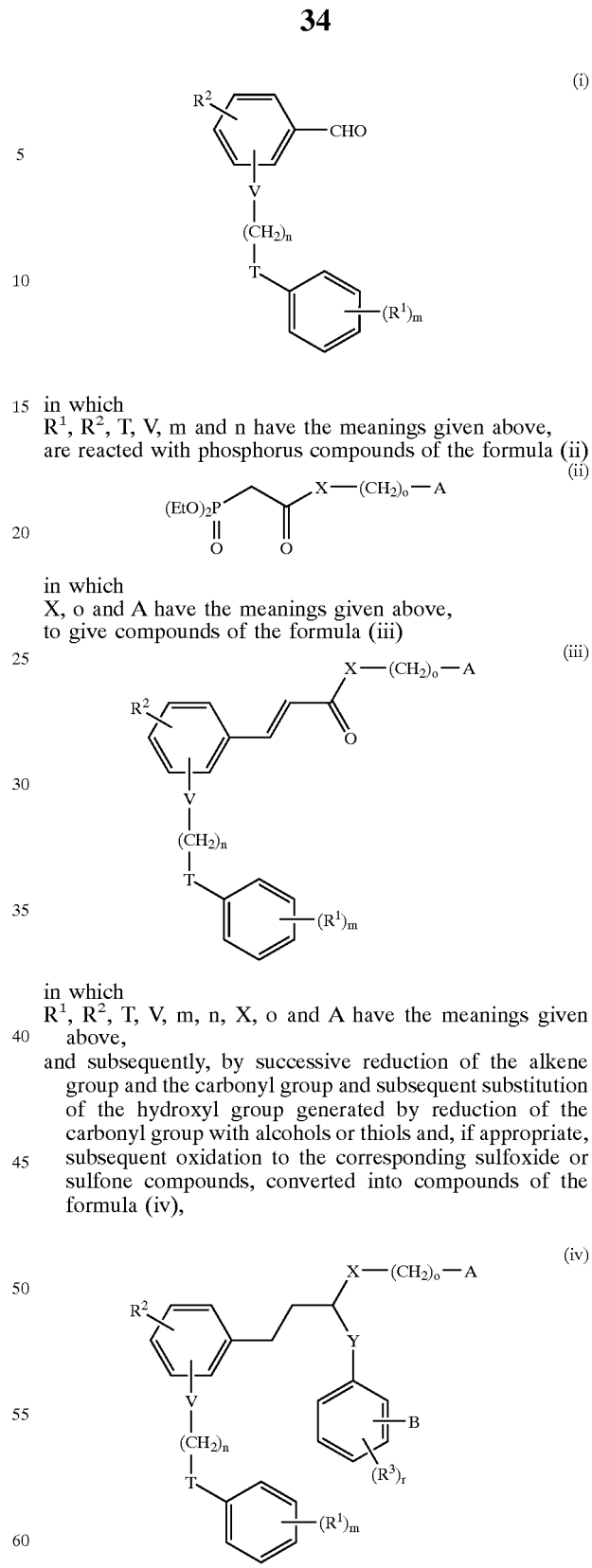

The compounds of the formula (I) can alternatively also be prepared by reacting corresponding aldehydes (II) with 2-hydroxybenzyltriphenylphosphonium compounds to give initially the alkenes (LXIII), followed by the synthesis of the side chain. The initial Wittig reaction can be carried out, for example, in an atmosphere of inert gas, such as argon, in a solvent such as tetrahydrofuran in the presence of a base such as n-butyllithium. The compounds of the formula (LXIII) which can be obtained in this manner can be converted by reaction with compounds (LXIV), which contain a leaving group X' such as, for example, a halogen atom, preferably a chlorine, bromine or iodine atom, or a tosylate, mesylate or triflate group, in the presence of a base such as potassium carbonate or cesium carbonate in a solvent such as acetonitrile into the compounds of the formula (LXV). The compounds of the formula (LXV) can be hydrogenated to compounds of the formula (LXVI), analogously to process H.

In particular in the case that the compound of the formula (LXIII) is to be attached to a benzyl group, the double bond is preferably initially hydrogenated analogously to process H, and the reaction at the free hydroxyl group is carried out afterwards.

By this process, compounds of the formula (I) are obtainable in which V represents an oxygen atom.

In the compounds shown in the above diagram of process P, the radicals $R^1$, $R^2$, $R^3$, A, B, T, X, Y, n, m, r and o have the same meanings as defined in claim 3, but A and B may not represent free carboxyl functions.

The compounds of the formula (I) according to the invention in which Y represents O, S, SO or $SO_2$ can be prepared by the process [β] according to the invention. Here, aldehydes of the formula (i)

in which
$R^1$, $R^2$, T, V, m and n have the meanings given above,
are reacted with phosphorus compounds of the formula (ii)

in which
X, o and A have the meanings given above,
to give compounds of the formula (iii)

in which
$R^1$, $R^2$, T, V, m, n, X, o and A have the meanings given above,
and subsequently, by successive reduction of the alkene group and the carbonyl group and subsequent substitution of the hydroxyl group generated by reduction of the carbonyl group with alcohols or thiols and, if appropriate, subsequent oxidation to the corresponding sulfoxide or sulfone compounds, converted into compounds of the formula (iv), in which
$R^1$, $R^2$, T, V, m, n, X, o, r, A, Y, B and and $R^3$ have the meanings given above.

The aldehydes of the formula (i) can be obtained, for example, from the alcohols used in processes A and B as intermediates, by customary oxidation reactions known to the person skilled in the art (cf., for example, J. March, Advanced organic Chemistry, 3$^{rd}$ ed., p. 1057 ff., Wiley).

The phosphorus compounds of the formula (ii) can be prepared, for example, by reacting alkanedicarboxylic acid derivatives, for example the corresponding monoesters, with phosphonoacetic acid derivatives, for example the corresponding diesters. However, it is also possible to synthesize these compounds from phosphites such as, for example, triethyl phosphite, using the corresponding α-halogenoketone derivatives (Arbuzov reaction, cf., for example, J. March, Advanced organic Chemistry, 3rd ed., p. 848 ff., Wiley).

The reaction of the compounds of the formula (i) with compounds of the formula (ii) is carried out in the presence of bases such as alkali metal hydrides, for example sodium hydride, alkali metal alkoxides, for example potassium t-butoxide, or in the presence of salts such as, for example, $MgCl_2$, and bases, such as amines, for example triethylamine, or Hünig base. The reaction is preferably carried out in organic solvents, particularly preferably in tetrahydrofuran, at room temperature or with gentle heating.

The resulting carbonyl compounds of the formula (iii) are reduced according to customary processes known to the person skilled in the art to the corresponding alcohols (cf., for example, J. March, Advanced organic Chemistry, 3rd ed., p. 809 ff., Wiley). The use of complex metal hydrides such as diisobutylaluminum hydride (DIBAL), NaBH or $NaBH_4/CeCl.7H_2O$ is particularly preferred. The reaction is preferably carried out in organic solvents such as, for example, alcohols, such as methanol, with cooling.

The olefinic double bond of the resulting hydroxyl compounds can be hydrogenated by customary processes known to the person skilled in the art (cf., for example, J. March, Advanced organic Chemistry, 3rd ed., p. 691 ff., Wiley). Preference is given to hydrogenations of hydrogen in the presence of a metal catalyst such as Pd/C or Raney-Nickel in an organic solvent such as, for example, ethyl acetate.

The radical Y-Ph($R^3$)-B can be introduced by several routes. It is possible, for example, to react the hydroxyl compound under Mitsunobu conditions (cf., O. Mitsunobu, Synthesis, 1981, 1–28) with corresponding alcohols, phenols or thiols. However, it is also possible to initially convert the hydroxyl group into a leaving group which can then be substituted by corresponding alcohols, phenols or thiols in the presence of a base such as, for example, DABCO, triethylamine, NaH, NaOH, KOH, LDA, sodium amide or particularly preferably, potassium carbonate. Leaving groups which are preferred according to the invention are halogen radicals, such as Cl, Br or I, which can be introduced by reacting the hydroxyl compound with, for example, $SOCl_2$, $SOBr_2$, $POCl_3$, $PCl_3$, $PCl_5$, $PBr_3$, etc., the tosylate radical, which can be introduced, for example, by reaction with tosyl chloride, the mesylate radical, which can be introduced, for example, by reaction with MsCl, or the triflate radical which can be introduced by reaction with, for example, $Tf_2O$ or TfCl.

The compounds according to the invention, in particular the compounds of the general formula (I), have an unforeseeable useful pharmacological activity spectrum.

The compounds according to the invention, in particular the compounds of the general formula (I), effect a relaxation of the vessels, inhibit platelet aggregation and lower the blood pressure, and also increase coronary blood flow. These effects are mediated via direct stimulation of soluble guanylate cyclase and intracellular cGMP increase.

They can therefore be employed in medicaments for the treatment of cardiovascular disorders, such as, for example, for the treatment of hypertension and cardiac insufficiency, stable and unstable angina pectoris, peripheral and cardiac vascular disorders, arrhythmias, for the treatment of thromboembolic disorders and ischemias, such as myocardial infarct, stroke, transitory and ischernic attacks, peripheral circulatory disorders, prevention of restenoses such as after thrombolysis therapy, percutaneous transluminal angioplasty (PTA), percutaneous transluminal coronary angioplasty (PTCA), bypass and also for the treatment of arteriosclerosis, fibrotic disorders, such as hepatic fibrosis or pulmonary fibrosis, asthmatic disorders and disorders of the urogenital system, such as, for example, prostate hypertrophy, erectile dysfunction, female sexual dysfunction and incontinence, and also for the treatment of glaucoma.

The compounds described in the present invention, in particular the compounds of the general formula (I), are also active compounds for controlling disorders in the central nervous system which are characterized by disturbances of the NO/cGMP system. In particular, they are suitable for eliminating cognitive deficits, for improving learning and memory performance and for treating Alzheimer's disease. They are also suitable for the treatment of disorders of the central nervous system, such as states of anxiety, tension and depression, sleeping disorders and sexual dysfunction caused by the central nervous system, and for regulating pathological eating disorders or disorders associated with the use of stimulants and drugs.

Furthermore, the active compounds are also suitable for regulating cerebral circulation, and they are therefore effective agents for controlling migraines.

They are also suitable for the prophylaxis and control of sequelae of cerebral infarct (Apoplexia cerebri) such as stroke, cerebral ischemias and skull-brain trauma. The compounds according to the invention, in particular the compounds of the general formula (I), can also be employed for controlling pain.

Additionally, the compounds according to the invention have antiinflammatory action and can therefore be employed as antiinflammatories.

Vaso Relaxant Action in Vitro

Rabbits are anaesthetized by intravenous injection of thiopental sodium or killed (about 50 mg/kg) and exsanguinated. The arteria saphena is removed and divided into 3 mm wide rings. The rings are individually mounted on in each case one triangular pair of hooks, open at the end, made of 0.3 mm strong special wire (Remanium®). Under a pretension, each ring is transferred into 5 ml organ baths containing a warm, carbogen-aerated Krebs-Henseleit solution at 37° C. having the following composition (mM): NaCl: 119; KCl: 4.8; $CaCl_2 \times 2H_2O$: 1; $MgSO_4 \times 7H_2O$: 1.4; KH2PO4: 1.2; $NaHCO_3$: 25; glucose: 10; bovine serum albumin: 0.001%. The contractility is detected using Statham UC2 cells, amplified and digitalized by means of A/D converters (DAS-1802 HC, Keithley Instruments Munich), and recorded in parallel on linear recorders. Contractions are induced by addition of phenylephrin.

After several (in general 4) control cycles, the substance to be investigated is added in each further passage in increasing dosage, and the height of the contraction achieved under the influence of the test substance is compared with the height of the contraction achieved in the last preliminary passage. From this, the concentration which is necessary in order to reduce the contraction achieved in the preliminary control by 50% ($IC_{50}$) is calculated. The standard administration volume is 5 μl. The proportion of DMSO in the bath solution corresponds to 0.1%.

The Results are shown in Table 1:

TABLE 1 vasorelaxant action in vitro

| Example | IC$_{50}$ (nM) |
|---|---|
| 12 | 112 |
| 13 | 2600 |
| 14 | 8.7 |
| 16 | 5 |
| 23 | 26 |
| 24 | 6200 |
| 34 | 0.35 |
| 35 | 1.7 |
| 40 | 41 |
| 41 | 2.8 |
| 44 | 7800 |
| 60 | 608 |

Stimulation of Recombinant Soluble Granulate Cyclase (sGC) in Vitro

The investigation on the stimulation of recombinant soluble guanylate cyclase (sGC) and the compounds according to the invention with and without sodium nitroprusside and with and without the heme-dependent sGC inhibitor 1H-1,2,4-oxadiazole-(4,3a)-quinoxalin-1-one (ODQ) were carried out by the method described in detail in the following literature reference: M. Hoenicka, E. M. Becker, H. Apeler, T. Sirichoke, H. Schroeder. R Gerzer and J.-P. Stasch: Purified soluble guanylyl cyclase expressed in baculovirus/Sf9 system: stimulation by YC-1, nitric oxide, and carbon oxide. J. Mol, Med. 77 (1999): 14–23.

Heme-free guanylate cyclase was obtained by adding Tween 20 to the sample buffer (final concentration 0.5%).

Activation of sGC by a test substance is stated as n-fold stimulation of basal activity.

The results are shown in Table 2.

TABLE 2

Stimulation of recombinant soluble guanylate cyclase (sGC) in vitro

| Ex. 16 concentration (µM) | Heme-containing sGC | | | Heme-free sGC | |
|---|---|---|---|---|---|
| | Basal | + SNP (0.1 µM) | + ODQ (10 µM) | Basal | + ODQ (10 µM) |
| 0 | 1 | 15 | 1 | 1 | 1 |
| 0.1 | 4 | 14 | 27 | 11 | 12 |
| 1.0 | 9 | 33 | 52 | 54 | 94 |
| 10 | 19 | 29 | 88 | 204 | 291 |

It can be seen from Table 2 that stimulation both of the heme-containing and of the heme-free enzyme is achieved. Furthermore, a combination of sGC stimulator and sodium nitroprusside (SNP), an NO donor, does not show any synergistic effect, i.e. the effect of SNP is not potentiated, as would be expected for sGC stimulators acting via a heme-dependent mechanism. In addition, the effect of the sGC stimulator according to the invention is not blocked by the heme-dependent inhibitor of soluble guanylate cyclase, ODQ. Thus, the results in Table 2 demonstrate the novel mechanism of action of the stimulators according to the invention of soluble guanylate cyclase.

The present invention includes pharmaceutical preparations which, in addition to non-toxic, inert, pharmaceutically acceptable excipients, contain the compounds according to the invention, in particular the compounds of the general formula (I), and also processes for the production of these preparations.

The active compounds can optionally be present in one or more of the excipients indicated above and also in microencapsulated form.

The therapeutically active compounds, in particular the compounds of the general formula (I), should be present in the abovementioned pharmaceutical preparations in a concentration from approximately 0.1 to 99.5, preferably from approximately 0.5 to 95, % by weight of the total mix.

In addition to the compounds according to the invention, in particular the compounds of the general formula (I), the abovementioned pharmaceutical preparations can also contain other pharmaceutically active compounds.

In general, it has proved advantageous both in human and in veterinary medicine to administer the active compound(s) according to the invention in total amounts of from approximately 0.5 to approximately 500, preferably 5 to 100, mgfkg of bodyweight every 24 hours, if appropriate in the form of several individual doses, to achieve the desired results. An individual dose contains the active compound(s) according to the invention preferably in amounts from approximately 1 to approximately 80, in particular 3 to 30, mg/kg of bodyweight.

EXAMPLES

The present invention is illustrated in more detail below using non-limiting, preferred examples. Unless indicated otherwise, all amounts given refer to percent by weight.

Abbreviations:
RT: room temperature
EA: ethyl acetate
BABA: n-butyl acetate/n-butanol/glacial acetic acid/phosphate buffer pH 6 (50:9:25.15; org. phase)
Mobile Phases for Thin-Layer Chromatography:
T1 E1: toluene/ethyl acetate (1:1)
T1 EtOH1: toluene/methanol (1:1)
C1 E1: cyclohexane/ethyl acetate (1:1)
C1 E2: cyclohexane/ethyl acetate (1:2)
Starting Materials

EX. I)

Methyl 5-(4-methoxycarbonylbenzyl)-6-oxohexanoate

Ia) 1-tert-Butyl 6-methyl 2-(4-methoxycarbonylbenzyl) hexane-1,6-dioate

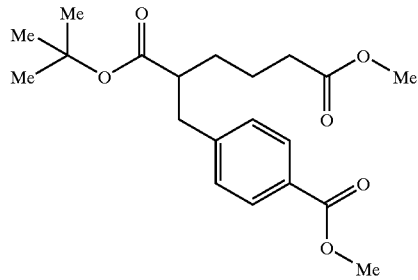

Under argon, 4.83 g (30 mmol) of tert-butyl 2-oxocyclopentanecarboxylate (prepared analogously to D. Henderson et al., Synthesis, 1983, 12, 996) are dissolved in 30 ml of dimethylformamide. A little at a time, 1.15 g (30 mmol) of sodium hydride (60%, oily suspension) are added at 0° C. After the evolution of hydrogen has ceased, a solution of 4.84 g (30 mmol) of methyl 4-chloromethylbenzoate and 4.35 g (35 mmol) of potassium iodide in 8 ml of dimethylformamide is added. The mixture is stirred at 0° C. for 30 min and then allowed to warm to room temperature. 2 ml of methanol are added and the mixture is stirred at room temperature. After the addition of ethyl acetate, the mixture is washed with sodium thiosulfate solution, twice with water and once with sodium chloride solution, dried and concentrated under reduced pressure.

Yield: 1.24 g (12.9% of theory)

$R_f$: 0.52(C1E1)

Ib) 2-[4-Methoxycarbonylbenzyl]-hexane-1,6-dioic acid 6-methyl ester

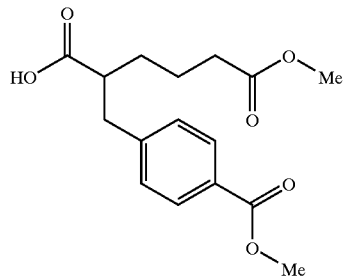

326 mg (0.89 mmol) of the t-butylester from Ia) are dissolved in 5 ml of trifluoroacetic acid and stirred at room temperature for one hour. The mixture is evaporated to dryness under reduced pressure. The residue is taken up in ethyl acetate and extracted twice with sodium bicarbonate solution. The aqueous phase is adjusted X to pH 4 using 1N hydrochloric acid and extracted twice with ethyl acetate, and the extract is dried using magnesium sulfate and concentrated under reduced pressure.

Yield: 154 mg (54.0% of theory)

$^1$H-NMR (300 MHz, CDCl$_3$): 7.90 (d, 2H), 7.20 (d, 2H), 3.90 (s, 3H), 3.65 (s, 3H), 3.10 (dd, 1H), 2.80 (m, 2H), 2.30 (m, 2H), 1.70–1.50 (m, 4H)

Ic) Methyl 6-hydroxy-5-(4-methoxycarbonylbenzyl) hexanoate

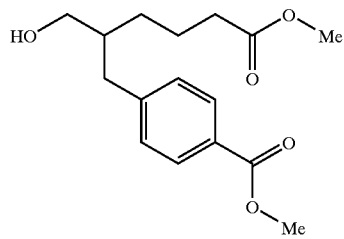

Under argon, 144 mg (0.49 mmol) of the acid from 1b) are dissolved in 2 ml of THF. At −1° C., 0.6 ml (0.6 mmol) of a solution of borane in THF (1M) are slowly added dropwise. The solution is stirred at 0° C. for 2 hours. After one hour, another 0.5 ml of the borane solution is added. Saturated sodium bicarbonate solution is carefully added dropwise, the mixture is extracted twice with ethyl acetate and the extracts are dried using magnesium sulfate and concentrated under reduced pressure.

Yield: 127 mg (92.4% of theory)

$^1$H-NMR (200 MHz, CDCl$_3$): 7.90 (d, 2H), 7.20 (d, 2H), 3.90 (s, 3H), 3.65 (s, 3H), 3.50 (m, 2H), 2.70 (m, 2H), 2.30 (m, 2H), 1.80–1.30 (m, 5H)

I): Methyl 5-(4-methoxycarbonylbenzyl)-6-oxohexanoate

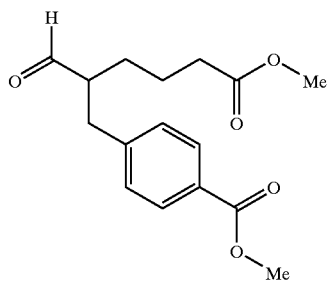

109 mg (0.37 mmol) of the alcohol from Ic) are dissolved in dichloromethane, and 0.5 g of molecular sieve 4A (activated at 125° C. under reduced pressure for 2h) and 65 mg (0.56 mmol) of N-methylmorpholine oxide are added. After 10 minutes, 6.5 mg (0.02 mmol) of tetrapropylammonium perruthenate (TPAP) are added. After 40 minutes, the reaction mixture is diluted with dichloromethane, filtered, washed once with water, dried with magnesium sulfate and concentrated under reduced pressure. The substance is chromatographed using the mobile phase C2:E1 and reacted further.

Yield: 34 mg (31.4% of theory)

EX. II)

Ethyl 6-(4-cyanobenzyl)-7-oxo-heptanoate

Ia) 1-tert-Butyl 7-ethyl 2-(4-cyanobenzyl)-heptane-1,7-dioate

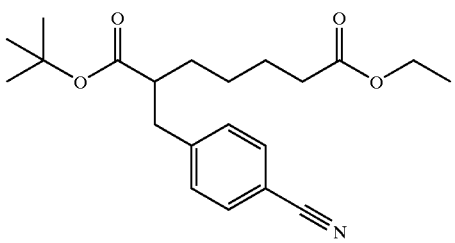

5.33 g (17.1 mmol) of tert-butyl 1-(4-cyanobenzyl)-2-oxbcyclohexanecarboxylate (prepared from tert-butyl 2-oxocyclohexanecarboxylate and 4-cyanobenzyl bromide using sodium hydride in benzene) and 1.91 g (17.1 mmol) of potassium tert-butoxide are dissolved in 50 ml of ethanol, and the solution is heated at reflux for 4 hours. The solution is cooled, 10 g of silica gel are added and the mixture is concentrated using a rotary evaporator. For purification, the substance is chromatographed on 120 g of silica gel 60 (particle size 0.040–0.063 mm) using the mobile phase C1:E1 1:1 to ethyl acetate.

Yield: 3.00 g (49.1% of theory)

$R_f$: 0.69 (EA)

IIb) 2-(4-Cyanobenzyl)-heptane-1,7-dioic acid 7-ethyl ester

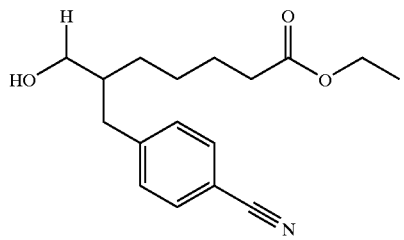

3.00 g (8.34 mmol) of the t-butyl ester from IIa) are reacted analogously to Example Ib). The crude acid is reacted further.

Yield: 3.15 g (crude)

$^1$H-NMR (400 MHz, CDCl$_3$): 7.70 (d, 2H), 7.40 (d, 2H), 4.20 (q, J=6 Hz, 2H), 3.00 (dd, 1H), 2.90 (dd, 1H), 2.70 (m, 1H), 2.30 (t, 2H), 1.70–1.30 (m, 6H), 1.20 (t, J=6 Hz, 3H)

IIc) Ethyl 6-(4-cyanobenzyl)-7-hydroxyheptanoate

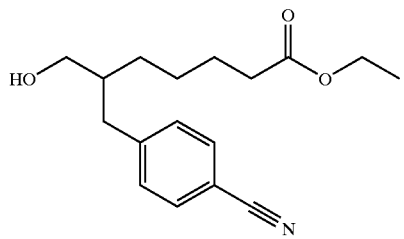

3.15 g of the crude acid from IIb) are reacted analogously to Example 1c).

Yield: 1.264 g (42.4% of theory over 2 step)

$^1$H-NMR (200 Kz, CDCl$_3$): 7.60 (d, 2H), 7.20 (d, 2H), 4.10 (q, J=6 Hz, 2H), 3.50 (m, 2H), 2.70 (m, 2H), 2.30 (t, 2H), 1.90–1.20 (m, 10H)

II) Ethyl 6-(4-cyanobenzyl)-7-oxo-heptanoate

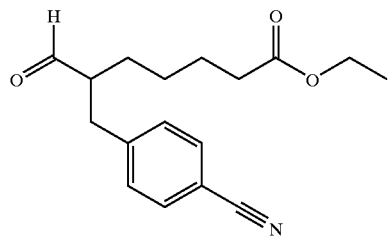

1.13 g (3.90 mmol) of the alcohol from IIc) are reacted analogously to Example Id).

Yield: 0.79 g (70.4% of theory)

$^1$H-NMR (200 MHz, CDCl$_3$): 9.60 (d, 1H), 7.60 (d, 2H), 7.20 (d, 2H), 4.10 (q, J=6 Hz, 2H), 3.10 (dd, 1H), 2.70 (m, 2H), 2.30 (t, 2H), 1.90–1.20 (m, 9H).

EX. III–XVI)
Triphenylphosphoniumbenzyl salts

IIIa) 2-Benzyloxybenzyl alcohol

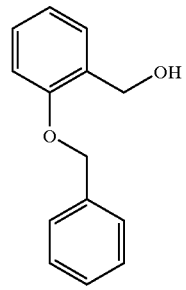

13.78 g (80.5 mmol) of benzyl bromide, 10.00 g (80.5 mmol) of 2-hydroxybenzyl alcohol and 11.13 g (80.5 mmol) of potassium carbonate in 270 ml of 2-propanol are heated at reflux overnight. The suspension is cooled, taken up in ethyl acetate, washed with 1N aqueous sodium hydroxide solution and water, dried over magnesium sulfate and concentrated under reduced pressure.

Yield: 15.15 g (87.8% of theory)

R$_f$(SiO$_2$, C4E1): 0.14

The following compounds were prepared analogously:

| Example | Formula | Yield (%) | R$_f$ Value |
|---|---|---|---|
| IVa (from phenethyl bromide) | | 81.9 | 0.56(C1E1) |
| Va (from phenyl-propyl bromide) | | 99.1 | 0.57(C1E1) |

-continued

| Example | Formula | Yield (%) | $R_f$ Value |
|---|---|---|---|
| VIa (from phenbutyl bromide) | | crude | 0.58(C1E1) |
| VIIa (from phenyl-pentyl bromide) | | 59.6 | 0.57(C1E1) |
| VIIIa (from phenylhexyl bromide) | | 33.1 | 0.61(C1E1) |
| IXa (from 3-phenoxy-1-bromo-propane) | | 93.9 | 0.50(C1E1) |
| Xa (from 4-phenoxy-1-bromo-butane) | | 91.3 | 0.49(C1E1) |

III) 2-(Benzyloxy)benzyltriphenylphosphonium bromide

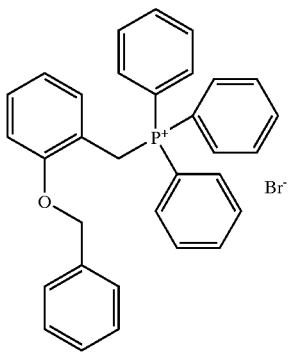

15.15 g (70.7 mmol) of the benzyl alcohol IIIa and 21.86 g (63.7 mmol) of triphenyl-phosphonium hydrobromide in 240 ml of acetonitrile are heated at reflux for 5 hours. The solvent is evaporated under reduced pressure, and diethyl ether is then added. The solid is filtered and dried under reduced pressure.

Yield: 32.24 g (84.4% of theory)

$^1$H-NMR (200 MHz, d$^6$-DMSO): 7.80–6.60 (m, 24H), 5.20 (d, J=15 Hz, 2H), 4.40 (s, 2H)

The following compounds were prepared analogously:

| Example | Formula | Yield | ¹H-NMR Data |
|---|---|---|---|
| IV (analogously from 2-hydroxy-4-methylbenzyl alcohol and benzyl bromide) | | 86.2 | 1H-NMR(200MHz, CDCl₃): 7.80–7.00(m, 21H), 6.65(d, 1H), 6.50(s, 1H), 5.20(d, J=15Hz, 2H), 4.45(s, 2H), 2.30(d, 3H) |
| V (analogously from 2-hydroxybenzyl alcohol and 2-chlorobenzyl bromide) | | 77.8 | ¹H-NMR(200MHz, d⁶-DMSO): 7.80–6.80 (m, 23H), 5.00(d, J=15Hz, 2H), 4.60(s, 2H) |
| VI (analogously from 2-hydroxybenzyl alcohol and 2,6-dichlorobenzyl bromide) | | 77.4 | ¹H-NMR(200MHz, CDCl₃): 7.80–6.80(m, 22H), 5.25(d, J=15Hz, 2H), 4.90(s, 2H) |
| VII (from IVa) | | 74.6 | ¹H-NMR(200MHz, CDCl₃): 7.80–7.00(m, 22H), 6.80(t, 1H), 6.60(d, 1H), 5.20(d, J=15Hz, 2H), 3.60(t, 2H), 2.70(t, 2H) |

-continued

| Example | Formula | Yield | ¹H-NMR Data |
|---|---|---|---|
| VIII (from Va) | | 89.9 | ¹H-NMR(200MHz, CDCl$_3$): 7.80–7.10(m, 22H), 6.80(t, 1H), 6.55(d, 1H), 5.70(d, J=15Hz, 2H), 3.35(t, 2H), 2.60(t, 2H), 1.70 (m, 2H) |
| IX (from VIa) | | 83.7 | ¹H-NMR(200MHz, CDCl$_3$): 7.80–7.10(m, 22H), 6.80(t, 1H), 6.55(d, 1H), 5.30(d, J=15Hz, 2H), 3.40(t, 2H), 2.60(t, 2H), 1.70–1.50(m, 4H) |
| X (from VIIa) | | 90.9 | ¹H-NMR(200MHz, CDCl$_3$): 7.80–7.10(m, 22H), 6.65(t, 1H), 6.50(d, 1H), 5.30(d, J=15Hz, 2H), 3.35(t, 2H), 2.60(t, 2H), 1.70–1.20(m, 6H) |
| XI (from VIIIa) | | 84.0 | ¹H-NMR(200MHz, d⁶-DMSO): 7.80–6.30 (m, 24H), 4.90(d, J=15Hz, 2H), 3.40(m, 2H), 2.60(m, 2H), 1.60–1.20(m, 8H) |
| XII (from IXa) | | 90.7 | ¹H-NMR(400MHz, d⁶-DMSO): 7.80–6.80 (m, 24H), 5.00(d, J=15Hz, 2H), 3.90(t, 2H), 3.60(t, 2H), 1.75 (m, 2H) |

-continued

| Example | Formula | Yield | ¹H-NMR Data |
|---|---|---|---|
| XIII (from Xa) | | 93.0 | ¹H-NMR(400MHz, d⁶-DMSO): 7.80–6.80 (m, 24H), 4.90(d, J=15Hz, 2H), 3.90(t, 2H), 3.50(t, 2H), 1.65 (m, 2H), 1.50(m, 2H) |
| XIV (analogously from 2-hydroxybenzyl alcohol and 4-bromobenzyl bromide) | | 95 | ¹H-NMR(200MHz, d⁶-DMSO): 8.00–6.70 (m, 23H), 5.00(d, J=15Hz, 2H), 4.60(s, 2H) |
| XV (analogously from 2-(2-phenylethyl)-benzyl alcohol, which is commercially available) | | 98.6 | ¹H-NMR(200MHz, d⁶-DMSO): 8.00–6.80 (m, 24H), 5.00(d, J=15Hz, 2H), 2.60(m, 2H), 2.20(m, 2H) |
| XVI (analogously from 2-(2-benzyl)-benzyl alcohol, which is commercially available) | | 97.0 | ¹H-NMR(200MHz, CDCl₃): 7.90–6.70(m, 24H), 5.30(d, J=15Hz, 2H), 3.20(s, 2H) |

| Example | Formula | Yield | ¹H-NMR Data |
|---|---|---|---|
| XVII (from 2-(4-methoxyphenyl-ethyl)benzoic acid via reduction with LiAlH₄) | 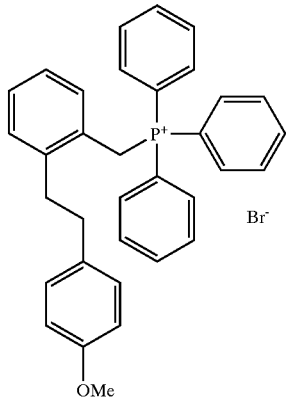 | 99.5 | ¹H-NMR(300MHz, d⁶-DMSO): 7.90–6.80 (m, 23H), 4.90(d, J=15Hz, 2H), 3.70(s, 3H) |

EX. XVIII 3-((4-Phenylbutoxy)phenethyl) triphenylphosphonium 4-methyl-benzenesulfonate XVIIIa: 2-(3(4-Phenylbutoxy)phenyl)ethanol

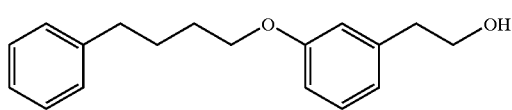

10.00 g (70 mmol) of 2-(3-hydroxyphenyl)ethanol, 15.42 g (70 mmol) of 4 phenylbutyl bromide and 10.00 g (70 mmol) of potassium carbonate in 45 ml of 2-propanol are heated at reflux overnight. The suspension is cooled, taken up in ethyl acetate, washed with 1N aqueous sodium hydroxide solution and water, dried over magnesium sulfate and concentrated under reduced pressure.

Yield: 14.8 g (75.7% of theory)
$R_f$(SiO₂, C1E1): 0.40

XVIIIb: 3-(4-Phenylbutoxy)phenethyl 4-methylbenzenesulfonate

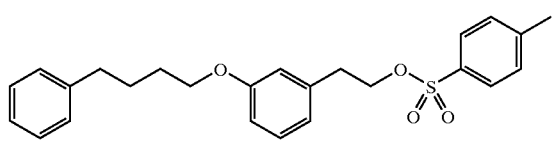

14.47 g (53.5 mmol) of 2-(3-(4-phenylbutoxy))ethanol from XVIIIa is dissolved in 50 ml and 35 ml of pyridine, and the mixture is stirred at room temperature for 30 min. The solution is cooled to −10° C., and 12.20 g (64.2 mmol) of 4-toluenesulfonyl chloride are added. The mixture is stirred at 0° C. for 2.5 hours, ethyl acetate and water are added, the phases are separated and the aqueous phase is extracted once with ethyl acetate. The combined organic phases are washed once with water, twice with 0.5N hydrochloric acid and once with sodium bicarbonate solution, dried over magnesium sulfate and concentrated under reduced pressure.

Yield: 21.59 g (95.0% of theory)
$R_f$(SiO₂, C1E1): 0.53

XVIII: 3-((4-Phenylbutoxy)phenethyl) triphenylphosphoniun 4-methylbenzenesulfonate

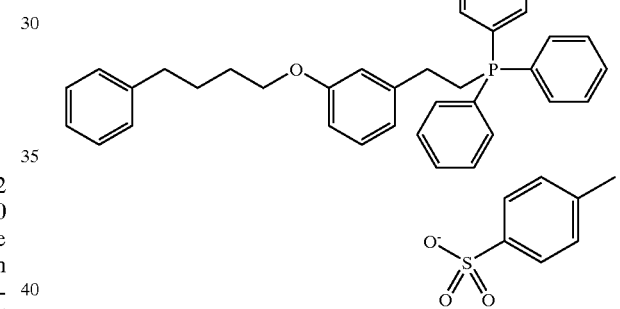

21.42 g (50.5 mmol) of the tosylate from XVIIIb and 13.20 g (50.5 mmol) of triphenylphosphine in 150 ml of acetonitrile are heated at reflux for 5 days. The solvent is evaporated under reduced pressure.

Yield: 34.8 g (100.0% of theory)
$R_f$(SiO₂, BABA): 0.52

EX. XIX–XXVI

Preparation of aldehydes of the formula (II) from malonic esters

XIXa: 1,1-Diallyl 2-methyl 1,1,2-ethanetricarboxylate

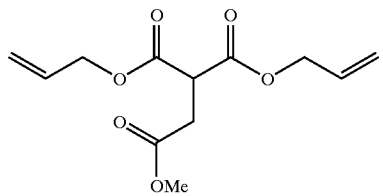

At 5° C., 1.18 g (49.03 mmol) of sodium hydride were added a little at a time to a solution of 12.04 g (65.4 mmol)

of bisallyl malonate in 700 ml of dry dioxane. The mixture was stirred until the evolution of gas had ended, the cooling bath was replaced by warm water (~40° C.) and the mixture was stirred for 30 min. A solution of 5.00 g (32.7 mmol) of methyl bromoacetate in 100 ml of dioxane was then added dropwise, and the mixture was stirred at RT (monitored by TLC, cyclohexane/EA 20:1). The precipitate that had formed was filtered off, the solvent was removed and the residue was taken up in water. The mixture was extracted three times with diethyl ether, the combined organic phases were dried over $Na_2SO_4$ and the solvent was removed. The product was purified by flash chromatography on silica gel (cyclohexane/EA 10:1).

Yield: 6.33 g (75.6%) of a colorless liquid.

$^1$H NMR (300 MHz, $CDCl_3$):

δ=2.94 (d, J=7.4 Hz, 2H), 3.68 (s, 3H), 3.90 (t, J=7.4 Hz, 1H), 4.62–4.67 (m, 4H), 5.21–5.36 (m, 4H), 5.81–5.95 (m, 2H).

The following compounds were prepared analogously using the corresponding bromocarboxylic esters.

XIXb: 2,2-Diallyl 1-methyl 3-[2-(methoxycarbonyl)phenyl]-1,1,2-propanetricar-boxylate

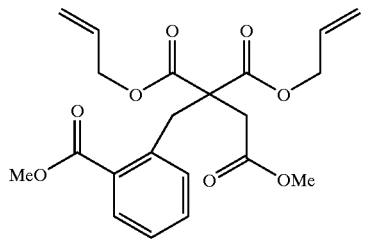

A little at a time, 49.2 mg (1.99 mmol) of sodium hydride were added to a solution of 510.0 mg (1.99 mmol) of 2-methyl 1,1-di(2-propenyl) 1,1,2-ethanetricarboxylate from Ex. XIXa in 5 ml of DMF. After the evolution of gas had ceased, stirring was continued for 20 min. A solution of 844.3 mg (2.99 mmol) of methyl 2-(bromomethyl)-benzoate in 6 ml of DMF was then added, and the mixture was stirred overnight. Water was added and the mixture was extracted three times with diethyl ether, the combined organic phases

| Example | Structure | Yield [%] | $^1$H-NMR Data |
|---|---|---|---|
| XXa | 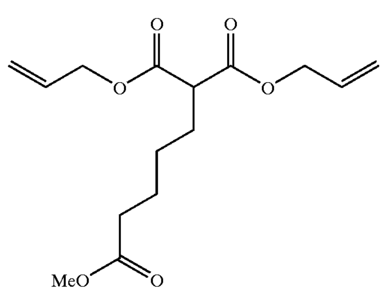 | 40.1 | $^1$H NMR(300MHz, $CDCl_3$): δ=1.37–1.49(m, 2H), 1.58–1.78(m, 2H), 1.87–2.03(m, 2H), 2.33(t, J=5.5Hz, 2H), 3.41(t, J=8.0Hz, 1H), 3.68(s, 3H), 4.60–4.68(m, 4H)5.21–5.40 (m, 4H), 5.79–6.02(m, 2H). |
| XXIa | | 82.8 | $^1$H NMR(400MHz, $CDCl_3$): δ=1.30–1.41(m, 4H), 1.62 (quint, J=7.3Hz, 2H), 1.92 (q, J=7.3Hz, 2H), 2.29(t, J= 7.3Hz, 2H), 3.39(t, J=7.6 Hz, 1H), 3.66(s, 3H), 4.63 (d, J=5.6Hz, 4H), 5.24 (ddd, J=10.3Hz, J=1.4Hz, J=0.9Hz, 2H), 5.32(ddd, J= 17.4Hz, J=1.6Hz, J=1.4 Hz), 2H), 5.83–5.97(m, 2H). | were dried over Na$_2$SO$_4$ and the solvent was removed. The product was purified chromatographically (20 g of silica gel, cyclohexane/EA 10:1).

Yield: 680.0 mg (84.5%) of a colorless liquid.

$^1$H NMR (300 MHz, CDCl$_3$):

δ=2.87 (s, 2H), 3.66 (s, 3H), 3.86 (s, 3H), 3.94 (s, 2H), 4.57–4.62 (m, 4H), 5.21 (dq, J=10.5 Hz, J=2.7 Hz, 2H), 5.28 (dq, J=17.2 Hz, J=3.0 Hz, 2H), 5.78–5.92 (m, 2H), 7.18–7.43 (m, 3H), 7.85 (dd, J=7.6 Hz, J 1=Hz, 1H).

The following compounds were prepared analogously:

| Example | Structure | Yield [%] | $^1$H-NMR Data |
|---|---|---|---|
| XXb (from XIXa and 3-cyanobenzyl chloride) | | 62.9 | $^1$H-NMR(300MHz, CDCl$_3$): δ=2.87(s, 2H), 3.45(s, 2H), 3.71(s, 3H), 4.65(d, J=5.9 Hz, 4H), 5.25–5.37(m, 4H), 5.81–5.95(m, 2H), 7.36–7.57(m, 4H). |
| XXIb (from XIXa and 2-cyanobenzyl chloride) | | 82.5 | $^1$H-NMR(300MHz, CDCl$_3$): δ=2.94(s, 2H), 3.70(s, 5H), 4.65–4.70(m, 4H), 5.24(dq, J=10.4Hz, J=2.6Hz, 2H), 5.32(dq, J=17.2Hz, J=3.0 Hz, 2H), 5.81–5.96(m, 2H), 7.24–7.65(m, 4H) |
| XXIIb (from XIXa and 3-methoxycarbonylbenzyl chloride) | | 89.5 | $^1$H-NMR(300MHz, CDCl$_3$): δ=2.87(s, 2H), 3.47(s, 2H), 3.71(s, 3H), 3.90(s, 3H), 4.63–4.68(m, 4H), 5.22–5.37 (m, 4H), 5.83–5.96(m, 2H), 7.27–7.38(m, 2H), 7.77(bs, 1H), 7.91(dt, J=7.4Hz, J=1.7Hz, 1H). |
| XXIIIb (from XXa and 2-cyanobenzyl chloride) | | 45.2 | $^1$H-NMR(300MHz, CDCl$_3$): δ=1.34–1.45(m 2H), 1.60–1.71(m, 2H), 1.82–1.93(m, 2H), 2.32(t, J=7.4Hz, 2H), 3.52(s, 2H), 3.67(s, 3H), 4.56–4.70(m, 4H), 5.21–5.34 (m, 4H), 5.79–5.94(m, 2H), 7.25–7.66(m, 4H). |

| Example | Structure | Yield [%] | $^1$H-NMR Data |
|---|---|---|---|
| XXIVb (from XXa and 3-cyanobenzyl chloride) | 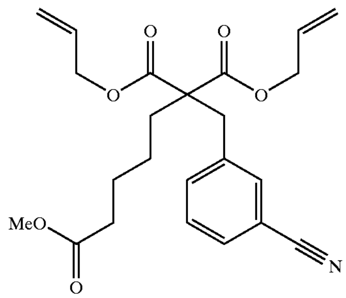 | 49.5 | $^1$H-NMR(300MHz, CDCl$_3$): δ=1.26–1.41(m, 2H), 1.59–1.69(m, 2H), 1.77–1.88 (m, 2H), 2.32(t, J=7.2Hz, 2H), 3.27(s, 2H), 3.68(s, 3H), 4.56–4.66(m, 4H), 5.22–5.38(m, 4H), 5.79–5.93(m, 2H), 7.33–7.57(m, 4H). |
| XXVb (from XXa and 3-methoxy-carbonylbenzyl chloride) | 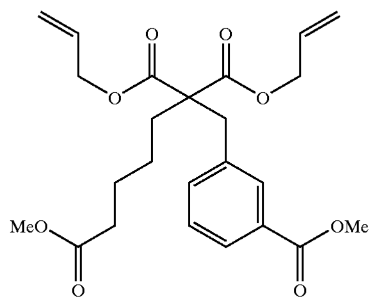 | 53.5 | $^1$H-NMR(300MHz, CDCl$_3$): δ=1.29–1.43(m, 2H), 1.64 (quint, J=7.2Hz, 2H), 1.75–1.86(m, 2H), 2.32(t, J=7.4 Hz, 2H), 3.30(s, 2H), 3.67(s, 3H), 3.90(s, 3H), 4.58–4.66 (m, 4H), 5.19–5.38(m, 4H), 5.79–5.96(m, 2H), 7.24–7.38(m, 2H), 7.73–7.80(m, 1H), 7.87–7.94(m 1H). |
| XXVIb (from XXa and 2-methoxy-carbonylbenzyl chloride) | 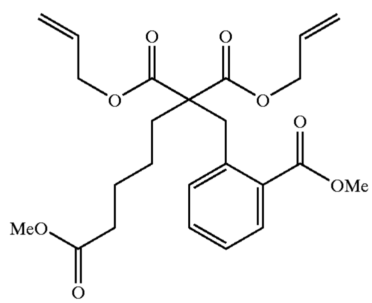 | 56.5 | $^1$H-NMR(300MHz, CDCl$_3$): δ=1.23–1.37(m, 2H), 1.60 (quint, J=7.6Hz, 2H), 1.77–1.87(m, 2H), 2.29(t, J=7.7 Hz, 2H), 3.65(s, 3H), 3.76(s, 2H), 3.87(s, 3H), 4.42–4.60 (m, 4H), 5.13–5.28(m, 4H), 5.70–5.86(m, 2H), 7.22–7.31(m, 2H), 7.33–7.41(m, 1H), 7.75–7.82(m, 1H). |

XIXc: 4-Methoxy-[2-(methoxycarbonyl)benzyl]-4-oxobutanoic acid

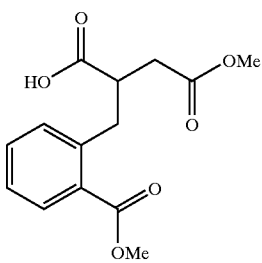

A solution of 504 mg (4.98 mmol) of triethylamine and 177 mg (3.77 mmol) of formic acid in 2 ml of dioxane was added to a solution of 610 mg (1.51 mmol) of 1-methyl 2,2-di(2-propenyl) 3-[2-(methoxycarbonyl)phenyl]-1,2,2-propanetri-carboxylate from Ex. XIXb, 32 mg (0.12 mmol) of triphenylphosphine and 7.0 mg (3.0 mmol) of palladium (II) acetate in 6 ml of dioxane. The mixture was heated at 100° C. for 2 h and then stirred at room temperature for a further 16 h. The solvent was removed and the residue was filtered through silica gel (cyclohexane/ethyl acetate 10:1 to elute the byproducts, cyclohexane/ethyl acetate/acetic acid 5:1:1 to elute the product).

Yield: 418 mg (98.8%) of a slightly yellowish oil $^1$H-NMR (300 MHz, CDCl$_3$):

δ=2.48 (dd, J=16.8 Hz, J=4.1 Hz, 1H), 2.75(dd, J=16.8 Hz, J=9.3 Hz, 1H), 3.08 (dd, J=12.9 Hz, J=8.3 Hz, 1H), 3.18–3.28 (m, 1H), 3.51 (dd, J=12.9 Hz, J=5.9 Hz, 1H), 3.63 (s, 3H), 3.92 (s, 3H), 7.22–7.71 (m, 3H), 7.98 (d, J=7.7 Hz, 1H).

The following compounds were prepared analogously:

| Example | Structure | Yield [%] | ¹H-NMR Data |
|---|---|---|---|
| XXc (from XXb) | 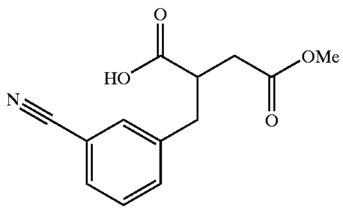 | 20.1 | ¹H-NMR(300MHz, CDCl₃): δ=2.49(dd, J= 16.7Hz, J=5.5Hz, 1H), 2.69(dd, J=16.7Hz, J= 7.7Hz, 1H), 2.89(dd, J= 13.2Hz, J=6.8Hz, 1H), 3.07–3.24(m, 2H), 3.68(s, 3H), 7.37–7.58(m, 4H), 10.05(bs, 1H). |
| XXIc (from XXIb) | 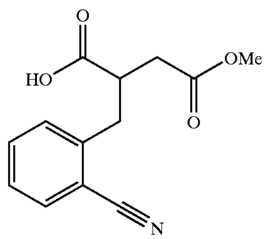 | 93.9 | ¹H-NMR(300MHz, CDCl₃): δ=2.45–2.59(m, 1H), 2.69–2.83(m, 1H), 3.04–3.17(m, 1H), 3.22–3.43(m, 2H), 3.67(s, 3H), 7.29–7.73(m, 4H), 8.03 bs, 1H). |
| XXIIc (from XXIIb) | 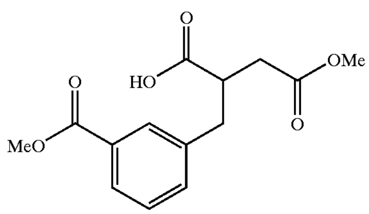 | 74.3 | ¹H-NMR(300MHz, CDCl₃): δ=2.37–2.45(m, 1H), 2.63–2.72(m, 1H), 2.79–2.91(m, 1H), 3.12–3.25(m, 2H), 3.65(s, 3H), 3.90(s, 3H), 7.14–7.93(m, 4H), 8.02(bs, 1H). |
| XXIIIc (from XXIIIb) | 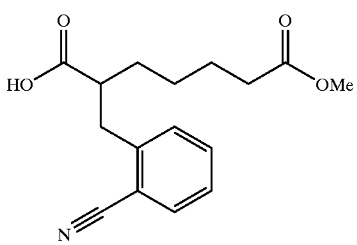 | 75.7 | ¹H-NMR(300MHz, CDCl₃): δ=1.34–1.82(m, 6H), 2.31(t, J=7.6Hz, 2H), 2.84(bs, 1H), 2.99–3.21(m, 2H), 3.66(s, 3H), 7.28–7.66(m, 4H). |
| XXIVc (from XXIVb) | 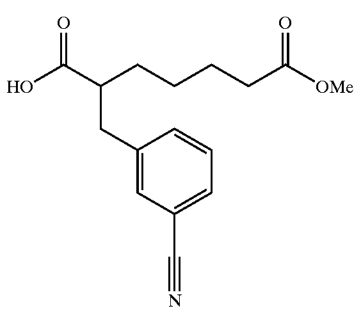 | 57.3 | ¹H-NMR(300MHz, CDCl₃): δ=1.31–1.77(m, 6H), 2.31(t, J=7.4Hz, 2H), 2.63–2.75(m, 1H), 2.80(dd, J=13.8Hz, J= 6.2Hz, 1H), 2.99(dd, J= 13.8Hz, J=8.7Hz, 1H), 3.66(s, 3H), 7.35–7.55(m, 4H). |
| XXVc (from XXVb) | 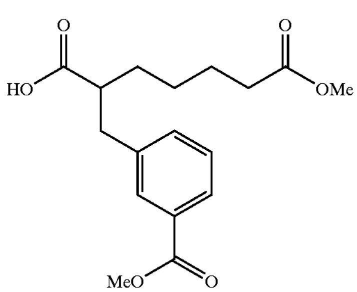 | 43.6 | ¹H-NMR(300MHz, CDCl₃): δ=1.24–1.75(m, 6H), 2.29(t, J=7.4Hz, 2H), 2.66–2.79(m, 1H), 2.81(dd, J=13.6Hz, J= 6.8Hz, 1H), 3.02(dd, J= 13.6Hz, J=7.9Hz, 1H), 3.65(s, 3H), 3.91(s, 3H), 7.31–7.40(m, 2H), 7.84–7.93(m, 2H). |

| Example | Structure | Yield [%] | 1H-NMR Data |
|---|---|---|---|
| XXVIc (from XXVIb) | 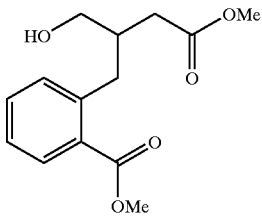 | 57.3 | 1H-NMR(300MHz, CDCl3): δ=1.23–1.80(m, 6H), 2.92(t, J=7.2Hz, 2H), 2.70–2.82(m, 1H), 3.13–3.28(m, 2H), 3.61(s, 3H), 3.90(s, 3H), 7.20–7.33(m, 2H), 7.37–7.46 (m, 1H), 7.90–7.99(m, 1H). |

XIXd: Methyl 2-[2-(hydroxymethyl)-4-methoxy4-oxobutyl/benzoate

At −10° C., 2.16 ml (2.16 mmol) of borane-THF (1 M solution in THF) were added to a solution of 470 mg (1.68 mmol) of 2-[[2-(methoxycarbonyl)phenyl]methyl]butanedioic acid 4-methyl ester from Ex. XIXc in 5 ml of THF. The mixture was allowed to warm to room temperature and stirred for 16 h. The solution was carefully admixed with water and extracted three times with ethyl acetate. The combined organic phases were dried over $Na_2SO_4$ and the solvent was removed. The product was purified chromatographically (silica gel, cyclohexane/ethyl acetate 1:1).

Yield: 266 mg (39.7%) of a slightly yellowish oil.

1H-NMR (300 MHz, CDCl3):

δ=1.56 (bs, 1H), 2.29–2.41 (m, 1H), 2.40–2.60 (m, 2H), 2.77 (dd, J=13.2 Hz, J=6.1 Hz, 1H), 3.26 (dd, J=13.2 Hz, J=8.5 Hz, 1H), 3.45–3.57 (m, 1H), 3.66 (s, 3H), 3.90 (s, 3H), 7.23–7.35 (m, 2H), 7.45 (dt, J=7.4 Hz, J=1.3 Hz, 1H), 7.88 (dd, J=7.7 Hz, J=1.3 Hz, 1H).

The following compounds were prepared analogously:

| Example | Structure | Yield [%] | 1H-NMR Data |
|---|---|---|---|
| XXd (from XXc) | 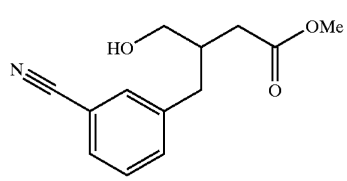 | 74.8 | 1H-NMR(300MHz, CDCl3): δ=1.79(bs, 1H), 2.21–2.51(m, 3H), 2.57–2.92(m, 3H), 3.45–3.70(m, 1H), 3.67(s, 3H), 7.35–7.60(m, 4H). |
| XXId (from XXIc) | 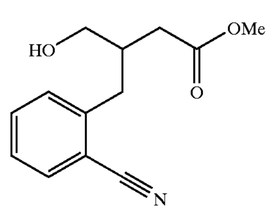 | 58.4 | 1H-NMR(300MHz, CDCl3): δ=1.56(bs, 1H), 1.83bs, 1H), 2.32–2.57(m, 3H), 2.83(dd, J=13.8Hz, J=6.6Hz, 1H), 3.02(dd, J=13.8Hz, J=6.9Hz, 1H), 3.53–3.74(m, 1H), 3.66(s, 3H), 7.27–7.42(m, 2H), 7.53(dt, J=7.7Hz, J=1.3 Hz, 1H), 7.62(d, J=7.7Hz, 1H). |
| XXIId (from XXIIc) | 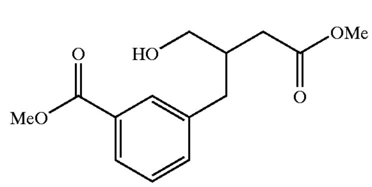 | 49.0 | 1H-NMR(300MHz, CDCl3): δ=1.66(bs, 1H), 2.28–2.51(m, 3H), 2.54–2.88(m, 2H), 3.45–3.70(m, 2H), 3.66(s, 3H), 3.91(s, 3H), 7.31–7.45(m, 2H), 7.81–7.96(m, 2H). |

-continued

| Example | Structure | Yield [%] | ¹H-NMR Data |
|---|---|---|---|
| XXIIId (from XXIIIc) | HO-CH₂-CH(CH₂-2-CN-C₆H₄)-(CH₂)₃-COOMe | 52.2 | ¹H-NMR(300MHz, CDCl₃): δ=1.21–1.78(m, 7H), 1.90(sept., J=6.8Hz, 1H), 2.30(t, J=7.4Hz, 2H), 2.81(dd, J=13.7Hz, J=6.7 Hz, 1H), 2.95(dd, J=13.7 Hz, J=7.8Hz, 1H), 3.55(d, J=4.9Hz, 2H), 3.66(s, 3H), 7.23–7.37(m, 2H), 7.51(t, J=7.6Hz, 1H), 7.61(d, J= 7.6Hz, 1H). |
| XXIVd (from XXIVc) | HO-CH₂-CH(CH₂-3-CN-C₆H₄)-(CH₂)₃-COOMe | 48.2 | ¹H-NMR(300MHz, CDCl₃): δ=1.17–1.67(m, 7H), 1.78(sept, J=5.7Hz, 1H), 2.30(t, J=7.2Hz, 2H), 2.63(dd, J=13.7Hz, J=6.7 Hz, 1H), 2.75(dd, J=13.7 Hz, J=7.5Hz, 1H), 3.50(d, J=5.1Hz, 2H), 3.66(s, 3H), 7.33–7.54(m, 4H). |
| XXVd (from XXVc) | HO-CH₂-CH(CH₂-3-CO₂Me-C₆H₄)-(CH₂)₃-COOMe | 72.8 | ¹H-NMR(300MHz, CDCl₃): δ=1.17–1.70(m, 7H), 1.74–1.89(m, 1H), 2.29(t, J=7.2Hz, 2H), 2.64 (dd, J=13.6Hz, J=6.6Hz, 1H), 2.73(dd, J=13.6Hz, J= 7.8Hz, 1H), 3.51(d, J= 4.9Hz, 2H), 3.66(s, 3H), 3.91(s, 3H), 7.29–7.42(m, 2H), 7.81–7.92(m, 2H). |
| XXVId (from XXVIc) | HO-CH₂-CH(CH₂-2-CO₂Me-C₆H₄)-(CH₂)₃-COOMe | 73.5 | ¹H-NMR(300MHz, CDCl₃): δ=1.20–1.84(m, 7H), 2.31(t, J=7.6Hz, 2H), 2.78(dd, J=13.2Hz, J=5.9 Hz, 1H), 3.18(dd, J=13.2 Hz, J=8.9Hz, 1H), 3.44(d, J=3.8Hz, 2H), 3.66(s, 3H), 3.89(s, 3H), 7.19–7.32(m, 2H), 7.43(t, J=7.7Hz, 1H), 7.86(d, J=8.1Hz, 1H). |

XXIII: Methyl 6-(2-cyanobenzyl)-7-oxoheptanoate

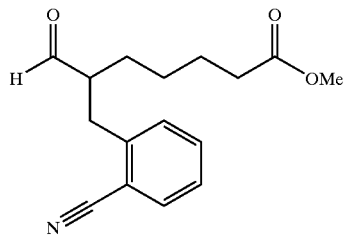

At −60° C., a solution of 49.37 mg (0.63 mmol) of dimethyl sulfoxide (DMSO) in 0.5 ml of dichloromethane was added dropwise to a solution of 40.10 mg (0.32 mmol) of oxalyl chloride in 2 ml of dichloromethane. The mixture was stirred at −60° C. for 15 min, and a solution of 58.00 mg (0.21 mmol) of methyl &(2-cyanobenzyl)-7-hydroxyheptanoate from Ex. XXIIId in 1 ml of dichloromethane was then added dropwise. The mixture was stirred at −60° C. for another 15 min, 106.58 mg (1.05 mmol) of triethylamine were added, the cooling bath was removed and the mixture was stirred for 2 h. Water was added, the mixture was extracted with dichloromethane, the combined organic phases were dried over Na₂SO₄, the solvent was removed and the crude product was dried under high vacuum. The resulting aldehyde could be used without further purification.

The following compounds were prepared analogously and used without further purification:

| Example | Structure |
|---------|-----------|
| XIX | |
| XX | 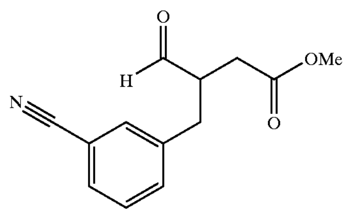 |
| XXI | 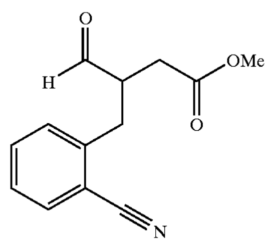 |
| XXII | 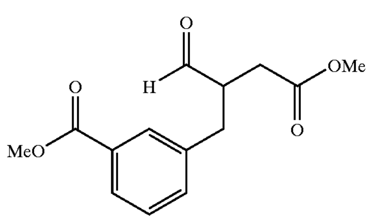 |
| XIX | |
| XXV | 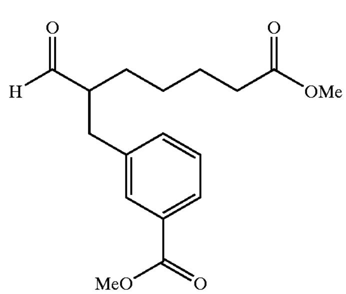 |

-continued

| Example | Structure |
|---------|-----------|
| XXVI | 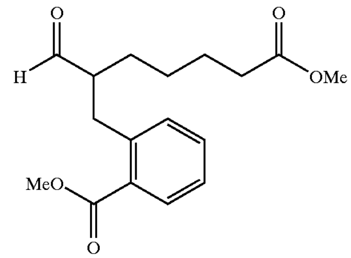 |

EXAMPLE XXVII

Synthesis of benzaldehyde derivatives
XXVIIa: 2-[(5-Phenylpentyl)oxy]benzaldehyde At −60° C., a solution of 9.54 g (122.05 mmol) of dimethyl sulfoxide in 50 ml of $CH_2Cl_2$ was added dropwise to a solution of 7.75 g (61.03 mmol) of oxaly chloride in 100 ml of $CH_2Cl_2$. The mixture was stirred at −60° C. for 15 min, and a solution of 11.00 g (40.68 mmol) of 2-[(5-phenylpentyl)oxy]benzyl alcohol from Ex. VIIa in 50 ml of $CH_2Cl_2$ was then added dropwise. The mixture was stirred at −60° C. for 15 min and 20.59 ml (203.42 mmol) of triethylamine were then added. The mixture was stirred at −60° C. for one hour, the cooling bath was removed and the mixture was stirred for one hour. Water was added, the mixture was extracted with $CH_2Cl_2$, the combined organic phases were dried over $Na_2SO_4$ and the solvent was removed. The product was purified chromatographically (silica gel, cyclohexane/EA 10:1). This gave 9.68 g (88.7%) of a colorless liquid.

$^1$H-NMR (300 MHz, $CDCl_3$): δ=1.44–1.62 (m, 2H), 1.64–1.77 (m, 2H), 1.78–1.94 (m, 2H), 2.64 (t, J=7.6 Hz, 2H), 4.05 (t, J=6.2 Hz, 2H), 6.87–7.03 (m, 2H), 7.09–7.32 (m, 5H), 7.45–7.55 (m, 1H), 7.77–7.85 (m, 1H), 10.48 (s, 1H).

XXVIIb: 2-{[tert-Butyl(dimethyl)silyl]oxy}benzaldehyde 13.58 g (90.07 mmol) of t-butyldimethylsilyl chloride (TBDMSCl) were added to a solution of 10.00 g (81.$89 mmol) of salicylaldehyde and 6.13 g (90.07 mmol) of imidazole in 82 ml of DMF. The mixture was stirred at room temperature and the reaction was monitored by thin-layer chromatography (cyclohexane/EA 10:1). 1 N NaOH was added to the mixture, which was then extracted with petroleum ether. The combined organic phases were dried over $Na_2SO_4$, the solvent was removed and the product was purified chromatographically (silica gel, cyclohexane/EA 10:1). This gave 16.94 g (87.5%) of a clear liquid.

$^1$H-NMR (300 MHz, $CDCl_3$): δ=0.18 (s, 6H), 0.92 (s, 9H), 6.78 (d, J=8.3 Hz, 1H), 6.93 (t, J=7.7 Hz, 1H), 7.36 (dt, J=8.1 Hz, J=1.9 Hz, 1H), 7.71 (dd, J=9.3 Hz, J=1.5 Hz, 1H), 10.37 (s, 1H).

EX. XXVIII

Methyl 7-(diethoxyphosphoryl)-6-oxoheptanoate

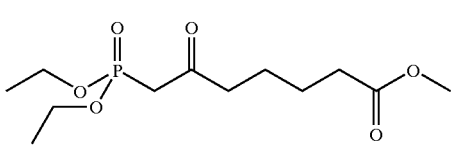

At 0° C., 30.34 g (299.79 mmol) of triethylamine and 12.21 g (112.42 mmol) of trimethylchlorosilane were added dropwise to a solution of 15.00 g (74.95 mmol) of diethyl phosphonoacetate in 400 ml of toluene. The mixture was stirred at room temperature for 1 h, and 7.14 g (74.95 mmol) of magnesium chloride were added. The mixture was stirred for one hour, and 16.56 g (89.94 mmol) of monomethyl adipoyl chloride were added. The mixture was stirred at room temperature for 24 h. Water was added. The mixture was extracted with diethyl ether, the organic phases were dried over $Na_2SO_4$ and the solvent was removed. The product was purified chromatographically (silica gel, ethyl acetate). This gave 7.83 g (35.5%) of a clear liquid.

$^1$H NMR (300 MHz, $CDCl_3$): δ=1.34 (t, J=6.9 Hz, 6H), 1.59–1.66 (m, 4H), 2.25–2.40 (m, 2H), 2.59–2.70 (m, 2H), 3.07 (d, J=22.9 Hz, 2H), 3.66 (s, 3H), 4.14 (quint, J=7.2 Hz, 4H).

EX. XXIX

Synthesis of 6-oxo-7-octenoic acid derivatives
XXIXa: Methyl (E)-6-oxo-8-{2-[(5-phenylpentyl)oxy]phenyl)}-7-octenoate

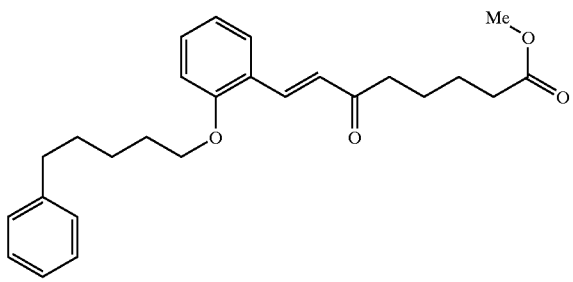

Under argon, 0.26 g (10.87 mmol) of sodium hydride was added to a solution of 3.20 g (10.87 mmol) of methyl 7-(diethoxyphosphoryl)-6-oxoheptanoate from Ex. XXVIII in 53 ml of THF. The mixture was stirred at room temperature for 30 min, a solution of 2.43 g (9.06 mmol) of 2-[(5-phenylpentyl)oxy]benzaldehyde from Ex. XVIIa in 20 ml of THF was added dropwise and the mixture was stirred at room temperature for 18 h. Water was added, the mixture was extracted with ethyl acetate, the combined organic phases were dried over $Na_2SO_4$ and the solvent was removed. The product was purified chromatographically (silica gel, cyclohexane/EA 10:1). This gave 2.51 g (67.8%) of a colorless liquid.

$^1$H-NMR (300 MHz, $CDCl_3$): δ=1.49–1.60 (m, 2H), 1.63–1.79 (m, 6H), 1.84–1.95 (m, 2H), 2.35 (t, =6.8 Hz, 2H), 2.66 (t, J=7.9 Hz, 4H), 3.66 (s, 3H), 4.03 (t, J=6.6 Hz, 2H), 6.79 (d, J=16.3 Hz, 1H), 6.85–6.98 (m, 2H), 7.11–7.37 (m, 6H), 7.47–7.57 (m, 1H), 7.89 (d, J=16.3 Hz, 1H).

EX. XXIXb

Methyl (E8-(2-([tert-butyl(dimethyl)silyl]oxy]phenyl)-6-oxo-7-octenoate

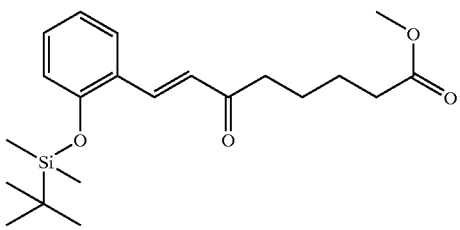

This compound was prepared analogously to Ex. XXIXa from the compounds XVIIb and XXVIII.

$^1$H-NMR (300 MHz, $CDCl_3$): δ 0.24 (s, 6H), 1.05 (s, 9H), 1.62–1.77 (m, 4H), 2.29–2.41 (m, 2H), 2.62–2.73 (m, 2H), 3.66 (s, 3H), 6.67 (d, J=16.6 Hz, 1H), 6.84 (m, =1H), 6.96 (t, J=7.6 Hz, 1H), 7.20–7.30 (m, 1H), 7.56 (d, J=7.7 Hz, 1H), 7.96 (d, J=16.6 Hz, 1H).

EX. XXX

Synthesis of 6-hydroxy-7-octenoic acid derivatives
XXXa: Methyl (E)-6-hydroxy-8-{2-[(5-phenylpentyl)oxy]phenyl}-7-octenoate

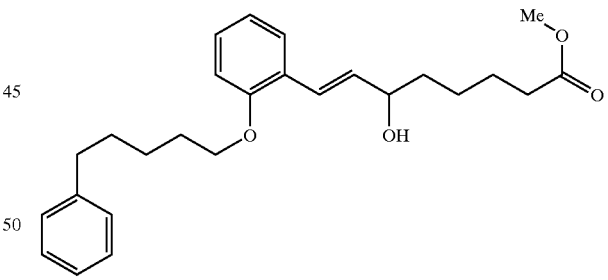

At 0° C., 0.146 g (3.86 mmol) of sodium borohydride were added to a solution of 1.436 g (3.86 mmol) of $CeCl_3 7H_2O$ and 1.50 g (3.67 mmol) of methyl (E)$_6$-oxo-8-12-[(5-phenylpentyl)oxy]phenyl)-7-octenoate from Ex. XXIXa in 30 ml of methanol. The mixture was stirred at 0° C. and the progress of the reaction was monitored by thin-layer chromatography. Saturated $NH_4Cl$ solution was added, the mixture was extracted with ethyl acetate and the combined organic phases were dried over $Na_2SO_4$. The product was purified chromatographically (silica gel, cyclohexane/EA 10:2). This gave 1.38 g (91.5%) of a colorless liquid.

$^1$H-NMR (400 MHz, $CDCl_3$): δ=1.37–1.76 (m, 10H), 1.85 (quint, J=6.6 Hz, 2H), 2.32 (t, J=7.6 Hz, 2H), 2.65 (t, J=7.6 Hz, 2H), 3.65 (s, 3H), 3.98 (t, J=6.6 Hz, 21H), 4.25 (q, J=6.4 Hz, 2H), 6.22 (dd, J=15.9 Hz, J=7.1 Hz, 1H), 6.80 (m, 3H), 7.13–7.32 (m, 6H), 7.39–7.46 (m, 11H).

EX. XXXb

Methyl (E)-8-(2-[tert-butyl(dimethyl)silyl)oxy)phenyl)-6-hydroxy-7-octenoate

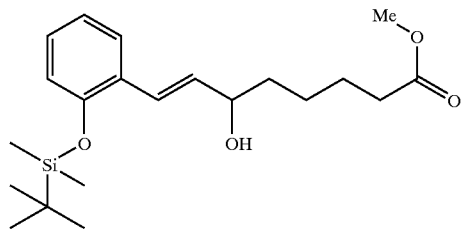

This compound was prepared analogously to Ex. XXXa from the compound XIXb.

$^1$H NMR (400 MHz, CDCl$_3$): δ=0.01 (s, 6H), 0.80 (s, 9H), 1.13–1.54 (m, 7H), 2.11 (t J=7.3 Hz, 2H), 3.44 (s, 3H), 3.99–4.11 (m, 1H), 5.93 (dd, J=15.9 Hz, J=6.9 Hz, 1H), 6.57 (dd, J=8.0 Hz, J=1.0 Hz, 1H), 6.63–6.73 (m, 2H), 6.90 (dt, J=8.0 Hz, J=1.7 Hz, 1H), 7.23 (dd, J=7.8 Hz, J=1.7 Hz, 1H).

EX. XXXI

Synthesis of 6-hydroxy-octanoic acid derivatives

XXXIa: Methyl 6-hydroxy-8-{2-[(5-phenylpentyl)oxy]phenyl}octanoate

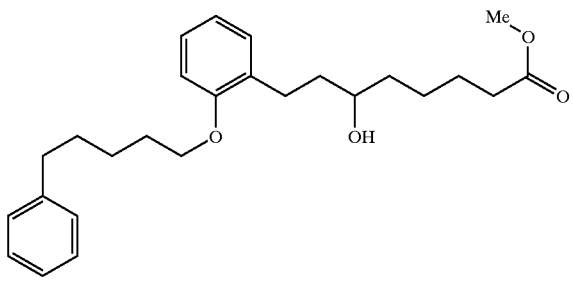

30 mg of palladium-on-carbon (10%) were added to a solution of 1.80 g (4.38 mmol) of methyl (E)-6-hydroxy-8-{2-[(5-phenylpentyl)oxy]phenyl)-7-octenoate from Ex. XXXa in 22.5 ml of ethyl acetate. The mixture was stirred under an atmosphere of hydrogen until no further absorption was observed and filtered through Celite, and the solvent was removed. This gave 1.76 g (97.3%) of a colorless liquid.

$^1$H-NMR (300 MHz, CDCl$_3$): δ=1.21–1.90 (m, ISH), 2.29 (t, J=7.4 Hz, 2H), 2.64 (t, J=7.4 Hz, 211), 2.67–2.84 (m, 2H), 3.41–3.54 (bs, 1H), 3.64 (s, 3H), 3.88–4.08 (m, 2H), 6.78–6.92 (m, 2H), 7.07–7.21 (m, 5H), 7.21–7.32 (m, 2H).

EX. XXXIb

Methyl 8-(2-{[tert-butyl(dimethyl)silyl]oxy}phenyl)-6-hydroxyoctanoate

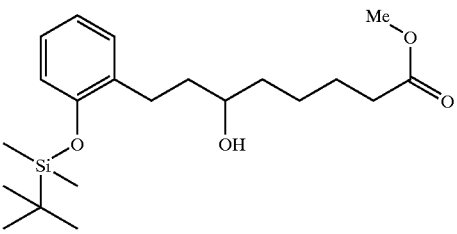

Yield: 82%

$^1$H NMR (300 MHz, CDCl$_3$): δ=0.25 (s, 3H), 0.26 (s, 3H), 1.03 (s, 9H), 1.20–1.84 (m, 9H), 2.26–2.38 (m, 2H), 2.66–2.78 (m, 2H), 3.49–3.62 (m, 1H), 3.67 (s, 3H), 6.75–6.84 (m, 1H), 6.85–6.94 (m, 1H), 7.02–7.19 (m, 2H).

EX. XXXII

Methyl 6-bromo-842-[(5-phenylpentyl)oxy]phenyl)octanoate

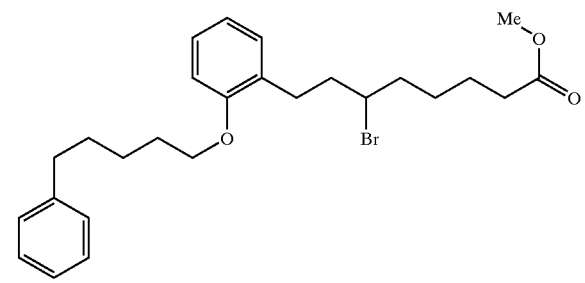

At 0° C., 030 g (1.09 mmol) of phosphorus tribromide was added dropwise to a solution of 1.00 g (2.42 mmol) of methyl 6-hydroxy-8-(2-[(5-phenylpentyl)oxy]-phenyl}octanoate from Ex. XXXIa in 5 ml of diethyl ether. The mixture was stirred at 0° C. for 1 h and then at room temperature for 16 h. Water was added, the mixture was extracted with petroleum ether, the combined organic phases were dried over Na$_2$SO$_4$ and the solvent was removed. The product was purified chromatographically (silica gel, cyclohexane/EA 10:2). This gave 0.62 g (53.7%) of a colorless liquid.

$^1$H-NMR (300 MHz, CDCl$_3$): δ=1.40–1.90 (m, 12H), 2.00–2.14 (m, 2H), 2.30 (t, J=7.2 Hz, 2H), 2.65 (t, J=7.7 Hz, 2H), 2.65–2.75 (m, 1H), 2.80–2.96 (m, 1H), 3.65 (s, 3H), 3.89–4.02 (m, 3H), 6.76–6.90 (m, 2H), 7.09–7.21 (m, 5H), 7.22–7.31 (m, 2H).

Synthesis Examples

EX. 1

Methyl 8-(2-benzyloxyphenyl)-6-(4-methoxycarbonylbenzyl)-7-octenoate

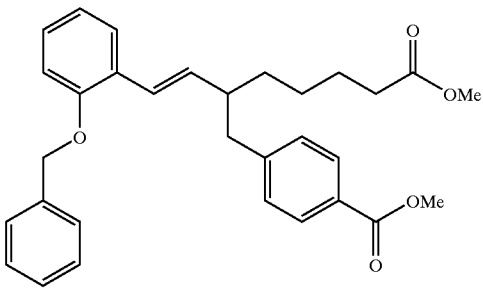

At 0° C. and under argon, 343.4 mg (0.64 mmol) of 2-(benzyloxy)benzyl-triphenylphosphonium bromide from Ex. III are suspended in 20 ml of THF, and 0.48 ml of butyllithium (0.76 mmol, 1.6 M solution in hexane) is added. The deep-orange solution is stirred at 0° C. for 30 min, and a solution of 195 mg (0.64 mmol) of methyl 6-formyl-7-(4-methoxycarbonylphenyl)heptanoate (prepared analogously to Example I from t-butyl 2-oxocyclohexanecarboxylate and methyl 4-chloromethylbenzoate, cf. EP-A-0 341 551) in 15 ml of THF is added dropwise at this temperature. The mixture is stirred at 0° C. for 30 min. At 0° C., water is added, and the mixture is then warmed to room temperature and extracted with ethyl acetate. The organic phase is washed with sodium chloride solution, dried with magnesium sulfate and concentrated using a rotary evaporator. For purification, the substance was chromatographed on 40 g of silica gel 60 (particle size 0.040–0.063 mm) using the mobile phase petroleum ether/ether 4:1 to 1:1.

Yield: 154 mg (49.7% of theory) as a mixture: 71.0% trans/29.0% cis.

$^1$H-NMR (200 MHz, CDCl$_3$): 7.90 (m, 2H), 7.40–6.80 (m, 11H), 6.60 (d, 0.7H, J=16 Hz), 6.50 (d, 0.3H, J=9 Hz), 5.95 (dd, 0.7H, J=16 Hz, J=9 Hz), 5.40 (t, 0.3H, J=9 Hz), 5.00 (s, 1.4H), 4.90 (m, 0.6H), 3.85 (s, 3H), 3.60 (s, 3H), 2.80–2.40 (m, 3H), 2.30–2.10 (m, 2H), 1.60–1.20 (m, 6H)

The following compounds were prepared analogously:

| Example | Formula | Yield | NMR Data or R$_f$ Values |
|---|---|---|---|
| 2 (from IV and the aldehyde from Ex. 1) | [structure] | 38.5 | 76%(E), 24%(Z) <br> $^1$H-NMR(200MHz, CDCl$_3$): 7.90 (m, 2H), 7.40–7.20(m, 8H), 6.80–6.60(m, 2H), 6.55(d, 0.8H, J=16 Hz), 6.50(d, 0.2H, J=9Hz), 5.90 (dd, 0.8H, J=16Hz, J=9Hz), 5.40 (t, 0.2H, J=9Hz), 5.00(s, 1.6H), 4.90(m, 0.4H), 3.90(s, 3H), 3.60 (s, 3H), 2.90–2.50(m, 3H), 2.30–2.10(m, 5H), 1.60–1.20(m, 6H) |
| 3 (from II and X) | [structure] | 36.8 | 70%(E), 30%(Z) <br> $^1$H-NMR(200MHz, CDCl$_3$): 7.50 (m, 2H), 7.40–7.10(m, 11H), 6.50 (d, 0.7H, J=16Hz), 6.40(d, 0.3H, J=9Hz), 5.90(dd, 0.7H, J=16Hz, J=9Hz), 5.30(t, 0.3H, J=9Hz), 4.10(q, J=6Hz, 2H), 3.90(m, 2H), 2.90–2.40(m, 5H), 2.30(m, 2H), 1.20(m, 15H) |
| 4 (from V and the aldehyde from Ex. 1) | [structure] | 23.1 | 71%(E), 29%(Z) <br> $^1$H-NMR(200MHz, CDCl$_3$): 7.90 (m, 2H), 7.40–6.80(m, 10H), 6.60 (d, 0.7H, J=16Hz), 6.55(d, 0.3H, J=9Hz), 6.00(dd, 0.7H, J=16Hz, J=9Hz), 5.40(t, 0.3H, J=9Hz), 5.15(s, 1.4H), 5.00(m, 0.6H), 3.85(s, 3H), 3.60(s, 3H), 2.90–2.50(m, 3H), 2.30–2.00(m, 2H), 1.60–1.20(m, 6H) |

-continued

| Example | Formula | Yield | NMR Data or R_f Values |
|---|---|---|---|
| 5 (from VIII and the aldehyde from Ex. 1) | | 48.5 | 77%(E), 23%(Z) $^1$H-NMR(200MHz, CDCl$_3$): 7.90 (m, 2H), 7.40–7.10(m, 9H), 6.85 (m, 2H), 6.55(d, 0.8H, J=16Hz), 6.50(d, 0.2H, J=9Hz), 6.00(dd, 0.8H, J=16Hz, J=9Hz), 5.40(t, 0.2H, J=9Hz), 3.90(m, 2H), 3.85 (s, 3H), 3.60(s, 3H), 2.90–2.50 (m, 5H), 2.30–2.00(m, 2H), 1.60–1.20(m, 8H) |
| 6 (from X and the aldehyde from Ex. 1) | | 54.2 | 70%(E), 30%(Z) $^1$H-NMR(200MHz, CDCl$_3$): 7.90 (m, 2H), 7.40–7.10(m, 9H), 6.85 (m, 2H), 6.50(d, 0.7H, J=16Hz), 6.45(d, 0.3H, J=9Hz), 5.95(dd, 0.7H, J=16Hz, J=9Hz), 5.40(t, 0.3H, J=9Hz), 3.90(m, 2H), 3.85 (s, 3H), 3.60(s, 3H), 2.90–2.60 (m, 4H), 2.50(m, 1H), 2.30–2.00 (m, 2H), 1.90–1.20(m, 12H) |
| 7 (from VII and the aldehyde from Ex. 1 (ethyl ester)) | | 72.9 | 75%(E), 25%(Z) $^1$H-NMR(400MHz, CDCl$_3$): 7.90 (m, 2H), 7.30–7.10(m, 9H), 6.95–6.65(m, 2H), 6.50(d, 0.7H, J=16 Hz), 6.40(d, 0.3H, J=9Hz), 5.90 (dd, 0.7H, J=16Hz, J=9Hz), 5.35 (t, 0.3H), 4.40(q, J=6Hz, 2H), 4.15(q, J=6Hz, 2H), 4.10(m, 2H), 3.00(m, 2H), 2.90–2.60(m, 2H), 2.40(m, 1H), 2.30–2.10(m, 2H), 1.55–1.20(m, 12H) |
| 8 (from XI and the aldehyde from Ex. 1 (ethyl ester)) | | 83.3 | 75%(E), 25%(Z) $^1$H-NMR(400MHz, CDCl$_3$): 7.93 (m, 1.5H), 7.88(m, 0.5H), 7.50–7.10(m, 9H), 6.90–6.70(m, 2H), 6.55(d, 0.7H, J=16Hz), 6.48(d, 0.3H, J=9Hz), 6.00(dd, 0.7H, J=16Hz, J=9Hz), 5.40(t, 0.3H), 4.40(q, J=6Hz, 2H), 4.15(q, J=6 Hz, 2H), 3.90(m, 2H), 2.90–2.60 (m, 4H), 2.50(m, 1H), 2.30(m, 2H), 1.55–1.20(m, 20H) |

-continued

| Example | Formula | Yield | NMR Data or $R_f$ Values |
|---|---|---|---|
| 9 (from I and X) | | crude | $R_f$(SiO$_2$, C1E1): 0.66 |
| 10 (from III and the aldehyde from Ex. 1 (ethyl ester)) | | 49.8 | $^1$H-NMR(200MHz, CDCl$_3$): 7.95 (d, 2H, J=10Hz), 7.40–7.10(m, 8H), 6.90(m, 2H), 6.52(d, 1H, J=16Hz), 5.95(dd, 1H, J=16Hz, J=9Hz), 5.00(m, 2H), 4.35(q, J=6Hz, 2H), 4.10(q, J=6Hz, 2H), 2.75(m, 2H), 2.45(m, 1H), 2.30(m, 2H), 1.80–1.10(m, 12H) |

EX. 11
8-(2-Benzyloxyphenyl)-6-(4-carboxybenzoyl)-7-octenoic acid

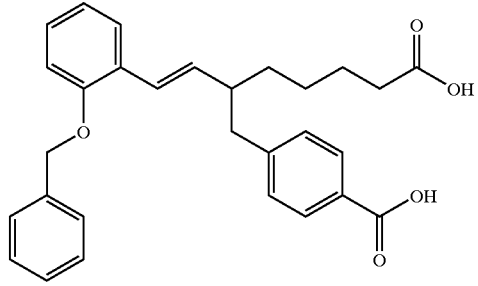

135 mg (0.28 mmol) of the diester from Example 1 are dissolved in 5 of methanol and, at 0° C., 1.5 ml of 45% strength aqueous sodium hydroxide solution are added. The mixture is allowed to warm to room temperature, and 0.2 ml of dichloromethane is added. The solution is stirred at room temperature for 16 hours, a little water is added and the mixture is extracted with ethyl ether. The aqueous phase is adjusted to pH 2–3 using 10% strength sulfuric acid and extracted twice with ethyl acetate and dried with magnesium sulfate. The solvent is removed under reduced pressure.

Yield: 116 mg (91.2% of theory) as a mixture: 71.0% trans/29.0% cis.

$^1$H-NMR (400 MHz, CD$_3$COCD$_3$): 10.0 (bs, 2H), 7.90 (m, 2H), 7.40–6.80 (m, 11H), 6.60 (d, 0.7H, J=16 Hz), 6.50 (d, 0.3H, J=9 Hz), 6.10 (dd, 0.7H, J=16 Hz, J=9 Hz), 5.50 (t, 0.3H, J=9 Hz), 5.10 (s, 1.4H), 5.00 (m, 0.6H), 2.90–2.50 (m, 3H), 2.30–2.10 (m, 2H), 1.60–1.20 (m, 6H)

The following substances were synthesized analogously to Example 11:

| Example | Formula | Yield | NMR Data |
|---|---|---|---|
| 12 (from 2) | | crude | 76%(E), 24%(Z) $^1$H-NMR(400MHz, CD$_3$COCD$_3$): 10.7(bs, 2H), 7.90 (m, 2H), 7.40–7.20(m, 8H), 6.80–6.60(m, 2H), 6.55(d, 0.8H, J=16Hz), 6.50(d, 0.2H, J=9Hz), 6.00(dd, 0.8H, J=16 Hz, J=9Hz), 5.40(t, 0.2H, J=9Hz), 5.10(s, 1.6H), 5.00(m, 0.4H), 2.90–2.50(m, 3H), 2.30–2.10(m, 5H), 1.60–1.20(m, 6H) |

-continued

| Example | Formula | Yield | NMR Data |
|---|---|---|---|
| 13 (from 3) | | 89.4 | $^1$H-NMR(200MHz, CDCl$_3$): 7.50(m, 2H), 7.40–7.10(m, 11H), 6.55(d, 1H, J=16Hz), 5.90(dd, 1H, J=16Hz, J=9Hz), 3.90(m, 2H), 2.90–1.20(m, 19H) |
| 14 (from 4) | | 70.9 | 71%(E), 29%(Z) $^1$H-NMR(400MHz, CD$_3$COCD$_3$): 10.0(bs, 2H), 7.90 (m, 2H), 7.40–6.80(m, 10H), 6.60(d, 0.7H, J=16Hz), 6.50(d, 0.3H, J=9Hz), 6.10(dd, 0.7H, J=16Hz, J=9Hz), 5.50(t, 0.3H, J=9Hz), 5.15(s, 1.4H), 5.10(m, 0.6H), 2.90–2.50(m, 3H), 2.30–2.00(m, 2H), 1.60–1.20(m, 6H) |
| 15 (from 5) | | 86.7 | 77%(E), 23%(Z) $^1$H-NMR(400MHz, CD$_3$COCD$_3$): 10.6(bs, 2H), 7.90 (m, 2H), 7.40–7.10(m, 9H), 6.85(m, 2H), 6.60(d, 0.8H, J=16Hz), 6.50(d, 0.2H, J=9 Hz), 6.10(dd, 0.8H, J=16Hz, J=9Hz), 5.45(t, 0.2H, J=9Hz), 3.90(m, 2H), 2.90–2.50(m, 5H), 2.30–2.00(m, 2H), 1.60–1.20(m, 8H) |
| 16 (from 6) | | 67.4 | trans: $^1$H-NMR(400MHz, CD$_2$Cl$_2$): 10.0(bs, 2H), 7.95(d, 2H, J=10Hz), 7.35(d, 1H, J=10 Hz), 7.25(m, 4H), 7.15(m, 4H), 6.85(m, 2H), 6.52(d, 1H, J=16 Hz), 6.00(dd, 1H, J=16Hz, J=9Hz), 3.90(t, 2H, J=6Hz), 2.80(m, 2H), 2.65(m, 2H), 2.50 (m, 1H), 2.30(t, 2H, J=6Hz), 1.80–1.20(m, 12H) |
| 17 (from 7) | | crude | 75%(E), 25%(Z) $^1$H-NMR(300MHz, d$^6$-DMSO): 7.90(m, 2H), 7.30–7.10(m, 9H), 6.95–6.65(m, 2H), 6.31(d, 0.3H, J=9Hz), 6.30(d, 0.7H, J=16Hz), 6.00(dd, 0.7H, J=16 Hz, J=9Hz), 5.40(t, 0.3H), 4.12 (m, 1.5H), 4.05(m, 0.5H), 3.00 (m, 2H), 2.90–2.60(m, 2H), 2.40 (m, 1H), 2.30–2.10(m, 2H), 1.55–1.20(m, 6H) |

| Example | Formula | Yield | NMR Data |
|---|---|---|---|
| 18 (from 8) | | 68.3 | 75%(E), 25%(Z) <br> $^1$H-NMR(400MHz, CD$_2$Cl$_2$): 7.93(m, 1.5H), 7.88(m, 0.5H), 7.50–7.10(m, 9H), 6.90–6.70(m, 2H), 6.55(d, 0.7H, J=16 Hz), 6.48(d, 0.3H, J=9Hz), 6.00(dd, 0.7H, J=16Hz, J=9Hz), 5.40(t, 0.3H), 3.90(m, 2H), 2.90–2.20(m, 7H), 1.55–1.20(m, 14H) |
| 19 (from 9) | | crude | 75%(E), 25%(Z) <br> $^1$H-NMR(400MHz, CD$_2$Cl$_2$): 790(m, 2H), 7.40–7.10(m, 9H), 6.85(m, 2H), 6.65(d, 0.7H, J=16Hz), 6.50(d, 0.3H, J=9Hz), 6.05(dd, 0.7H, J=16 Hz, J=9Hz), 5.45(t, 0.3H, J=9Hz), 3.90(m, 2H), 2.90–2.50 (m, 5H), 2.30(m, 2H), 1.80–1.20 (m, 10H) |
| 20 (from 10) | | 65.7 | 70%(E), 30%(Z) <br> $^1$H-NMR(400MHz, CDCl3): 7.95(d, 2H, J=10Hz), 7.40–7.10 (m, 8H), 6.90(m, 2H), 6.60(d, 0.7H, J=16Hz), 6.50(d, 0.3H, J=9Hz), 6.10(dd, 0.7H, J=16 Hz, J=9Hz), 5.45(t, 0.3H, J=9Hz), 5.00(m, 2H), 2.75(m, 2H), 2.50(m, 1H), 2.30(t, 2H, J=6Hz), 1.80–1.10(m, 6H) |

EX. 21

Synthesis of 8-(2-benzylphenyl)-6-(4-carboxybenzyl)-7-octenoic acid

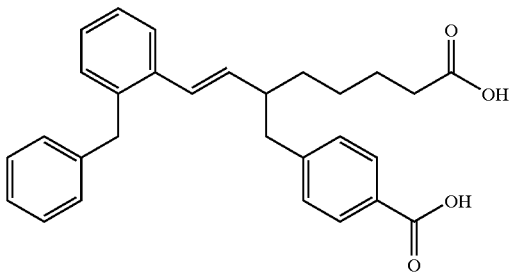

At 0° C. and under argon, 293.5 mg (0.56 mmol) of 2-benzylbenzyltriphenylphosphonium bromide (XVI) are suspended in 20 ml of THF and treated with 0.42 ml of butyllithium (0.72 mmol, 1.6 M solution in hexane). The deep-orange solution is stirred at 0° C. for 30 min, and a solution of 125 mg (0.37 mmol) of ethyl 6-formyl-7-(4-ethoxycarbonylphenyl)heptanoate (prepared analogously to Example I from t-butyl 2-oxocyclohexanecarboxylate and methyl 4-chloromethylbenzoate, cf. EP-A-0 341 551) in 15 ml of THF is added dropwise at this temperature. The mixture is stirred at 0° C. for 30 min. At 0° C., water is added, and the mixture is then warmed to room temperature and extracted with ethyl acetate. The organic phase is washed with sodium chloride solution and dried with magnesium sulfate. The solvent is removed under reduced pressure. The crude product is dissolved in 5 ml of methanol and, at 0° C., treated with 1.5 ml of 45% strength aqueous sodium hydroxide solution. At room temperature, 0.2 ml of dichloromethane is added, whereupon the solution becomes clear. The solution is stirred at room temperature for 16 hours, a little water is added and the mixture is extracted with ethyl ether. The aqueous phase is adjusted to pH 2–3 using 10% strength sulfuric acid and extracted twice with ethyl acetate, dried with magnesium sulfate and concentrated using a rotary evaporator.

Yield: 184 mg (100% of theory) as a mixture: 75.0% trans/25.0% cis.

¹H-NMR (400 MHz, CD₃COCD₃): 10.0 (bs, 2H), 7.90 (m, 2H), 7.60–7.00 (m, 11H), 6.42 (d, 0.3H, J=9 Hz), 6.40 (d, 0.7H, J=16 Hz), 5.80 (dd, 0.7H, J=16 Hz, J=9 Hz), 5.50 (t, 0.3H), 3.85 (s, 1.5H), 3.70 (s, 0.5H), 2.90–2.30 (m, 5H), 1.70–1.20 (m, 6H)

The following compounds were prepared analogously:

| Example | Formula | Yield | NMR Data or LC-MS-Data |
|---|---|---|---|
| 22 (from IX and the aldehyde from Example 21) | | 8.8 | 70%(E), 30%(Z) ¹H-NMR(400MHz, CD₂Cl₂): 7.90(m, 2H), 7.40–7.10(m, 9H), 6.85(m, 2H), 6.55(d, 0.7H, J=16 Hz), 6.50(d, 0.3H, J=9Hz), 6.00 (dd, 0.7H, J=16Hz, J=9Hz), 5.40 (t, 0.3H, J=9Hz), 3.90(m, 2H), 2.90–2.50(m, 5H), 2.30–2.00(m, 2H), 1.60–1.20(m, 10H) |
| 23 (from XV and the aldehyde from Example 21) | | 58.9 | LC-MS: 457(M+1), Rt: 4.81 min |
| 24 (from XII and the aldehyde from Example 21) | | 79 | LC-MS: 503(M+1), Rt: 4.80 min |
| 25 (from VI and the aldehyde from Example 21) | | 69.7 | LC-MS: 527(M+1), Rt: 4.85 min |

-continued

| Example | Formula | Yield | NMR Data or LC-MS-Data |
|---|---|---|---|
| 26 (from XVII and the aldehyde from Example 21) | 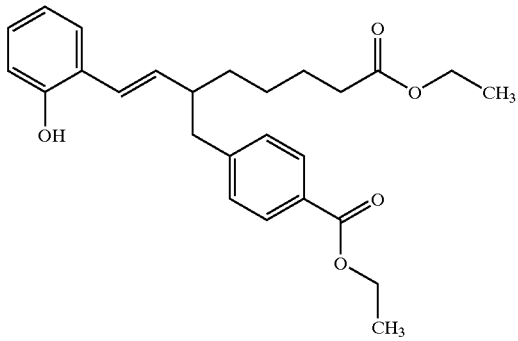 | 51 | 75%(E), 25%(Z)<br>$^1$H-NMR(400MHz, CD$_3$COCD$_3$): 10.60(bs, 2H), 7.90 (m, 2H), 7.40–7.00(m, 8H), 6.80 (m, 2H), 6.50(m, 1H), 5.90(dd, 0.7H, J=16Hz, J=9Hz), 5.60(t, 0.3H, J=9Hz), 3.70(s, 3H), 3.00–2.50(m, 7H), 2.30(m, 2H), 1.70–1.20(m, 6H) |

*LC/MS conditions: column: Symmetry C18 2.1 50 mm; mobile phase: acetonitrile/H$_2$O; gradient: 10% acetonitrile to 90% acetonitrile; flow rate: 0.5 ml/min; detector: UV 210 nm.

EX. 27

Ethyl 8-(2-(4-chlorobenzyloxy)phenyl)$_6$-(4-ethoxycarbonylbenzyl)-7-(E)-octenoate 27a: Ethyl 6-(4-ezhoxycarbonylbenzyl)-8-(2-hydroxyphenyl)-7-(E)-octenoate Under argon, 645 mg (1.44 mmol) of 2-hydroxybenzyltriphenylphosphonium bromide (preparable from 2-hydroxybenzyl alcohol analogously to Ex. III) are suspended in 25 ml of tetrahydrofuran and cooled to 0° C. At this temperature, 2.2 ml of butyllithium (1.6 M solution in hexane) are added. After 30 minutes at this temperature, a solution of 436 mg (1.31 mmol) of the ethyl ester of the aldehyde from Example 1 in 2 ml of THF is added, and the mixture is stirred at 0° C. for another 30 minutes. 1 ml of water and 20 ml of dichloromethane are added and the mixture is acidified using HCl and filtered through Extrelut. The filtrate is concentrated and the product is chromatographed on 30 g of silica gel using cyclohexane/ethyl acetate 2:1.

Yield: 184 mg (33.2% of theory)

$^1$H-NMR (200 MHz, CDCl$_3$): 7.95 (d, 2H, J=10 Hz), 7.25 (d, 2H), 7.10 (m, 2H), 6.80 (m, 2H), 6.40 (d, 1H, J=16 Hz), 5.85 (dd, 1H, J=16 Hz, J=9 Hz), 5.10 (s, 1H), 4.35 (q, J=6 Hz, 2H), 4.10 (m, 2H), 2.75 (m, 2H), 2.50 (m, 1H), 2.30 (m, 3H), 1.80–1.10 (m, 12H)

27: Ethyl 8-(2-(4-chlorobenzyloxy)phenyl)-6-(4-ethoxycarbonylbenzyl)-7-(E)-octenoate

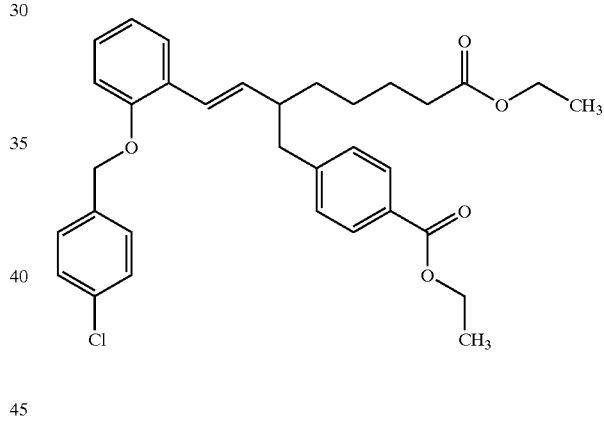

104 mg (0.24 mmol) of phenol from Ex. 27a, 47 mg (0.29 mmol) of 4-chlorobenzyl chloride and 51 mg (0.37 mmol) of potassium carbonate in 10 ml of acetonitrile are heated at reflux for 48 hours. The mixture is cooled, filtered and concentrated. For purification, the residue is chromatographed on silica gel.

Yield: 51 mg (37.9% of theory)

$^1$H-NMR (200 MHz, CDCl$_3$): 7.95 (d, 2H, J=10 Hz), 7.40–7.10 (m, 8H), 6.90 (m, 2H), 6.52 (d, 1H, J=16 Hz), 5.95 (dd, 1H, J=16 Hz, J=9 Hz), 5.00 (s, 2H), 4.35 (q, J=6 Hz, 2H), 4.10 (q, J=6 Hz, 2H), 2.75 (m, 2H), 2.50 (m, 1H), 2.30 (t, 2H, J=6 Hz), 1.80–1.10 (m, 12H)

The following compounds were prepared analogously:

| Example | Formula | Yield | NMR Data |
|---------|---------|-------|----------|
| 28 (from 27a and 4-t-butyl-benzyl bromide) | | 88.5 | $^1$H-NMR(300MHz, CDCl$_3$): 7.90(d, 2H, J=10Hz), 7.40–7.10(m, 8H), 6.90 (m, 2H), 6.60(d, 1H, J=16Hz), 6.00 (dd, 1H, J=16Hz, J=9Hz), 5.00(s, 2H), 4.35(q, J=6Hz, 2H), 4.10(q, J=6Hz, 2H), 2.75(m, 2H), 2.50(m, 1H), 2.30(t, 2H, J=6Hz), 1.70–1.15(m, 21H) |
| 29 (from 27a and 4-ethyl benzyl chloride) | | 61.0 | $^1$H-NMR(300MHz, CDCl$_3$): 7.90(d, 2H, J=10Hz), 7.40–7.10(m, 8H), 6.90 (m, 2H), 6.60(d, 1H, J=16Hz), 6.00 (dd, 1H, J=16Hz, J=9Hz), 5.00(s, 2H), 4.35(q, J=6Hz, 2H), 4.10(q, J=6Hz, 2H), 2.70(m, 4H), 2.50(m, 1H), 2.25(m, 2H), 1.70–1.15(m, 15H) |
| 30 (from 27a and 4-trifluoro-methyl-benzyl bromide) | | 51.8 | $^1$H-NMR(300MHz, CDCl$_3$): 7.90(m, 2H), 7.60(m, 2H), 7.50–7.05(m, 6H), 6.90(m, 2H), 6.55(d, 1H, J=16Hz), 6.00(dd, 1H, J=16Hz, J=9Hz), 5.05 (s, 2H), 4.35(q, J=6Hz, 2H), 4.10(q, J=6Hz, 2H), 2.80(m, 2H), 2.50(m, 1H), 2.25(m, 2H), 1.70–1.20(m, 12H) |

| Example | Formula | Yield | NMR Data |
|---|---|---|---|
| 31 (from 27a and 4-fluoro-benzyl bromide) | | 62.2 | $^1$H-NMR(300MHz, CDCl$_3$): 7.90(d, 2H, J=10Hz), 7.40–7.00(m, 8H), 6.90 (m, 2H), 6.52(d, 1H, J=16Hz), 5.95 (dd, 1H, J=16Hz, J=9Hz), 5.00(s, 2H), 4.35(q, J=6Hz, 2H), 4.10(q, J=6Hz, 2H), 2.75(m, 2H), 2.50(m, 1H), 2.25(t, 2H, J=6Hz), 1.80–1.10(m, 12H) |
| 32 (from 27a and 4-methyl-benzyl bromide) | | 43.5 | $^1$H-NMR(300MHz, CDCl$_3$): 7.95(d, 2H, J=10Hz), 7.40–7.10(m, 8H), 6.90 (m, 2H), 6.60(d, 1H, J=16Hz), 5.95 (dd, 1H, J=16Hz, J=9Hz), 5.00(s, 2H), 4.35(q, J=6Hz, 2H), 4.10(q, J=6Hz, 2H), 2.75(m, 2H), 2.50(m, 1H), 2.30(s, 3H), 2.25(t, 2H, J=6Hz), 1.80–1.10(m, 12H) |

EX. 33

6-(4-Carboxybenzyl)-8-(2-(4-chlorobenzyloxy) phenyl)-7-(E)-octenoic acid

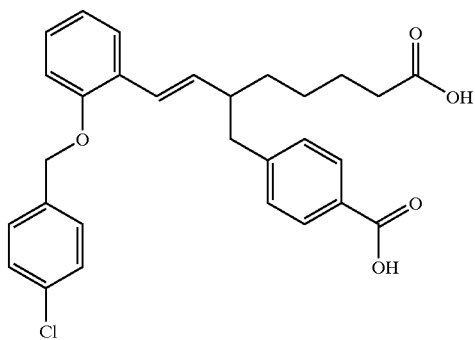

45 mg (0.08 mmol) of diethyl ester from Ex. 27 are dissolved in 5 ml of methanol, and 0.5 ml of 45% strength aqueous sodium hydroxide solution is added. The reaction mixture is allowed to warm to room temperature, and 0.3 ml of dichloromethane is added. After 20 hours of stirring at room temperature, the reaction solution is washed once with water, acidified with 10% strength sulfuric acid and extracted twice with ethyl acetate, and the combined organic phases are filtered through Extrelut and concentrated.

Yield: 11 mg (23% of theory)

LC-MS: 493 (M+1); R$_t$: 4.86 min

The following compounds were prepared analogously:

| Example | Formula | Yield | NMR Data |
|---|---|---|---|
| 34 (from 28) | 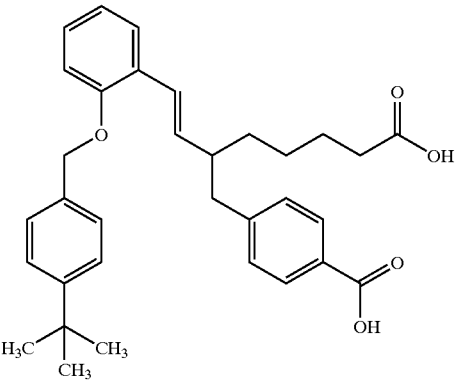 | 85.9 | ¹H-NMR(300MHz, CD₃COCD₃): 7.90(d, 2H, J=10Hz), 740(m, 3H), 7.30(m, 4H), 7.10(t, 1H), 7.00(m, 1H), 6.85(t, 1H), 6.60(d, 1H, J=16 Hz), 6.10(dd, 1H, J=16Hz, J=9Hz), 5.00(s, 2H), 2.90–2.70(m, 2H), 2.55 (m, 1H), 2.25(t, 2H, J=6Hz), 1.65–1.30 (m, 6H), 1.30(s, 9H) |
| 35 (from 29) | 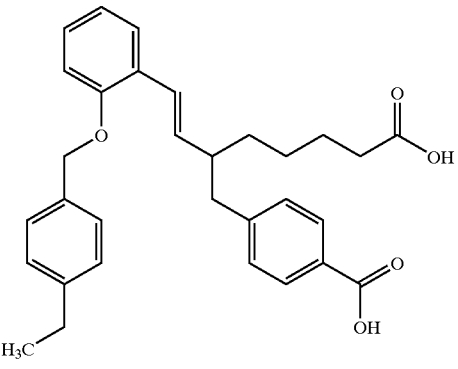 | 62.6 | ¹H-NMR(400MHz, CD₃COCD₃): 7.90(d, 2H), 7.40–7.10(m, 8H), 6.90 (m, 2H), 6.55(d, 1H, J=16Hz), 6.10 (dd, 1H, J=16Hz, J=9Hz), 5.00(s, 2H), 2.90–2.50(m, 5H), 2.25(m, 2H), 1.60–1.25(m, 6H), 1.20(t, J=6Hz, 3H) |
| 36 (from 30) | 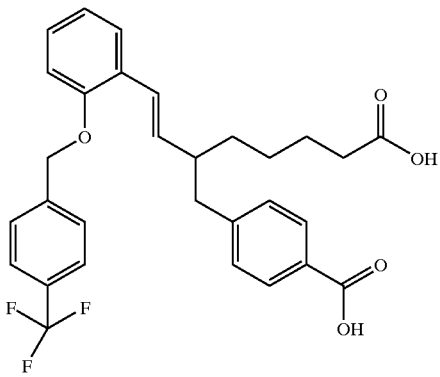 | 51.8 | ¹H-NMR(400MHz, CD₃COCD₃): 10.70(bs, 2H), 7.90(m, 2H), 7.70(m, 2H), 7.60(m, 2H), 7.40(d, 1H), 7.35 (d, 2H), 7.10(m, 1H), 6.95(m, 1H), 6.90(t, 1H), 6.60(d, 1H, J=16Hz), 6.10(dd, 1H, J=16Hz, J=9Hz), 5.20 (s, 2H), 2.90–2.70(m, 2H), 2.55(m, 1H), 2.25(t, 2H), 1.60–1.30(m, 6H) |
| 37 (from 31) | 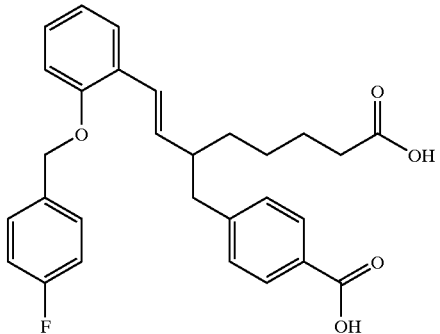 | 58.3 | ¹H-NMR(400MHz, CD₃COCD₃): 7.90(d, 2H, J=10Hz), 7.40(m, 3H), 7.30(d, 2H), 7.10(m, 3H), 6.95(d, 1H), 6.85(t, 1H), 6.50(d, 1H, J=16 Hz), 5.95(dd, 1H, J=16Hz, J=9Hz), 5.00(s, 2H), 2.75(m, 2H), 2.50(m, 1H), 2.25(t, 2H, J=6Hz), 1.60–1.10(m, 6H) |

EX. 38

8-(2-Benzyloxy)phenyl-6-(4-carboxybenzyl)-octanoic acid

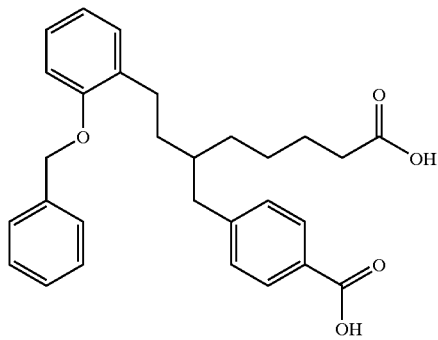

62 mg (0.14 mmol) of 8-(2-benzyloxy)phenyl-6-(4-carboxybenzyl)-7-(E)-octenoic acid from Ex. 11 and 30 mg of palladium/activated carbon 10% are added to 5 ml of ethyl acetate and hydrogenated at room temperature under atmospheric pressure, using hydrogen. After two hours, the mixture is filtered through Celite and the filtrate is concentrated.

Yield: 59 mg (94.7% of theory)

$^1$H-NMR (400 MHz, $CD_2Cl_2$): 9.50 (bs, 2H), 7.85 (m, 2H), 7.35–7.00 (m, 9H), 6.80 (m, 2H), 4.95 (s, 2H), 2.70–2.50 (m, 4*), 2.15 (t, 2H, J=6 Hz), 1.80–1.20 (m, 9H)

The following substances were synthesized analogously:

| Example | Formula | Yield | NMR Data |
|---|---|---|---|
| 39 (from 15) |  | 77.0 | $^1$H-NMR(200MHz, $CD_2Cl_2$): 7.90(m, 2H), 7.30–7.00(m, 9H), 6.80(m, 2H), 3.95(t, 2H, J=6Hz), 2.85–2.55(m, 6H), 2.30(m, 2H), 2.10(m, 2H), 1.80–1.20 (m, 11H) |
| 40 (from 23) |  | 71.9 | $^1$H-NMR(400MHz, $CD_2Cl_2$): 7.95(m, 2H), 7.65(m, 2H), 7.50(m, 1H), 7.30–7.00(m, 8H), 2.80–2.50(m, 8H), 2.30 (t, 2H, J=6Hz), 1.85–1.30(m, 9H) |
| 41 (from 16) |  | 100 | $^1$H-NMR(400MHz, $CD_3COCD_3$): 10.70(bs, 2H), 8.00–7.90(m, 2H), 7.35–7.00(m, 9H), 6.85(d, 1H), 6.80(t, 1H), 3.95(t, 2H), 2.90–2.60(m, 6H), 2.25(m, 2H), 1.80–1.20(m, 15H) |

| Example | Formula | Yield | NMR Data |
|---|---|---|---|
| 42 (from 19) | | 55.6 | ¹H-NMR(400MHz, CD$_2$Cl$_2$): 7.90(m, 2H), 7.55–7.00(m, 9H), 6.75(m, 2H), 3.90(t, 2H, J=6Hz), 2.85–2.45(m, 6H), 2.20(m, 2H), 2.10(m, 2H), 1.80–1.20 (m, 11H) |

EX. 43

6-(4-Carboxybenzyl)-9-(3-(4-phenylbutoxy)phenyl)-7-(Z)-nonenoic acid (

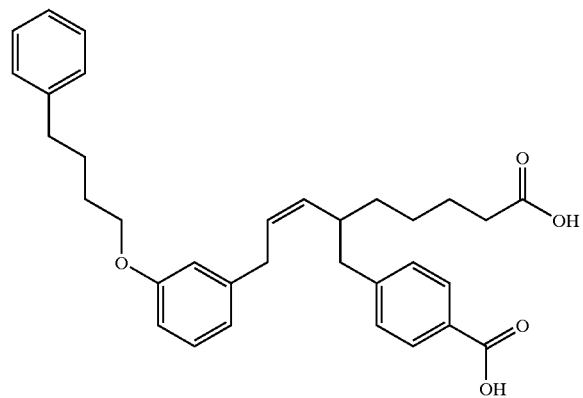

At −30° C. and under argon, 238.2 mg (0.35 mmol) of the phosphonium salt from Ex. XVIII are suspended in 5 ml of THF and treated with 0.26 ml of butyllithium (0.76 mmol, 1.6M solution in hexane). At −30° C., the deep-orange solution is stirred for 30 min, and at this temperature, a solution of 106 mg (0.35 mmol) of methyl 6-formyl-7-(4-methoxycarbonylphenyl)heptanoate (prepared analogously to Example I from t-butyl 2-oxocyclohexanecarboxylate and methyl 4-chloromethylbenzoate, cf. EP-A-0 341 551) in 1 ml of THF is added dropwise at this temperature. The mixture is stirred at 0° C. for 30 min and at room temperature for 30 min. At 0° C., water is added and the mixture is warmed to room temperature and extracted with ethyl acetate. The organic phase is washed with sodium chloride solution, dried with magnesium sulfate and concentrated using a rotary evaporator. The crude material is dissolved in 6 ml of methanol and, at 0° C., 1.5 ml of 45% strength aqueous sodium hydroxide solution are added. At room temperature, 0.2 ml of dichloromethane are added, whereupon the solution becomes clear. The solution is stirred at room temperature for 16 hours, a little water is added and the mixture is extracted with ethyl ether. The aqueous phase is adjusted to pH 2–3 using 10% strength sulfuric acid and extracted twice with ethyl acetate, dried with magnesium sulfate and concentrated under reduced pressure.

Yield: 23 mg (8.2% of theory).

¹H-NMR (200 MHz, CD$_2$Cl$_2$): 10.50 (bs, 2H), 7.90 (d, 2H), 7.30–7.00 (m, 7H), 7.00 (t, 1H), 6.60 (m, 1H), 6.50 (m, 2H), 5.35 (m, 1H), 5.10 (t, 1H), 3.90 (m, 2H), 3.10 (m, 2H), 2.90–2.50 (m, 5H), 2.30 (m, 4H), 1.20–1.70 (m, 8H).

EX. 44

6-(4Carboxybenzyl)-9-(3-(4-phenylbutoxy)phenyl) nonanoic acid

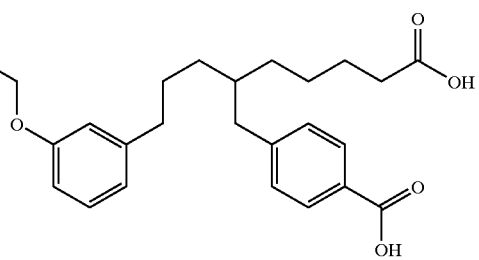

50 mg (0.10 mmol) of 6-(4-carboxybenzyl)-9-(3-(4-phenylbutoxy)phenyl-7-(Z) nonenoic acid from Ex. 43 and 19.5 mg of palladium/activated carbon 10% are added to 5 ml of ethyl acetate and hydrogenated at room temperature under atmospheric pressure, using hydrogen. After two hours, the mixture is filtered through Celite and the filtrate is concentrated.

Yield: 51 mg (100% of theory)

¹H-NMR (200 MHz, CDCl$_3$): 10.50 (bs, 2H), 7.90 (d, 2H), 7.30–7.00 (m, 8H), 6.60 (m, 31i), 3.90 (m, 2H), 2.70–2.40 (m, 6H), 2.30 (t, 2H), 1.70–1.20 (m, 15H).

EX. 45

Methyl 2-cyano-[(E)-2-[2-[(5-phenylpentyl)oxy]phenyl]ethenyl]-benzol-heptanoate

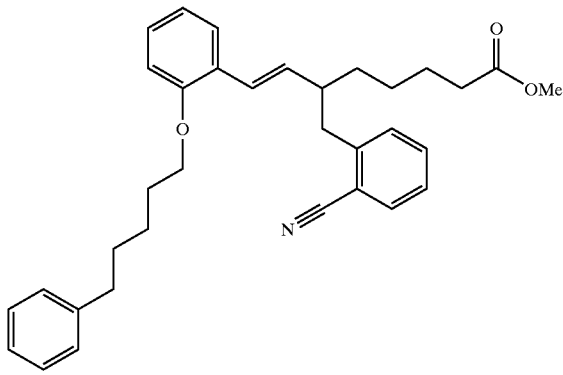

Under argon and at −78° C., 0.12 ml (0.19 mmol) of n-butyllithium (1.6 M in hexane) was added dropwise to a suspension of 117.6 mg (0.20 mmol) of triphenyl[2-[(5-phenylpentyl)oxy]phenyl]methyl]phosphonium bromide from Ex. X in 1 ml of absolute THF. The mixture was stirred at −78° C. for 5 min, the cooling bath was removed and the mixture was allowed to thaw to room temperature. The mixture was cooled to 0° C. and a solution of 45.0 mg (0.16 mmol) of methyl 7-(2-cyanophenyl)-6-formyl-heptanoate from Ex. XXIII in 1 ml of absolute THF was added dropwise. The mixture was allowed to thaw overnight, water was added and the mixture was extracted twice with ethyl acetate. The combined organic phases were dried over sodium sulfate and the solvent was removed. The product was purified by thin-layer chromatography.

Yield: 64.8 mg (64.8%) of a slightly yellowish oil.

E/Z=64:36

$^1$H-NMR (300 MHz, CDCl$_3$):

δ=1.19–1.84 (m, 12H), 2.17–2.33 (m, 2H), 2.48–2.60 (m, 1H), 2.64 (t, J=7.4 Hz, 2H), 2.72–3.08 (m, 2H), 3.63 (s, 3H), 3.75–3.94 (m, 2H), 5.42 (dd, J=10.6 Hz, J=9.8 Hz, 1H, Z-isomer), 5.98 (dd, J=15.9 Hz, J=9.1 Hz, 1H, E-isomer), 6.38–7.62 (m, 14H).

The following compounds were prepared analogously:

| Example | Structure | Yield [%] | $^1$H-NMR Data |
|---|---|---|---|
| 46 (from X and XXI) | 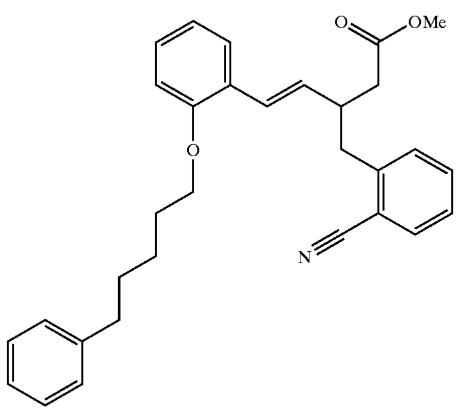 | 25.9 | E/Z=60:40<br>$^1$H-NMR(300MHz, CDCl$_3$): δ=1.40–1.84(m, 6H), 2.49(dd, J=18.7Hz, J=6.8Hz, 2H), 2.59–2.69(m, 2H), 2.93–3.14(m, 1H), 3.61(s, 3H, Z-isomer), 3.64(s, 3H, E-isomer), 3.74–3.97(m, 2H), 5.50(dd, J=11.0Hz, J=10.7Hz, 1H, Z-isomer), 6.09(dd, J=15.9Hz, J=8.1Hz, 1H, E-isomer), 6.46(d, J=11.7 Hz, 1H, Z-isomer), 6.56(d, J=16.0Hz, E-isomer), 6.65–7.61(m, 13H). |
| 47 (from X and XXII) | 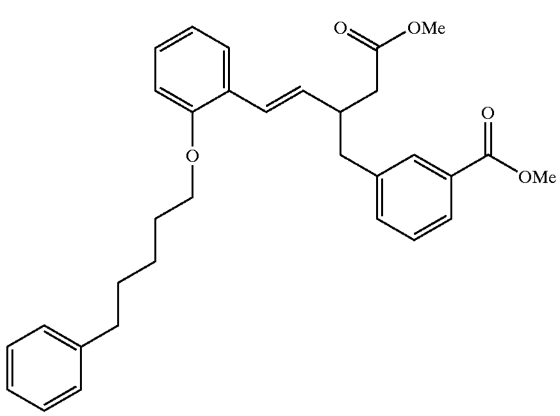 | 32.2 | E/Z=66:34<br>$^1$H-NMR(300MHz, CDCl$_3$): δ=1.40–1.88(m, 6H), 2.31–3.12(m, 5H), 3.58 (s, 3H Z-isomer), 3.62(s, 3H), E-isomer), 3.77–4.00(m, 2H), 3.88(s, 3H), 5.44(dd, J=11.2Hz, J=9.6Hz, 1H, Z-isomer), 6.08(dd, J=16.1Hz, J=8.3Hz, 1H, E-isomer), 6.45(d, J=11.7 Hz, 1H, Z-isomer), 6.63(d, J=16.1Hz, 1H, E-isomer), 6.71–7.95(m, 13H). |

-continued

| Example | Structure | Yield [%] | ¹H-NMR Data |
|---|---|---|---|
| 48 (from X and XIX) | 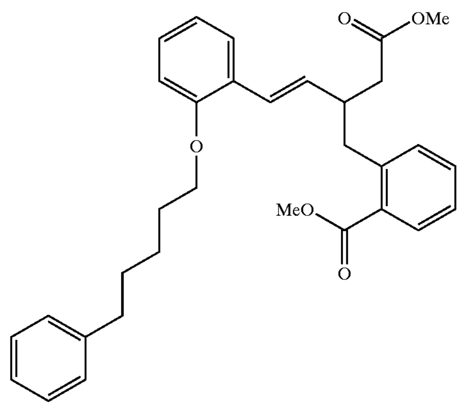 | 21.1 | E,Z=51:49<br>¹H-NMR(300MHz, CDCl₃): δ=1.39–1.85(m, 6H), 2.30–2.52(m, 2H), 2.56–2.70(m, 2H), 2.95–3.09(m, 1H), 3.54(s, 3H, Z-isomer), 3.60(s, 3H, E-isomer), 3.75(s, 3H, Z-isomer), 3.84(s, 3H, E-isomer), 3.76–3.94(m, 2H), 5.46 (dd, J=11.5Hz, J=10.3Hz, 1H, Z-isomer), 6.10(dd, J=60.1Hz, J=8.3 Hz, 1H, E-isomer), 6.43(d, J=11.7Hz, 1H, Z-isomer), 6.56(d, J=16.1Hz, 1H, E-isomer), 6.67–7.90(m, 13H). |
| 49 (from X and XX) | 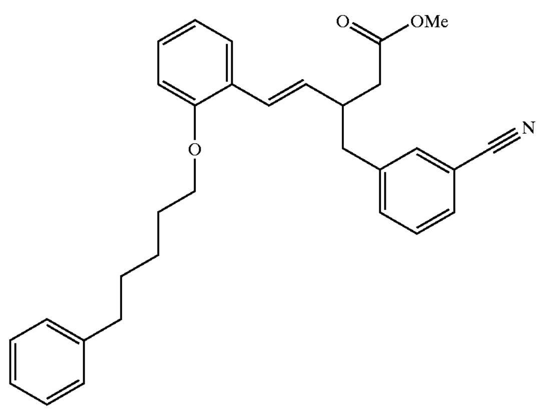 | 15.9 | E/Z=69:31<br>¹H-NMR(300MHz, CDCl₃): δ=1.40–1.90(m, 6H), 2.38–2.72(m, 4H), 2.92–3.08(m, 1H, E-isomer), 3.30–3.43(m, 1H, Z-isomer), 3.62(s, 3H, Z-isomer), 3.65(s, E-isomer), 3.86(t, J=6.4Hz, 2H, Z-isomer), 3.93(t, J=6.4Hz, E-isomer), 5.39(dd, J=11.7Hz, J=9.5 Hz, 1H, Z-isomer), 6.03(dd J=16.1Hz, J=8.1Hz, 1H, E-isomer), 6.46(d, J=11.5Hz, 1H, Z-isomer), 6.60(d, J=16.1 Hz, 1H, E-isomer), 6.73–7.54(m, 13H). |
| 50 (from X and XXIV) | 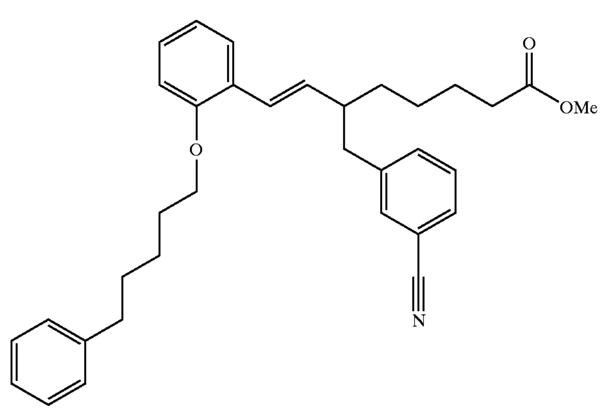 | 41.5 | E/Z=75:25<br>¹H-NMR(300MHz, CDCl₃): δ=1.19–1.88(m, 12H), 2.18–2.83(m, 7H), 3.62 (s, 3H), 3.86(t, J=6.4Hz, 2H, Z-isomer), 3.93(t, J=6.4Hz, 2H, E-isomer), 5.32(dd, J=11.3Hz, J=9.9 Hz, 1H, Z-isomer), 5.92(dd, J=15.9 Hz, J=8.7Hz, 1H, E-isomer), 6.41–7.47(m, 14H). |

| Example | Structure | Yield [%] | ¹H-NMR Data |
|---|---|---|---|
| 51 (from X and XXV) | 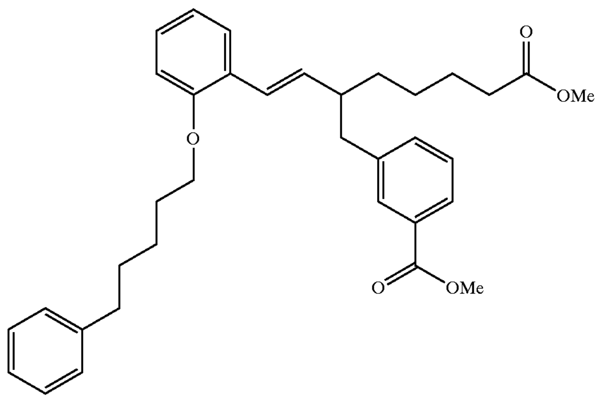 | 14.9 | E/Z=77:23<br>¹H-NMR(300MHz, CDCl₃): δ=1.16–1.85(m, 12H), 2.13–2.85(m, 7H), 3.61 (s, 3H, Z-isomer), 3.62(s, 3H, E-isomer), 3.87(s, 3H, Z-isomer), 3.88(s, 3H, E-isomer), 3.80–3.96(m, 2H, E-isomer), 4.03(t, J=6.6Hz, 2H, Z-isomer), 5.36(dd, J=11.7Hz, J=10.8 Hz, 1H, Z-isomer), 5.97(dd, J=16.1 Hz, J=8.7Hz, 1H, E-isomer), 6.40–7.90(m, 14H). |
| 52 (from X and XXVI) | 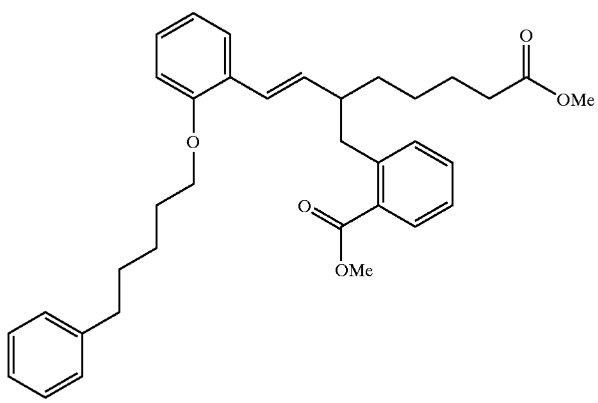 | 46.0 | E/Z=63:37<br>¹H-NMR(300MHz, CDCl₃): δ=1.17–1.84(m, 12H), 2.13–3.27(m, 7H), 3.61 (s, 3H), 3.77(s, 3H, Z-isomer), 3.83(s, 3H, E-isomer), 3.89(t, J=6.4Hz, 2H, E-isomer), 4.03(t, J=6.4Hz, 2H, Z-isomer), 5.36(dd, J 11.2=Hz, J=10.0 Hz, 1H, Z-isomer), 5.97(dd, J=15.9 Hz, J=9.1Hz, 1H, E-isomer), 6.35–7.86(m, 14H). |

EX. 53

3-Carboxy-[(E)-2-[2-[(5-phenylpentyl)oxy]phenyl]ethenyl]-benzenehep-tanoic acid

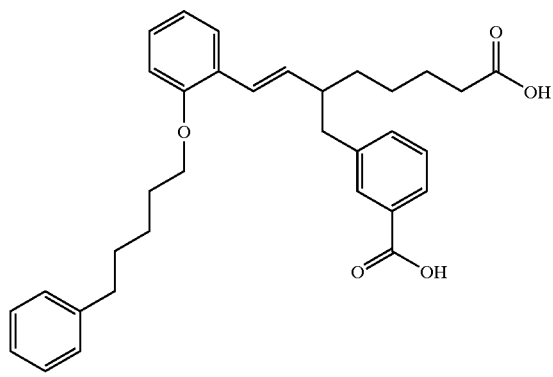

14.18 mg (331.7 μmol) of lithium hydroxide were added to a solution of 9.00 mg (16.6 mmol) of methyl 3-(methoxycarbonyl)-e-[(E)-2-[2-[(5-phenylpentyl)oxy)-phenyl]ethenyl]-benzeneheptanoate from Ex. 51 in 780 μl of THF, 260 μl of methanol and 260 μl of water. The mixture was stirred overnight, 3 M NaOH was added and the mixture was extracted with diethyl ether. The aqueous phase was acidified with 6 M HCl and extracted twice with diethyl ether and twice with ethyl acetate. The combined organic phases were dried over sodium sulfate and the solvent was removed.

Yield 7.8 mg (91.4%) of a colorless solid.

LC/MS: 5.33 min [m/z=514.4 (M+H), 532.5 (M+NH4)], 5.40 min [m/z=514.4 (M+H), 532.5 (M+NH)].

E/Z=77:23

¹H-NMR (300 MHz, CDCl₃):

δ=1.04–2.91 (m, 19H), 3.88 (t, J=6.2 Hz, 2H, Z-isomer), 3.94 (t, J=6.4 Hz, 2H, E-isomer), 5.39 (dd, J=11.2 Hz, J=10.4 Hz, 1H, Z-isomer), 6.02 (dd, J=15.1 Hz, J=8.7 Hz, 1H, E-isomer), 6.48 (d, J=11.7 Hz, 1H, Z-isomer), 6.59 (d, J=16.1 Hz, 1H, E-isomer), 6.73–7.99 (m, 13H).

The following compounds were prepared analogously:

| Example | Structure | Yield [%] | ¹H-NMR Data or LC-MS Data |
|---|---|---|---|
| 54 (from 49) | 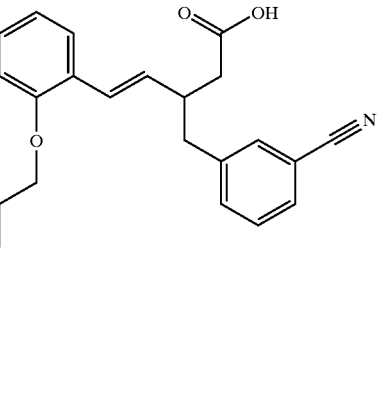 | 40.5 | E/Z=69:31<br>¹H-NMR(300MHz, CDCl₃): δ=1.36–1.88(m, 6H), 2.37–3.43(m, 7H), 3.85 (t, J=6.4Hz, 2H, Z-isomer), 3.93(t, J=6.4Hz, 2H, E-isomer), 5.41(dd, J=11.3 Hz, J=10.1Hz, 1H, Z-isomer), 6.05 (dd, J=16.1Hz, J=8.1Hz, 1H, E-isomer), 6.47(d, J=11.3Hz, 1H, Z-isomer), 6.61(d, J=16.1Hz, 1H, E-isomer), 6.72–7.50(m, 13H). |
| 55 (from 46) | 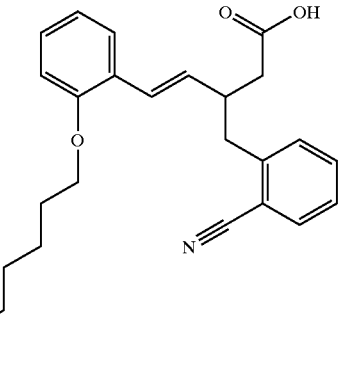 | 10.0 | LC/MS: 5.37 min[m/z=454.4(M+H), 471.5(M+NH₄)], 5.42 min[m/z=454.4 (M+H), 471.5(M+NH₄)]. |
| 56 (from 47) | 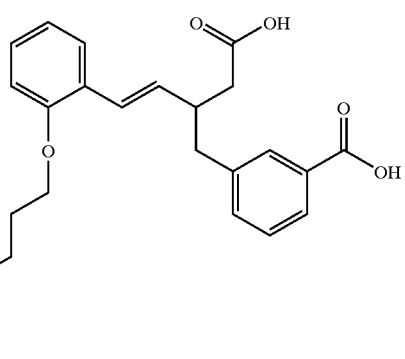 | 62.2 | LC/MS: 5.02 min[m/z=473.4(M+H), 490.4(M+NH₄)],<br>E/Z=66:34<br>¹H-NMR(300MHz, CDCl₃): δ=1.37–1.87(m, 6H), 2.39–3.51(m, 7H), 3.84 (t, J=6.4Hz, 2H, Z-isomer), 3.92(t, J=6.4Hz, 2H, E-isomer), 5.49(dd, J=11.3 Hz, J=10.1Hz, 1H, Z-isomer), 6.15 (dd, J=16.1Hz, J=8.1Hz, 1H, E-isomer), 6.48(d, J=11.5Hz, 1H, Z-isomer), 6.69(d, J=16.1Hz, 1H, E-isomer), 6.73–8.02(m, 13H). |

-continued

| Example | Structure | Yield [%] | ¹H-NMR Data or LC-MS Data |
|---|---|---|---|
| 57 (from 48) | 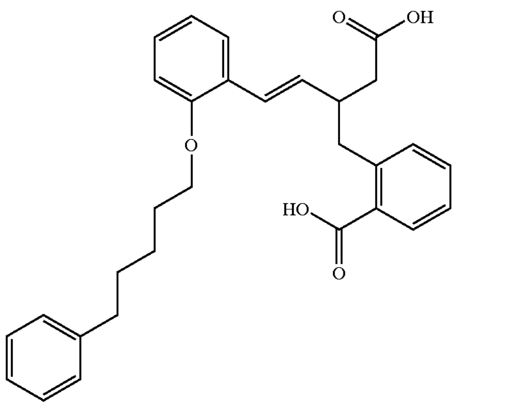 | 56.9 | LC/MS: 5.11 min[m/z=473.4(M+H), 490.4(M+NH₄)], 5.16 min[m/z=473.4 (M+H), 490.4(M+NH₄)]. E/Z=50:50 ¹H-NMR(300MHz, CDCl₃): δ=1.10–1.84(m, 6H), 2.16–2.78(m, 4H), 3.01–3.17(m, 1H), 3.32–3.52(m, 1H), 3.73–3.99(m, 2H), 5.56(dd, J=11.4 Hz, J=10.6Hz, 1H, Z-isomer), 6.14 (dd, J=15.9Hz, J=8.5Hz, 1H, E-isomer), 6.40–6.93(m, 4H), 7.03–7.45(m, 8H), 7.91(d, J=7.4Hz, 1H), 8.01(d, J=7.9Hz, 1H). |
| 58 (from 45) | 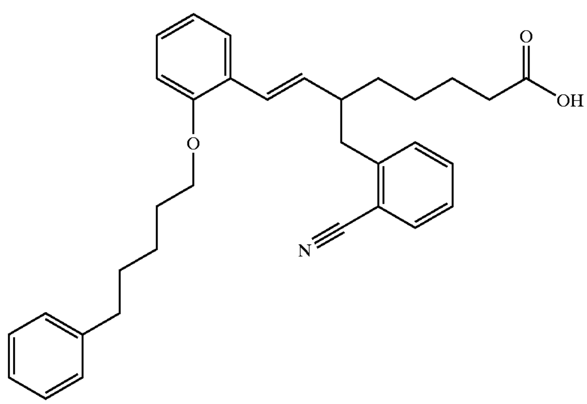 | 7.9 | LC/MS: 5.71 min [m/z=496.5(M+H), 513.5(M+NH₄)], 5.79 min [m/z=496.5 (M+H), 513.5(M+NH₄)]. E/Z=64:36 ¹H-NMR(300MHz, CDCl₃): δ=1.01–1.85(m, 12H), 2.18–2.59(m, 3H), 2.63 (t, J=7.6Hz, 2H), 2.73–3.24(m, 2H), 3.81–3.97(m, 2H), 5.42(dd, J=11.4 Hz, J=9.6Hz, 1H, Z-isomer), 5.98(dd, J=16.1Hz, J=9.0Hz, 1H, E-isomer), 6.36–7.66(m, 14H). |
| 59 (from 50) | 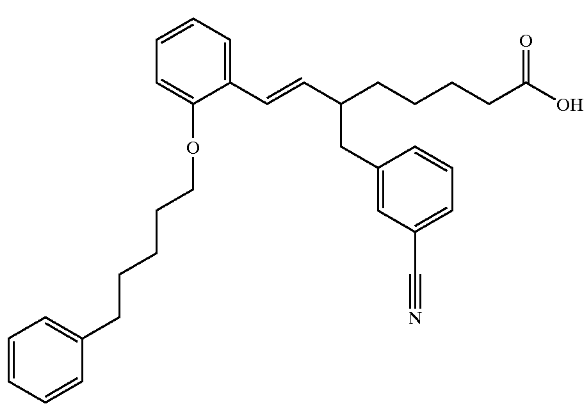 | 13.2 | LC/MS: 5.73 min[m/z=496.5(M+H), 513.5(M+NH₄)], 5.81 min[m/z=496.5 (M+H), 5.13.5(M+NH₄)]. E/Z=75:25 ¹H-NMR(300MHz, CDCl₃): δ=0.95–2.84(m, 19H), 3.87(t, J=6.4Hz, 1H, Z-isomer), 3.93(t, J=6.6Hz, 1H, E-isomer), 5.30–5.38(m, 1H, Z-isomer), 5.79(dd, J=16.1Hz, J=8.7Hz, 1H, E-isomer), 6.50(, d, J=16.1Hz, 1H, E-isomer), 6.70–7.48(m, 14H). |

| Example | Structure | Yield [%] | ¹H-NMR Data or LC-MS Data |
|---|---|---|---|
| 60 (from 52) | 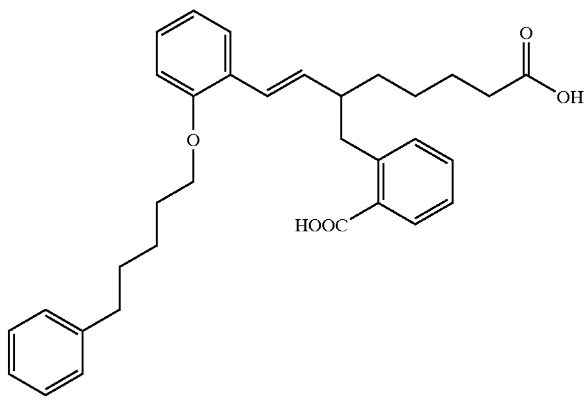 | 84.8 | LC/MS: 5.43 min[m/z=515.4(M+H), 532.5(M+NH₄)], 5.55 min[m/z=515.4 (M+H), 532.5(M+NH₄)], E/Z=63:37 |

LC/MS conditions: column: Symmetry C18 2.1*50 mm; mobile phase: acetonitrile/H$_{20}$ (0.1% formic acid); gradient: 10% acetonitrile to 90% acetonitrile; flow rate 0.5 ml/min; detector: UV 208–400 nm

EX. 61

Methyl 6-(4-(methoxycarbonyl)phenoxy]-8-[2-(4-phenylbutoxy)-phenyl]octanoate

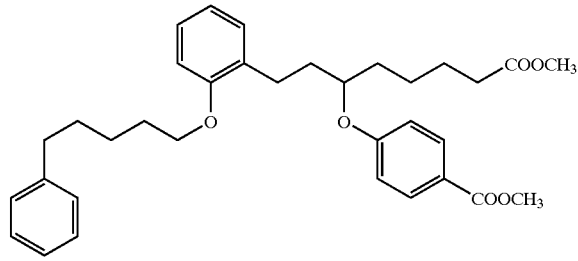

Over a period of 2 h, a solution of 100.0 mg (0.24 mmol) of methyl 6-hydroxy-8-{2-[(5-phenylpentyl)oxy]phenyl}octanoate from Ex. XXXIa and 63.32 mg (0.36 mmol) of DEAD in 2.5 ml of THF was added dropwise to a solution of 55.32 mg (0.36 mmol) of methyl 4-hydroxybenzoate and 95.36 mg (0.36 mmol) of triphenylphosphine in 2.5 ml of THF. The mixture was stirred at RT for 18 h, 40 ml of diethyl ether were added, the mixture was filtered and the solvent was removed. The product was purified chromatographically (silica gel, cyclohexane/EA 10:1). This gave 63.0 mg (47.5%) of a colorless oil.

¹H-NMR (400 MHz, CDCl₃): δ=0.76–1.78 (m, 1 1H), 1.84–2.04 (m, 2H), 2.28 (t, J=7.3 Hz, 2H), 2.61 (t, J=7.6 Hz, 2H), 2.64–2.77 (m, 2H), 3.63 (s, 3H), 3.85 (s, 3H), 3.86–3.94 (m, 2H), 4.22–4.34 (m, 2H), 6.74–6.86 (m, 4H), 7.01–7.31 (m, 7H), 7.92 (d, J=8.8 Hz, 2H).

The following compounds were prepared analogously:

| Ex. | Structure | Yield [%] | ¹H-NMR |
|---|---|---|---|
| 62 | 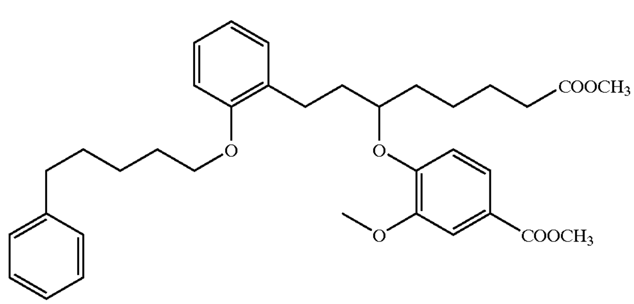 | 67.8 | ¹H NMR(400MHz, CDCl₃): δ=1.32–1.83(m, 12H), 1.86–1.97(m, 1H), 1.98–2.11(m, 1H), 2.29(t, J=7.3 Hz, 2H), 2.61(t, J=7.3Hz, 2H), 2.66–2.78(m, 2H), 3.63(s, 3H), 3.86(s, 3H), 3.88(s, 3H), 3.87–3.94(m, 2H), 4.21–4.34(m, 1H), 6.70(d, J=8.3Hz, 1H), 6.77–6.87(m, 2H), 7.01–7.07(m, 1H), 7.11–7.31(m, 6H), 7.51–7.60(m, 2H). |

| Ex. | Structure | Yield [%] | 1H-NMR |
|---|---|---|---|
| 63 | 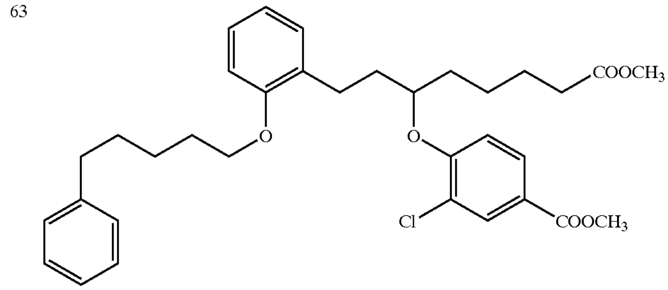 | 87.4 | 1H-NMR(400MHz, CDCl3): δ=1.35–1.84(m, 12H), 1.87–2.09(m, 2H), 2.29(t, J=7.3Hz, 2H), 2.61(t, J=7.6Hz, 2H), 2.65–2.81(m, 2H), 3.63 (s, 3H), 3.86(s, 3H), 3.87–3.99(m, 2H), 4.25–4.38(m, 1H), 6.71(d, J=8.6Hz, 1H), 6.75–6.86(m, 2H), 7.01–7.07(m, 1H), 7.11–7.36(m, 6H), 7.77–7.84(m, 1H), 8.01–8.05(m, 1H). |

EX. 64

Methyl 6-[2,6-dichloro4-(methoxycarbonyl)phenoxy]-8-{2-[(5-phenyl-pentyl)oxy]phenyl}octanoate

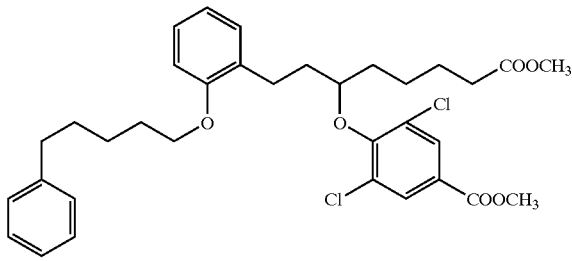

A suspension of 100.00 mg (0.21 mmol) of methyl 6-bromo-8-12-[(5-phenylpentyl)oxy]phenyl)octanoate from Ex. XXXI, 69.73 mg (0.32 mmol) of methyl 3,5-dichloro-4-hydroxy-benzoate and 58.13 mg (0.42 mmol) of potassium carbonate in 5 ml of DMF was stirred at 75° C. overnight. After the mixture had cooled to room temperature, 1 N NaOH was added, the mixture was extracted with diethyl ether, the combined organic phases were dried over Na2SO4 and the solvent was removed. The product was purified chromatographically (silica gel, cyclohexane/EA 10:1). This gave 90.9 mg (70.2%) of a colorless oil.

1H-NMR (300 MHz, CDCl3): δ 1.35–1.89 (m, 12H), 1.90–2.14 (m, 2H), 2.16–2.37 (m, 2H), 2.52–2.75 (m, 4H), 3.64 (s, 3H), 3.89 (m, 3H), 3.89–4.03 (m, 2H), 4.58–4.98 (m, 1H), 6.70–6.92 (m, 2H), 7.02–7.34 (m, 7H), 7.94 (s, 2H).

The following compounds were prepared analogously:

| Ex. | Structure | Yield [%] | 1H-NMR |
|---|---|---|---|
| 65 | 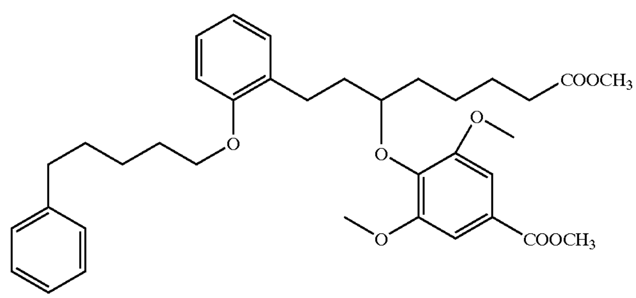 | 32.7 | 1H-NMR(400MHz, CDCl3): δ=1.41–1.95(m, 12H), 2.23–2.34(m, 3H), 2.57–2.67(m, 3H), 3.63(s, 3H), 2.69–2.78 (m, 2H), 3.83(s, 6H), 3.89(s, 3H), 3.86–4.00(m, 2H), 4.29–4.40(m, 1H), 6.74–6.86(m, 2H), 7.03–7.08(m, 1H), 7.08–7.30(m, 8H). |
| 66 | 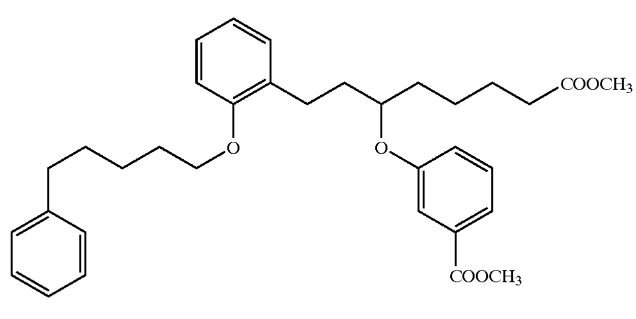 | 32.4 | 1H NMR(400MHz, CDCl3): δ=1.32–2.05(m, 14H), 2.05–2.20(m, 2H), 2.54–2.78(m, 4H), 3.63(s, 3H), 3.87–3.98 (m, 2H), 3.88(s, 3H), 4.22–4.35(m, 1H), 6.75–7.60(m, 13H). |

-continued

| Ex. | Structure | Yield [%] | ¹H-NMR |
|---|---|---|---|
| 67 | 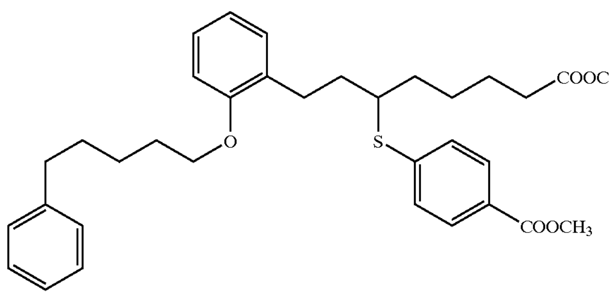 | 45.2 | ¹H NMR(400MHz, CDCl$_3$): δ=1.40–1.81(m, 12H), 1.90(q, J=6.8Hz, 2H), 2.28(t, J=7.6Hz, 2H), 2.61(t, J=7.8 Hz, 2H), 2.70–2.83(m, 2H), 3.22(quint, J=6.4Hz, 1H), 3.64(s, 3H), 3.84–3.99 (m, 2H), 3.88(s, 3H), 6.77–6.88(m, 2H), 7.04–7.30(m, 9H), 7.86(d, J=8.6 Hz, 2H). |

The following compounds were prepared analogously to Ex. 53:

| Ex. | Structure | Yield [%] | ¹H-NMR or LC-MS Data |
|---|---|---|---|
| 68 (from 61) | 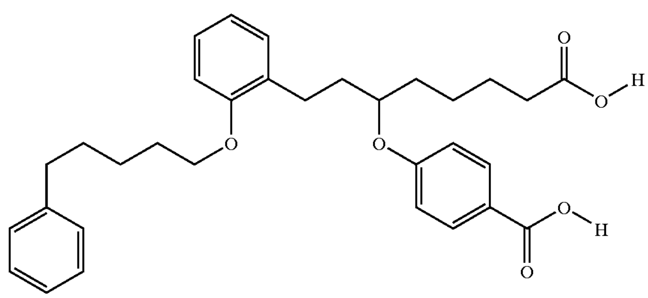 | 73.8 | ¹H NMR(400MHz, CDCl$_3$): δ=0.72–1.82(m, 12H), 1.83–2.05(m, 2H), 2.29–2.41(m, 2H), 2.61(t, J=7.8Hz, 2H), 2.65–2.79(m, 2H), 3.82–2.92 (m, 2H), 4.24–4.37(m, 1H), 6.74–6.88(m, 4H), 7.01–7.31(m, 7H), 7.97 (d, J=8.8Hz, 2H). |
| 69 (from 62) | 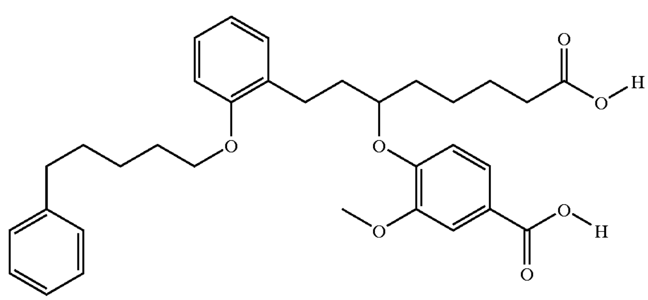 | 75.9 | ¹H NMR(300MHz, CDCl$_3$): δ=1.36–1.86(m, 12H), 1.87–2.12(m, 2H), 2.34(t, J=6.9Hz, 2H), 2.60(t, J=7.5 Hz, 2H), 2.72(t, J=7.4Hz, 2H), 3.87(s, 3H), 3.88–3.96(m, 2H), 4.25–4.38 (m, 1H), 6.68–7.67(m, 12H). |
| 70 (from 63) | 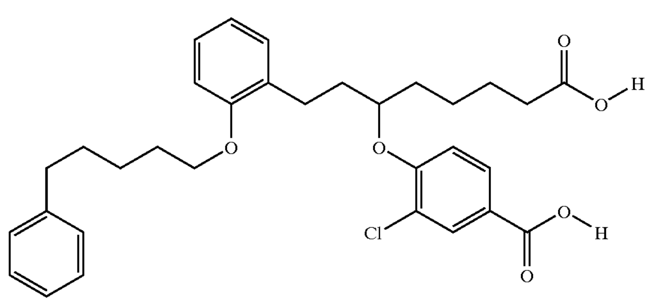 | 88.5 | ¹H NMR(300MHz, CDCl$_3$): δ=1.10–2.14(m, 14H), 2.35(t, J=6.9Hz, 2H), 2.61(t, J=7.6Hz, 2H), 2.65–2.82(m, 2H), 3.81–4.01(m, 2H), 4.29–4.45 (m, 1H), 6.69–6.88(m, 2H), 7.00–7.32(m, 8H), 7.82–8.10(m, 2H). |

| Ex. | Structure | Yield [%] | ¹H-NMR or LC-MS Data |
|---|---|---|---|
| 71 (from 64) | 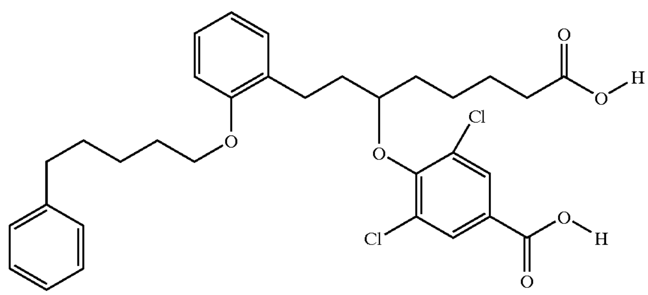 | 63.8 | ¹H NMR(300MHz, CDCl₃): δ=1.12–1.92(m, 12H), 1.92–2.13(m, 2H), 2.19–2.43(m, 2H), 2.53–2.78(m, 4H), 3.83–4.03(m, 2H), 4.59–4.80 (m, 1H), 6.68–6.94(m, 4H), 7.04–7.37(m, 5H), 7.98(s, 2H). |
| 72 (from 65) | 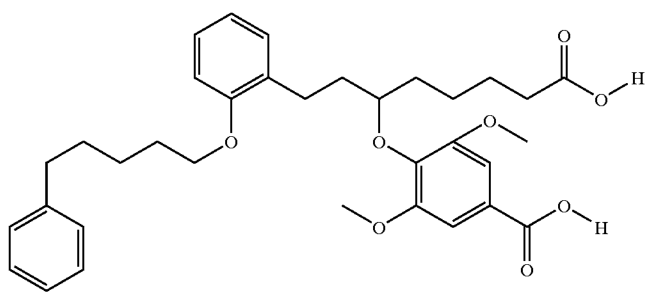 | 55.9 | ¹H NMR(300MHz, CDCl₃): δ=1.36–2.06(m, 8H), 2.23–2.41(m, 4H), 2.56–2.69(m, 3H), 2.70–2.82(m, 3H), 3.78–4.01(m, 4H), 3.83(s, 6H), 4.32–4.46(m, 1H), 6.74–7.35(m, 11H). |
| 73 (from 66) | 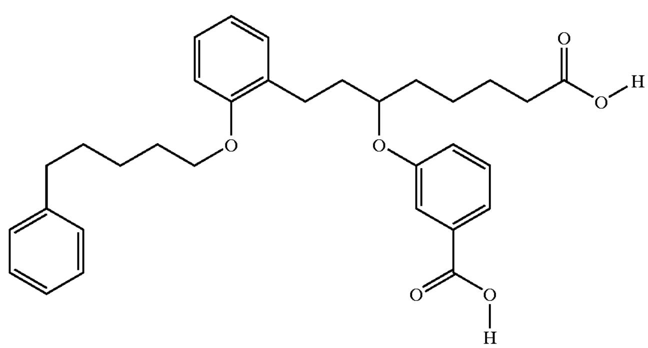 | 49.7 | LC/MS: 5.20 min[m/z=519.6(M+H), 536.5(M+NH₄)], 541.5(M+Na)]. |
| 74 (from 67) | 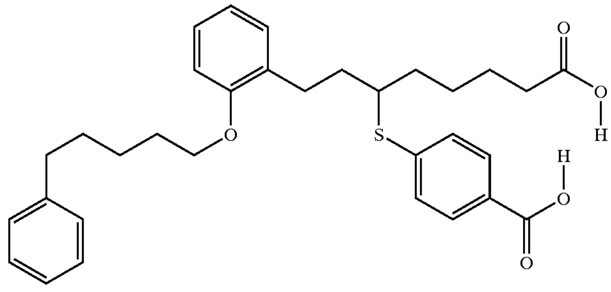 | 46.2 | ¹H NMR(300MHz, CDCl₃): δ=1.08–2.07(m, 14H), 2.22–2.46(m, 2H), 2.55–2.94(m, 4H), 3.16–3.41(m, 1H), 3.82–4.08(m, 2H), 6.75–6.96 (m, 2H), 7.04–7.42(m, 9H), 7.92(d, J=8.3Hz, 2H). |

LC/MS conditions: column: Symmetry C18 2.1*50 mm; mobile phase: acetonitrile/H₂O (0.1% formic acid); gradient: 10% acetonitrile to 90% acetonitrile; flow rate: 0.5 ml/min; detector: UV 208400 nm

EX. 75

Ethyl 8-(2-(4-chlorobenzyloxy)phenyl)-6-(4-ethoxycarbonylbenzyl)-7-(E)-octenoate 75a: Ethyl 6-(4-ethoxycarbonylbenzyl-8-(2-hydroxyphenyl)octanoate

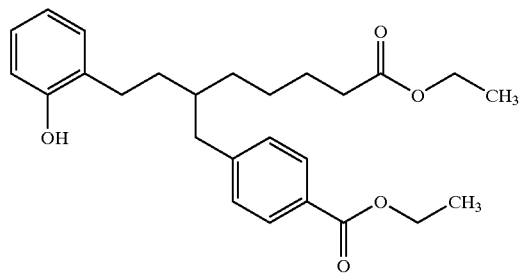

510.2 mg (1.44 mmol) of ethyl 6-(4-ethoxycarbonylbenzyl-8-(2-hydroxyphenyl)-7(E)-octenoate from Ex. 27a and 250 mg of palladium/activated carbon 10% are added to 20 ml of ethyl acetate and hydrogenated at room temperature under atmospheric pressure, using hydrogen. After five hours, the mixture is filtered through Celite and concentrated under reduced pressure.

Yield 507.9 mg (99.1% of theory)

$^1$H-NMR (400 MHz, CDCl$_3$): 7.95 (d, 2H, I=10 Hz), 7.20 (d, 2H), 7.00 (m, 2H), 6.80 (m, 2H), 4.90 (s, 1H), 4.35 (q, 1=6 Hz, 2H), 4.10 (m, 2H), 2.65 (m, 4H), 2.30 (m, 2H), 1.80–1.10(m, 1H)

75: Ethyl 4-[7-ethoxy-2-(2-12-[(4-ethylbenzyl)oxy]phenyl]ethyl)-7-oxoheptyl)benzoate

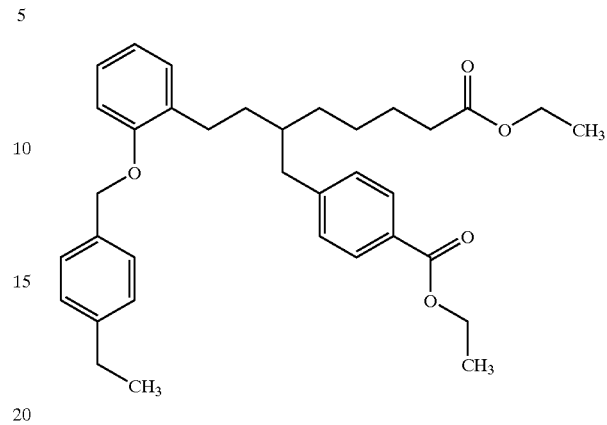

50 mg (0.117 mmol) of the phenol from Ex. 75a, 20 mg (0.129 mmol) of 4-ethylbenzyl chloride, 32 mg (0.234 mmol) of potassium carbonate and a catalytic amount of potassium iodide in 5 ml of 2-butanone are heated at reflux for 48 hours. The mixture is cooled, filtered and concentrated. For purification, the mixture is chromatographed on silica gel.

Yield: 34 mg (52.8% of theory)

$^1$H-NMR (200 MHz, CDCl$_3$): 7.95 (d, 2H, J=10 Hz), 7.40–7.10 (m, 8H), 6.90 (m, 2H), 5.00 (s, 2H), 4.35 (q, J=6 Hz, 2H), 4.10 (q, J=6 Hz, 2H), 2.75 (m, 6H), 2.30 (m, 2H), 1.80–0.80 (m, 18H)

The following compounds were prepared analogously:

| Example | Formula | Yield | NMR Data |
|---|---|---|---|
| 76 (from 75a and 4-n-butyl-benzyl bromide) | | 24.0 | $^1$H-NMR(300MHz, CDCl$_3$): 7.95(d, 2H, J=10Hz), 7.40–7.10(m, 8H), 6.90(m, 2H), 5.00(s, 2H), 4.35(q, J=6Hz, 2H), 4.10(q, J=6Hz, 2H), 2.65(m, 6H), 2.30(t, 2H), 1.80–0.80 (m, 22H) |

-continued

| Example | Formula | Yield | NMR Data |
|---|---|---|---|
| 77 (from 75a and 4-isopropylbenzyl chloride) | 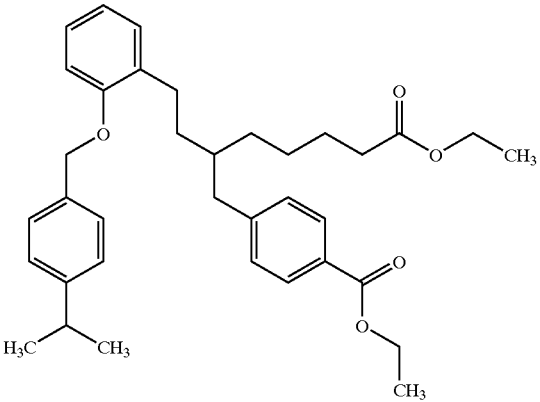 | 17.9 | $^1$H-NMR(300MHz, CDCl$_3$): 7.95(d, 2H, J=10Hz), 7.40–7.10(m, 8H), 6.90(m, 2H), 5.00(s, 2H), 4.35(q, J=6Hz, 2H), 4.10(q, J=6Hz, -2H), 2.90(m, 1H), 2.65(m, 4H), 2.30(t, 2H), 1.80–0.80(m, 19H) |

EX. 78

4-[6-Carboxy-2-(2-{2-[(4-ethylbenzyl)oxy]phenyl}ethyl)hexyl]benzoic acid

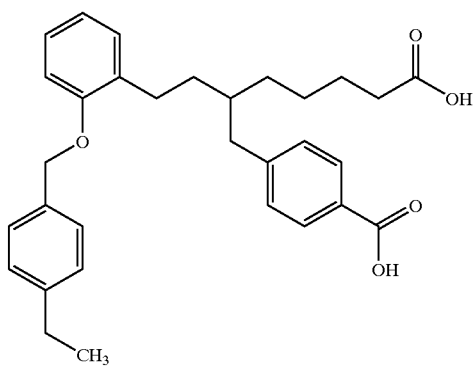

45 mg (0.08 mmol) of the diethyl ester from Ex. 75 are dissolved in 5 ml of methanol and treated with 0.5 ml of 45% strength aqueous sodium hydroxide solutions. The reaction mixture is allowed to warm to room temperature, and 0.3 ml of dichloromethane are added. After 20 hours of stirring at room temperature, the reaction solution is washed once with ether, acidified with 10% strength sulfuric acid and extracted twice with ethyl acetate, and the combined organic phases are filtered through Extrelute and concentrated.

Yield: 6.4 mg (21% of theory)

LC-MS: 488 (M); Rt: 4.99 min

The following compounds were prepared analogously:

| Example | Formula | Yield | LC-MS Data |
|---|---|---|---|
| 79 (from 76) | 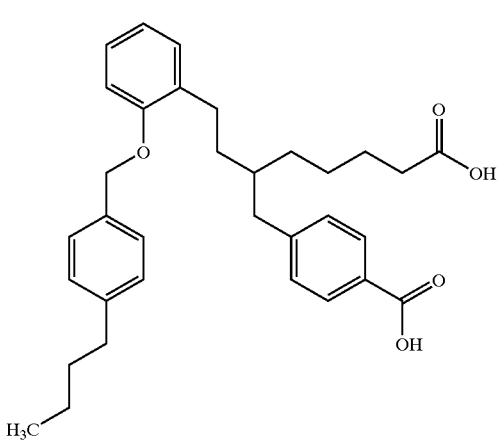 | 43.3 | LC-MS: 516(M); R$_t$: 5.35 min |

| Example | Formula | Yield | LC-MS Data |
|---|---|---|---|
| 80 (from 77) | 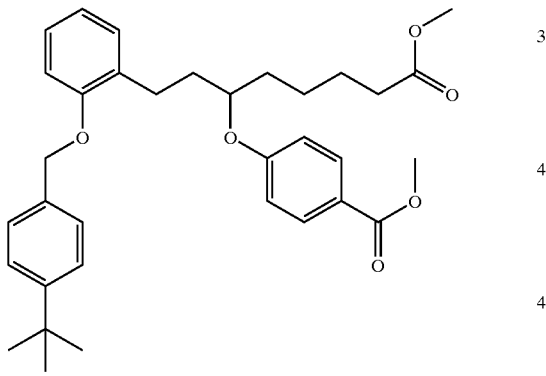 | 38.7 | LC-MS: 502(M); $R_t$: 5.12 min |

1) LC/MS conditions: column: Symmetry C18 2.1*50 mm; mobile phase: aceto-nitrile/$H_2O$ (0.1% formic acid); gradient: 10% acetonitrile to 90% acetonitrile; flow rate: 0.5 m/min; detector: WV 210 nm 81: Methyl 8-(2-(4-t-butylbenzyloxy)phenyl)-6-(4-methoxycarbonylphenyloxy)-octanoate

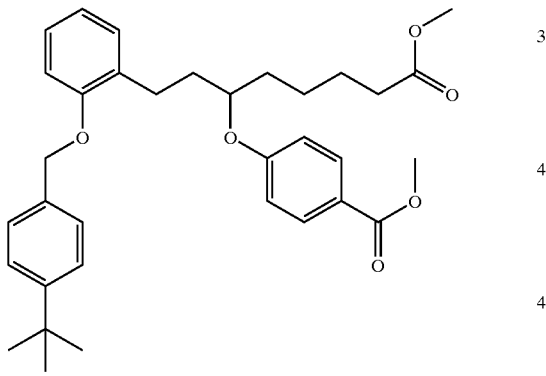

This compound was obtained analogously to Ex. 61, where the starting material analogous to Ex. XXXIa, methyl 6-hydroxy-8-i 2-[4-t-butylbenzyloxy]-phenyl}octanoate, was prepared according to Ex. XXXIa starting from 2-(4-t-butylbenzyloxy)benzyl alcohol.

Yield: 69.5%

$^1$H NMR (200 MHz, $CDCl_3$): δ=1.19–1.78 (m, 6H), 1.33 (s, 9H), 1.81–2.09 (m, 2H), 2.26 (1, J=7.6 Hz, 2H), 2.59–2.91 (m, 2H), 3.63 (s, 3H), 3.87 (s, 3H), 4.30 (quint, J=5.7 Hz, 1H), 5.01 (s, 2H), 6.77 (d, J=8.9 Hz, 2H), 6.81–6.95 (m, 2H), 7.03–7.43 (m, 6H), 7.89 (d, J=8.8 Hz, 2H).

82: 8-(2-(4-t-Butylbenzyloxy)phenyl)-6-(4-carboxyphenyloxy)-octanoic acid

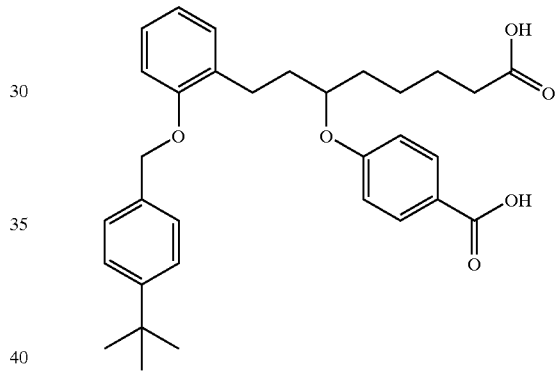

This compound was obtained analogously to Ex. 11 from Ex. 81:

Yield: 83.1%

$^1$H NMR (200 MHz, DMSO-$d_6$): δ=1.15–1.55 (m, 4H), 1.27 (s, 9M), 1.56–1.73 (m, 2H), 1.79–1.96 (m, 2H), 2.16 (t, J=6.8 Hz, 2H), 2.55–2.86 (m, 2H), 4.33–4.49 (m, 1H), 5.03 (s, 2H), 6.79–7.41 (m, 100H), 7.81 (d, J=8.8 Hz, 2H), 12.26 (bs, 2H).

What is claimed is:

1. A compound of formula (I),

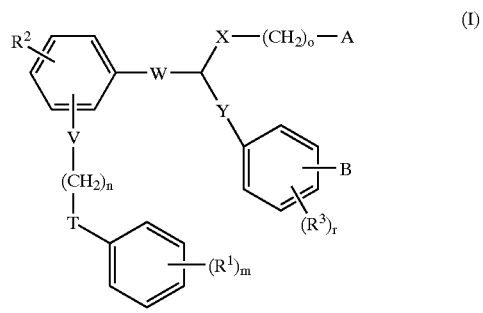

in which
V represents O,
n represents an integer from 1 to 10,

T is absent, $R^1$ represents hydrogen, straight-chain or branched alkyl or straight-chain or branched alkoxy having in each case up to 12 carbon atoms, halogen, $CF_3$, $OCF_3$ or CN, m represents 1 or 2, $R^2$ represents hydrogen, straight-chain or branched alkyl or straight-chain or branched alkoxy having in each case up to 12 carbon atoms, halogen, $CF_3$, $OCF_3$ or CN, W represents $CH_2CH_2$ or CH=CH is located on the phenyl ring in a position ortho to the radical V—$(CH_2)_n$-T-Ph-$(R^1)_m$, or represents $CH_2CH_2CH_2$ or $CH_2CH$=CH located on the phenyl ring in a position meta to the radical V—$(CH_2)_n$-T-Ph-$(R^1)_m$, X is absent or represents straight-chain or branched alkylene having up to 6 carbon atoms, O, $SCH_2$ or $S(O)_p$, in which p represents 0, 1 or 2 o represents an integer from 1 to 5

A represents tetrazolyl, tetrazolylmethylene, COOH, $CH_2COOH$, $COOR^4$, $CH_2COOR^5$, $CONR^6RR^7$ or CN, in which $R^4$ and $R^5$ independently of one another represent straight-chain or branched alkyl having up to 6 carbon atoms, $R^6$ and $R^7$ independently of one another represent hydrogen, straight-chain or branched alkyl having up to 6 carbon atoms, straight-chain or branched alkylsulfonyl having up to 12 carbon atoms, arylsulfonyl having 6 to 12 carbon atoms, or $R^6$ and $R^7$ together with the nitrogen atom to which they are attached form a 3- to 8-membered saturated heterocycle Y is absent or represents straight-chain or branched alkylene having up to 6 carbon atoms, O, $SCH_2$ or $S(O)_q$, in which q represents 0, 1 or 2

B represents tetrazolyl, tetrazolylmethylene, COOH, $CH_2COOH$, $COOR^8$, $CH_2COOR^9$, $CONR_{10}R^{11}$ or CN, in which $R^8$ and $R^9$ independently of one another represent straight-chain or branched alkyl having up to 6 carbon atoms, $R_{10}$ and $R_1$ independently of one another represent hydrogen, straight-chain or branched alkyl having up to 6 carbon atoms, straight-chain or branched alkylsulfonyl having up to 12 carbon atoms, arylsulfonyl having 6 to 12 carbon atoms, or $R_{10}$ and $R_{11}$ together with the nitrogen atom to which they are attached form a 3- to 8-membered saturated heterocycle, $R^3$ represents hydrogen, straight-chain or branched alkyl or straight-chain or branched alkoxy having in each case up to 12 carbon atoms, halogen, $CF_3$, $OCF_3$ or CN, and r represents 0, 1 or 2, or a salt or stereoisomer thereof.

2. A compound of formula (I),

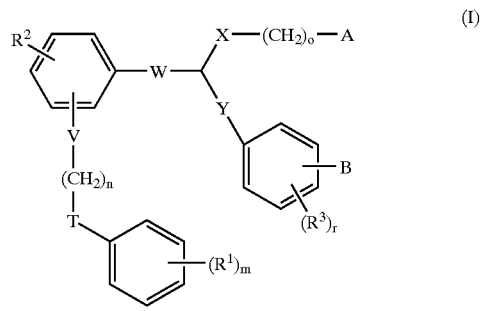

in which

V is absent n represents an integer from 1 to 3,

T is absent, $R_1$ represents hydrogen, straight-chain or branched alkyl or straight-chain or branched alkoxy having in each case up to 12 carbon atoms, halogen, $CF_3$, $OCF_3$ or CN, m represents 1 or 2, $R^2$ represents hydrogen, straight-chain or branched alkyl or straight-chain or branched alkoxy having in each case up to 12 carbon atoms, halogen, $CF_3$, $OCF_3$ or CN, W represents $CH_2CH_2$ or CH=CH located on the phenyl ring in a position ortho to the radical V—$(CH_2)_n$-T-Ph-$(R^1)_m$, or represents $CH_2CH_2CH_2$ or $CH_2CH$=CH located on the phenyl ring in a position meta to the radical V—$(CH_2)_n$-T-Ph-$(R^1)_m$, X is absent or represents straight-chain or branched alkylene having up to 6 carbon atoms, O, $SCH_2$ or $S(O)_p$, in which p represents 0, 1 or 2 o represents an integer from 1 to 5

A represents tetrazolyl, tetrazolylmethylene, COOH, $CH_2COOH$, $COOR^4$, $CH_2COOR^5$, $CONR^6R^7$ or CN, in which $R^4$ and $R^5$ independently of one another represent straight-chain or branched alkyl having up to 6 carbon atoms, $R^6$ and $R^7$ independently of one another represent hydrogen, straight-chain or branched alkyl having up to 6 carbon atoms, straight-chain or branched alkylsulfonyl having up to 12 carbon atoms, arylsulfonyl having 6 to 12 carbon atoms, or $R^6$ and $R^7$ together with the nitrogen atom to which they are attached form a 3- to 8-membered saturated heterocycle Y is absent or represents straight-chain or branched alkylene having up to 6 carbon atoms, O, $SCH_2$ or $S(O)_q$, in which q represents 0, 1 or 2

B represents tetrazolyl, tetrazolylmethylene, COOH, $CH_2COOH$, $COOR^8$, $CH_2COOR^9$, $CONR^{10}R^{11}$ or CN, in which $R^8$ and $R^9$ independently of one another represent straight-chain or branched alkyl having up to 6 carbon atoms, $R^{10}$ and $R^{11}$ independently of one another represent hydrogen, straight-chain or branched alkyl having up to 6 carbon atoms, straight-chain or branched alkyl-sulfonyl having up to 12 carbon atoms, arylsulfonyl having 6 to 12 carbon atoms,
or
$R^{10}$ and $R^{11}$ together with the nitrogen atom to which they are attached form a 3- to 8-membered saturated heterocycle, $R^3$ represents hydrogen, straight-chain or branched alkyl or straight-chain or branched alkoxy having in each case up to 12 carbon atoms, halogen, $CF_3$, $OCF_3$ or CN, and r represents 0, 1 or 2, or a salt or stereoisomer thereof.

3. The compound as claimed in claim 1,
in which
V represents O,
n represents an integer from 1 to 10,
T is absent,
$R^1$ represents hydrogen, straight-chain or branched alkyl or straight-chain or branched alkoxy having in each case up to 12 carbon atoms, halogen, $CF_3$, $OCF_3$ or CN,
m represents 1 or 2,
$R^2$ represents hydrogen, straight-chain or branched alkyl or straight-chain or branched alkoxy having in each case up to 12 carbon atoms, halogen, $CF_3$, $OCF_3$ or CN,
W represents $CH_2CH_2$ or CH=CH located on the phenyl ring in a position ortho to the radical V—$(CH_2)_n$-T-Ph-$(R^1)_m$,
or represents $CH_2CH_2CH_2$ or $CH_2CH$=CH located on the phenyl ring in a position meta to the radical V—$(CH_2)_n$-T-Ph-$(R^1)_m$,
X is absent,
o represents an integer from 1 to 4,
A represents COOH or $COOR^4$,
in which
$R^4$ represents alkyl having up to 2 carbon atoms,
Y represents O, S, SO, $SO_2$ or $CH_2$,
B represents COOH, $COOR^8$ or CN,
in which
$R^8$ represents alkyl having up to 2 carbon atoms,
$R^3$ represents hydrogen, straight-chain or branched alkoxy having up to 6 carbon atoms, F, Cl, Br or I, and
r represents 0, 1 or 2.

4. The compound as claimed in claim 1,
in which
V represents O,
n represents an integer from 1 to 6,
T is absent,
$R^1$ represents hydrogen, straight-chain or branched alkyl or straight-chain or branched alkoxy having in each case up to 6 carbon atoms, F, Cl, Br or $CF_3$,
m represents 1 or 2,
$R^2$ represents hydrogen or straight-chain or branched alkyl having up to 6 carbon atoms,
W represents $CH_2CH_2$ or CH=CH located on the phenyl ring in a position ortho to the radical V—$(CH_2)_n$-T-Ph-$(R^1)_m$,
or represents $CH_2CH_2CH_2$ or $CH_2CH$=CH located on the phenyl ring in a position meta to the radical V-$(CH_2)_n$-T-Ph-$(R^1)_m$,
X is absent,
O represents an integer from 1 to 4,
A represents COOH or $COOR^4$,
in which
$R^4$ represents alkyl having up to 2 carbon atoms,
Y represents O, S or $CH_2$,
B represents COOH, $COOR^8$ or CN,
in which
$R_8$ represents alkyl having up to 2 carbon atoms,
$R^3$ represents hydrogen, straight-chain or branched alkoxy having up to 4 carbon atoms, Cl or Br, and
r represents 0, 1 or 2.

5. The compound as claimed in claim 1,
in which
V represents O,
n represents an integer from 1 to 6,
T is absent,
$R^1$ represents hydrogen, straight-chain or branched alkyl or straight-chain or branched alkoxy having in each case up to 6 carbon atoms, F, Cl, Br or $CF_3$,
m represents 1 or 2,
$R^2$ represents hydrogen or straight-chain or branched alkyl having up to 6 carbon atoms,
W represents $CH_2CH_2$ or CH=CH located on the phenyl ring in a position ortho to the radical V—$(CH_2)_n$-T-Ph-$(R^1)_m$,
or represents $CH_2CH_2CH_2$ or $CH_2CH$=CH located on the phenyl ring in a position meta to the radical V—$(CH_2)_n$-T-Ph-$(R^1)_m$,
X is absent,
o represents an integer from 1 to 4,
A represents COOH,
Y represents O, S or $CH_2$,
B represents COOH,
$R^3$ represents hydrogen, straight-chain or branched alkoxy having up to 4 carbon atoms, Cl or Br, and
r represents 0, 1 or 2.

6. The compound as claimed in claim 2,
in which
V is absent,
n represents an integer from 1 to 3,
T is absent,
$R^1$ represents hydrogen, straight-chain or branched alkyl or straight-chain or branched alkoxy having in each case up to 12 carbon atoms, halogen, $CF_3$, $OCF_3$ or CN,
m represents 1 or 2,
$R^2$ represents hydrogen, straight-chain or branched alkyl or straight-chain or branched alkoxy having in each case up to 12 carbon atoms, halogen, $CF_3$, $OCF_3$ or CN,
W represents $CH_2CH_2$ or CH=CH located on the phenyl ring in a position ortho to the radical V—$(CH_2)_n$-T-Ph-$(R^1)_m$,
or represents $CH_2CH_2CH_2$ or $CH_2CH$=CH located on the phenyl ring in a position meta to the radical V—$(CH_2)_n$-T-Ph-$(R^1)_m$,
X is absent,
o represents an integer from 1 to 4,
A represents COOH or $COOR^4$,
in which
$R^4$ represents alkyl having up to 2 carbon atoms,
Y represents O, S, SO, $SO_2$ or $CH_2$, B represents COOH, COOR$^8$ or CN,
in which
R$^8$ represents alkyl having up to 2 carbon atoms,
R$^3$ represents hydrogen, straight-chain or branched alkoxy having up to 6 carbon atoms, F, Cl, Br or I, and
r represents 0, 1 or 2.

7. The compound as claimed in claim 2,
in which
V is absent,
n represents an integer from 1 to 3,
T is absent,
R$^1$ represents hydrogen, straight-chain or branched alkyl or straight-chain or branched alkoxy having in each case up to 6 carbon atoms, F, Cl, Br or CF$_3$,
m represents 1 or 2,
R$^2$ represents hydrogen or straight-chain or branched alkyl having up to 6 carbon atoms,
W represents CH$_2$CH$_2$ or CH=CH located on the phenyl ring in a position ortho to the radical V—(CH$_2$)$_n$-T-Ph-(R$^1$)$_m$,
or represents CH$_2$CH$_2$CH$_2$ or CH$_2$CH=CH located on the phenyl ring in a position meta to the radical V—(CH$_2$)$_n$-T-Ph-(R$^1$)$_m$,
X is absent,
o represents an integer from 1 to 4,
A represents COOH or COOR$^4$,
in which
R$^4$ represents alkyl having up to 2 carbon atoms,
Y represents O, S or CH$_2$,
B represents COOH, COOR$^8$ or CN,
in which
R$^8$ represents alkyl having up to 2 carbon atoms,
R$^3$ represents hydrogen, straight-chain or branched alkoxy having up to 4 carbon atoms, Cl or Br, and
r represents 0, 1 or 2.

8. The compound as claimed in claim 2,
in which
V is absent,
n represents 1 or 2,
T is absent,
R$^1$ represents hydrogen, straight-chain or branched alkyl or straight-chain or branched alkoxy having in each case up to 6 carbon atoms, F, Cl, Br or CF$_3$,
m represents 1 or 2,
R$^2$ represents hydrogen or straight-chain or branched alkyl having up to 6 carbon atoms,
W represents CH$_2$CH$_2$ or CH=CH located on the phenyl ring in a position ortho to the radical V—(CH$_2$)$_n$-T-Ph-(R$^1$)$_m$,
or represents CH$_2$CH$_2$CH$_2$ or CH$_2$CH=CH located on the phenyl ring in a position meta to the radical V—(CH$_2$)$_n$-T-Ph-(R$^1$)$_m$,
X is absent,
o represents an integer from 1 to 4,
A represents COOH,
Y represents O, S or CH$_2$,
B represents COOH,
R$^3$ represents hydrogen, straight-chain or branched alkoxy having up to 4 carbon atoms, Cl or Br, and
r represents 0, 1 or 2.

9. A pharmaceutical composition comprising at least one compound of the general formula (I) as claimed in claim 1 or 2.

10. A method for the treatment of hypertension, comprising administering to a host in need thereof an effective amount of a compound of general formula (I) as claimed in claim 1 or 2.

* * * * *